US012343253B2

(12) United States Patent
Nir et al.

(10) Patent No.: US 12,343,253 B2
(45) Date of Patent: Jul. 1, 2025

(54) PROSTHETIC HEART VALVE LEAFLET ASSEMBLIES AND METHODS

(71) Applicant: EDWARDS LIFESCIENCES CORPORATION, Irvine, CA (US)

(72) Inventors: Noam Nir, Pardes-Hanna (IL); Elena Sherman, Pardes Hana (IL); Tamir S. Levi, Zikhron Yaakov (IL); Michael Bukin, Pardes Hanna (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/433,626

(22) Filed: Feb. 6, 2024

(65) Prior Publication Data

US 2024/0173123 A1     May 30, 2024

Related U.S. Application Data

(63) Continuation of application No. 17/851,328, filed on Jun. 28, 2022, which is a continuation of application No. PCT/US2021/012146, filed on Jan. 5, 2021.
(Continued)

(51) Int. Cl.
*A61F 2/24* (2006.01)
*B29C 65/00* (2006.01)
(Continued)

(52) U.S. Cl.
CPC .......... *A61F 2/2415* (2013.01); *A61F 2/2418* (2013.01); *B29C 65/62* (2013.01);
(Continued)

(58) Field of Classification Search
CPC .... A61F 2/2415; A61F 2/2418; A61F 2/2436; A61F 2/2439; A61F 2220/0075;
(Continued)

(56) References Cited

U.S. PATENT DOCUMENTS

| 3,409,013 A | 11/1968 | Berry |
| 3,548,417 A | 12/1970 | Kisher |

(Continued)

FOREIGN PATENT DOCUMENTS

| DE | 0144167 C | 9/1903 |
| DE | 2246526 C3 | 7/1981 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig,"European Heart Journal, No. 13. pp. 704-708. 1992.
(Continued)

*Primary Examiner* — Bayan Salone
(74) *Attorney, Agent, or Firm* — Klarquist Sparkman, LLP; Joel B. German

(57) ABSTRACT

Assembly methods for installing a leaflet assembly to an expandable frame of a prosthetic heart valve are described. The leaflet assembly comprises a plurality of leaflets coupled together at adjacent tabs, which form respective commissure tab assemblies. The commissure tab assemblies are inserted into corresponding windows of support members of the expandable frame. One or more wedge members are inserted into the commissure tab assembly, e.g., between the adjacent tabs or with the adjacent tabs therebetween, to restrain radial motion of the commissure tab assembly with respect to the window. The window can be a closed window, and the wedge member insertion can be after the commissure tab assembly is inserted into the window. Alternatively, the window can be an open window or channel, and the wedge member insertion can be before the commissure tab assembly is installed in the window.

15 Claims, 41 Drawing Sheets

Related U.S. Application Data

(60) Provisional application No. 62/959,723, filed on Jan. 10, 2020.

(51) Int. Cl.
 *B29C 65/62* (2006.01)
 *B29L 31/00* (2006.01)

(52) U.S. Cl.
 CPC ... *B29C 66/1142* (2013.01); *A61F 2220/0075* (2013.01); *A61F 2240/001* (2013.01); *B29L 2031/7534* (2013.01)

(58) Field of Classification Search
 CPC ....... A61F 2240/001; A61F 2210/0076; B29C 65/62; B29L 2031/07
 See application file for complete search history.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |

(56) References Cited

U.S. PATENT DOCUMENTS

| | | |
|---|---|---|
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,696,743 B2 * | 4/2014 | Holecek ............... A61F 2/2412 623/2.12 |
| 8,747,463 B2 | 6/2014 | Fogarty et al. |
| 9,078,781 B2 | 7/2015 | Ryan et al. |
| 11,224,509 B2 | 1/2022 | Dasi et al. |
| 11,607,311 B2 * | 3/2023 | Eberhardt ............. A61F 2/2439 |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 * | 2/2004 | Spenser ............... A61F 2/9524 623/2.14 |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0295363 A1 * | 12/2011 | Girard ................. A61F 2/2412 623/1.26 |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023984 A1 * | 1/2013 | Conklin ................ A61F 2/2418 623/2.14 |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 * | 9/2014 | Schraut ............... A61F 2/2418 623/2.17 |
| 2014/0277419 A1 * | 9/2014 | Garde ................. A61F 2/2403 623/2.18 |
| 2014/0277424 A1 | 9/2014 | Oslund |

(56) References Cited

U.S. PATENT DOCUMENTS

| | | |
|---|---|---|
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1* | 11/2014 | Braido .............. A61F 2/2433 623/2.11 |
| 2015/0073545 A1 | 3/2015 | Braido |
| 2015/0073546 A1* | 3/2015 | Braido .............. A61L 27/54 623/1.26 |
| 2015/0135506 A1* | 5/2015 | White .............. A61F 2/2418 29/428 |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2018/0028310 A1* | 2/2018 | Gurovich .............. A61F 2/2433 |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |

FOREIGN PATENT DOCUMENTS

| | | | |
|---|---|---|---|
| DE | 19532846 A1 | 3/1997 | |
| DE | 19907646 A1 | 8/2000 | |
| DE | 10049813 C1 | 4/2002 | |
| DE | 19546692 C2 | 11/2002 | |
| DE | 10049812 B4 | 6/2004 | |
| DE | 19857887 B4 | 5/2005 | |
| DE | 10049815 B4 | 10/2005 | |
| DE | 10049814 B4 | 10/2006 | |
| EP | 0103546 A1 | 3/1984 | |
| EP | 0850607 A1 | 7/1998 | |
| EP | 1057460 A1 | 12/2000 | |
| EP | 1088529 A2 | 4/2001 | |
| EP | 1570809 A1 | 9/2005 | |
| EP | 1267753 B1 * | 10/2005 | ........... A61F 2/2418 |
| FR | 2788217 A1 | 7/2000 | |
| FR | 2815844 B1 | 1/2003 | |
| GB | 2056023 A * | 3/1981 | ........... A61F 2/2418 |
| GB | 2056023 B | 8/1983 | |
| SU | 1271508 A1 | 11/1986 | |
| WO | 9117720 A1 | 11/1991 | |
| WO | WO-9217118 A1 * | 10/1992 | ....... A61B 17/22012 |
| WO | 9301768 A1 | 2/1993 | |
| WO | WO-9724080 A1 * | 7/1997 | .............. A61F 2/07 |
| WO | 9829057 A1 | 7/1998 | |
| WO | 9930646 A1 | 6/1999 | |
| WO | 9933414 A1 | 7/1999 | |
| WO | 9940964 A1 | 8/1999 | |
| WO | 9947075 A1 | 9/1999 | |
| WO | WO-0018333 A1 * | 4/2000 | ........... A61F 2/2409 |
| WO | 0041652 A1 | 7/2000 | |
| WO | 0047139 A1 | 8/2000 | |
| WO | WO-0135878 A2 * | 5/2001 | .............. A61F 7/02 |
| WO | 0149213 A2 | 7/2001 | |
| WO | 0154625 A1 | 8/2001 | |
| WO | 0162189 A1 | 8/2001 | |
| WO | WO-0154624 A1 * | 8/2001 | ........... A61F 2/2412 |
| WO | 0164137 A1 | 9/2001 | |
| WO | 0176510 A2 | 10/2001 | |
| WO | 0222054 A1 | 3/2002 | |
| WO | 0236048 A1 | 5/2002 | |
| WO | WO-0241789 A2 * | 5/2002 | ....... A61B 17/00234 |
| WO | 0247575 A2 | 6/2002 | |
| WO | WO-0243620 A1 * | 6/2002 | ........... A61F 2/2418 |
| WO | WO-0249540 A2 * | 6/2002 | ........... A61F 2/2409 |
| WO | 03047468 A1 | 6/2003 | |
| WO | 2005034812 A1 | 4/2005 | |
| WO | 2005055883 A1 | 6/2005 | |
| WO | 2005084595 A1 | 9/2005 | |
| WO | 2005102015 A2 | 11/2005 | |
| WO | WO-2006014233 A2 * | 2/2006 | .............. A61F 2/91 |
| WO | 2006032051 A2 | 3/2006 | |
| WO | WO-2006034008 A2 * | 3/2006 | ........... A61B 17/24 |
| WO | 2006111391 A1 | 10/2006 | |
| WO | 2006127089 A1 | 11/2006 | |
| WO | 2006138173 A2 | 12/2006 | |
| WO | 2007047488 A2 | 4/2007 | |
| WO | 2007067942 A1 | 6/2007 | |
| WO | 2007097983 A2 | 8/2007 | |
| WO | 2008005405 A2 | 1/2008 | |
| WO | 2008015257 A2 | 2/2008 | |
| WO | WO-2008035337 A2 * | 3/2008 | ........... A61F 2/2409 |
| WO | 2008091515 A2 | 7/2008 | |
| WO | WO-2008147964 A1 * | 12/2008 | ........... A61F 2/2418 |
| WO | WO-2008150529 A1 * | 12/2008 | ........... A61F 2/2418 |
| WO | 2009033469 A1 | 3/2009 | |
| WO | 2009042196 A2 | 4/2009 | |
| WO | 2009053497 A1 | 4/2009 | |
| WO | 2009061389 A2 | 5/2009 | |
| WO | 2009094188 A2 | 7/2009 | |
| WO | 2009116041 A2 | 9/2009 | |
| WO | 2009149462 A2 | 12/2009 | |
| WO | 2010011699 A2 | 1/2010 | |
| WO | 2010121076 A2 | 10/2010 | |
| WO | WO-2013013074 A2 * | 1/2013 | ........... A61F 2/2418 |
| WO | 2013106585 A1 | 7/2013 | |
| WO | 2015085218 A1 | 6/2015 | |
| WO | WO-2021141888 A1 * | 7/2021 | ........... A61F 2/2415 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al., "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al., "Prototype Stent: Invivo Swine Studies in the Biliary System1", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

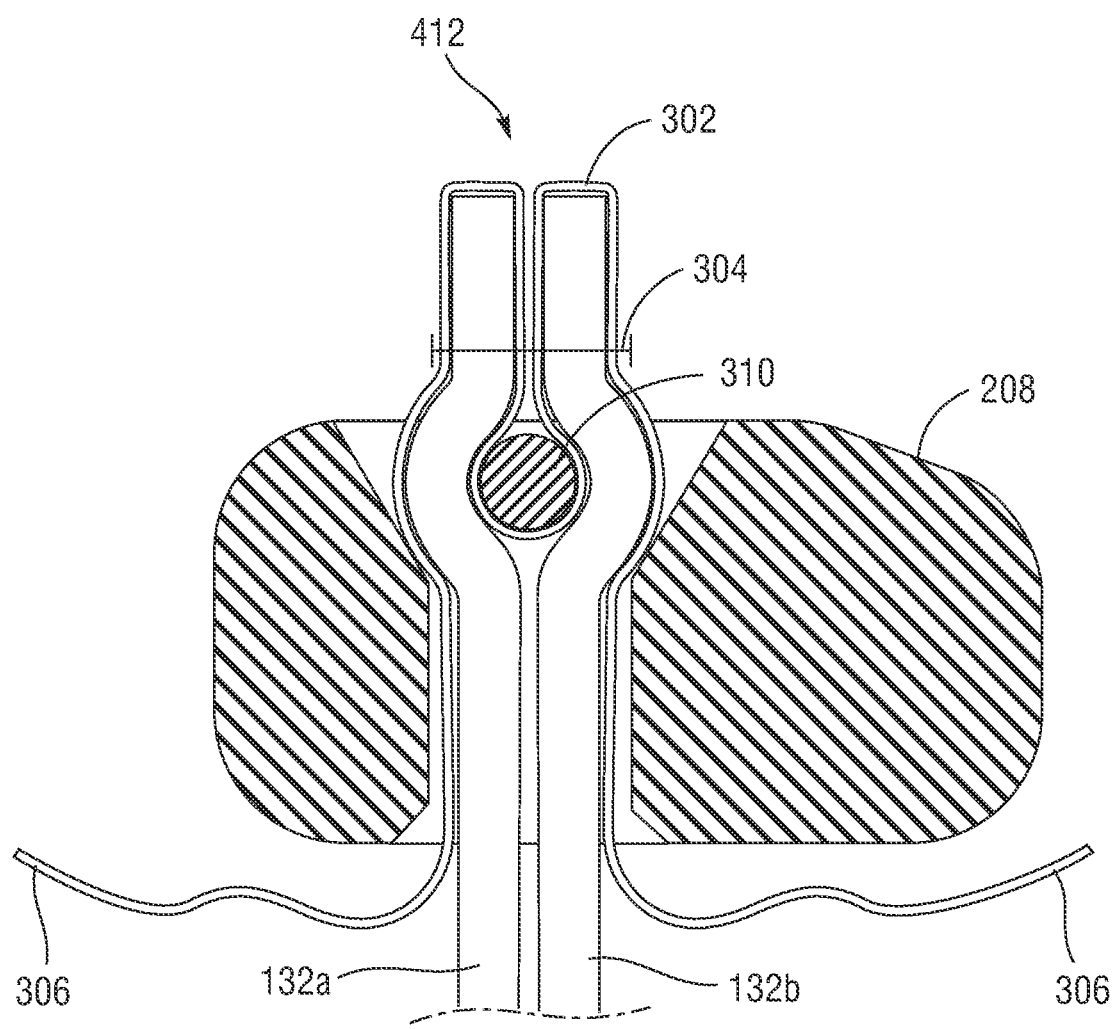

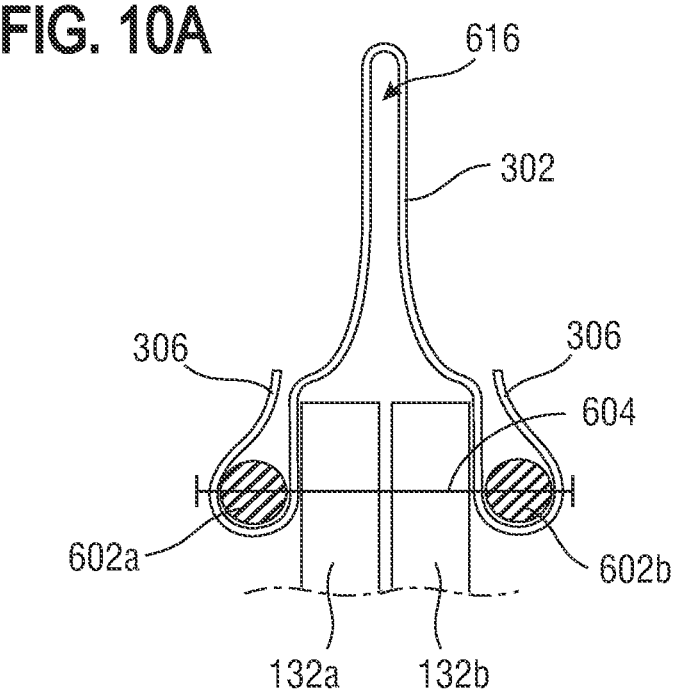
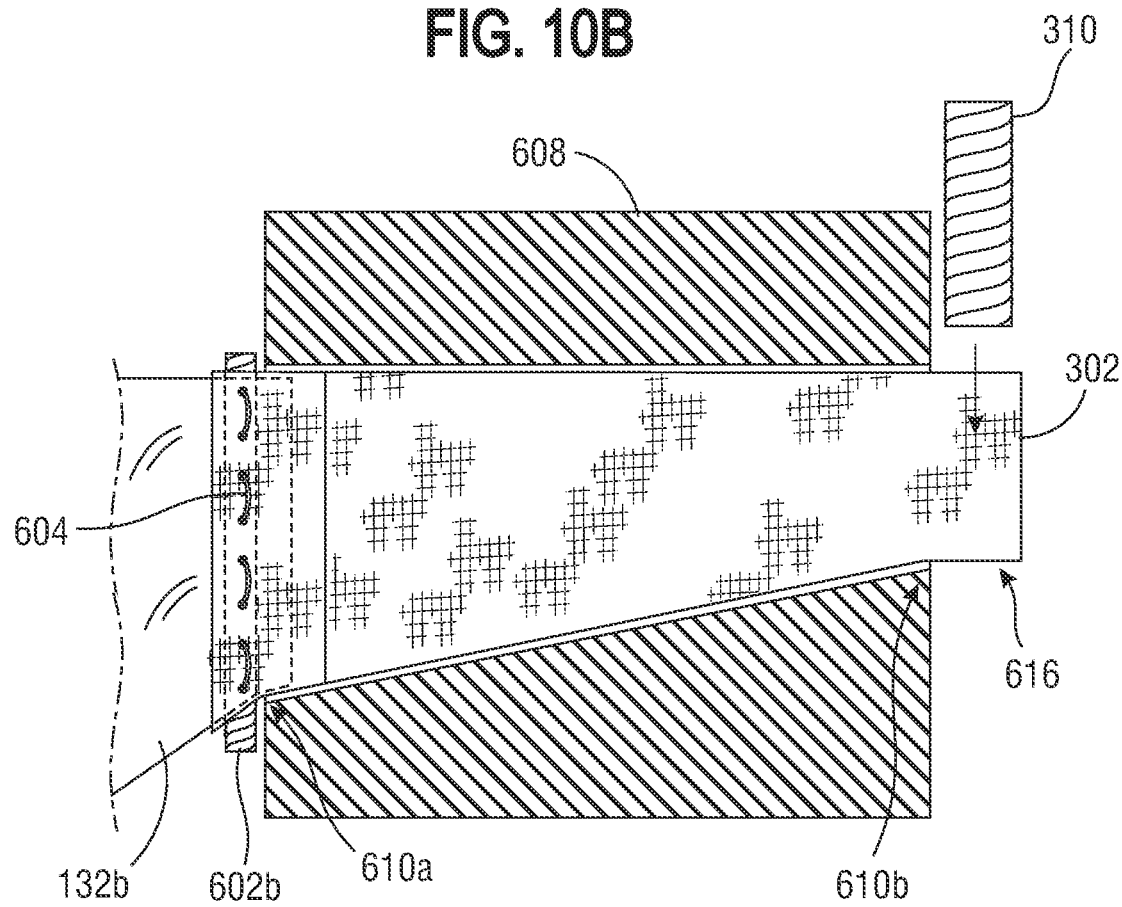

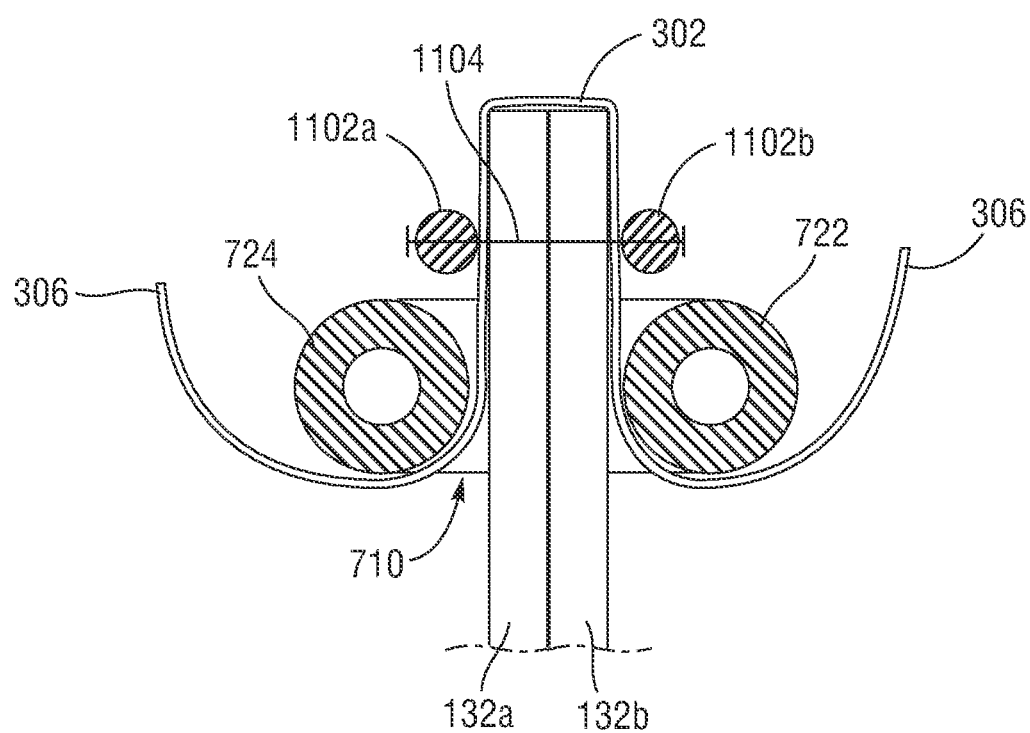

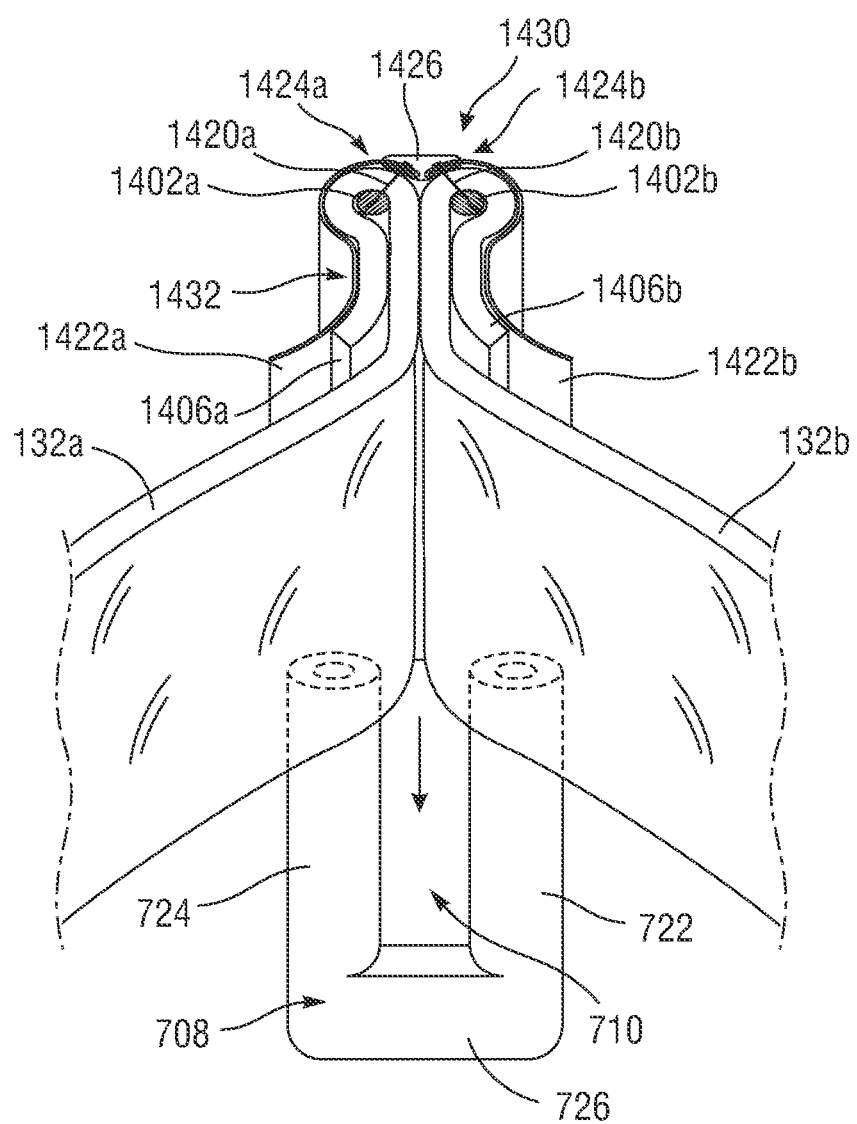

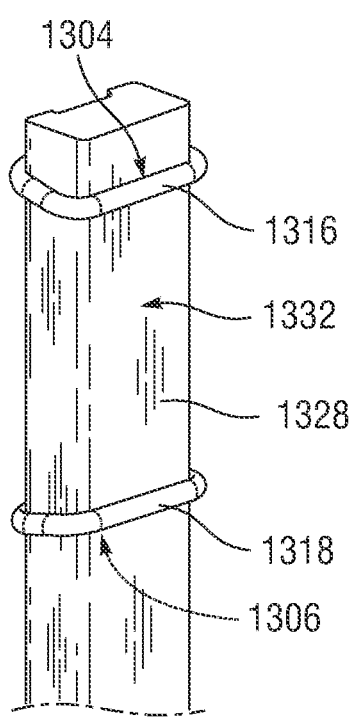
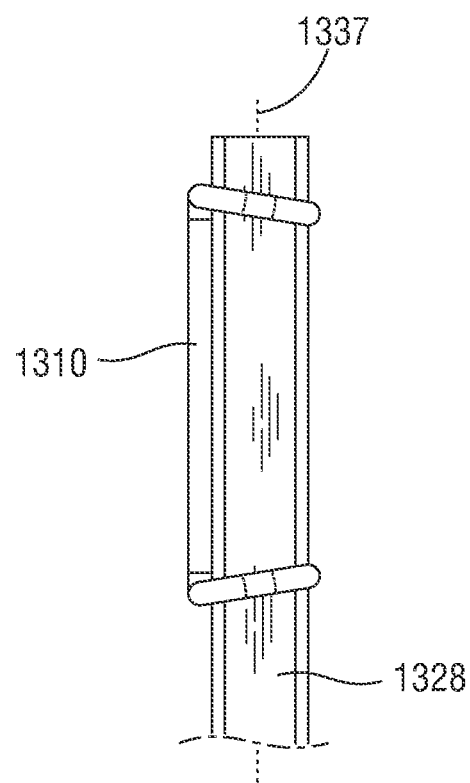

PROSTHETIC HEART VALVE LEAFLET ASSEMBLIES AND METHODS

CROSS REFERENCE TO RELATED APPLICATIONS

This application is a continuation of U.S. patent application Ser. No. 17/851,328, filed Jun. 28, 2022, which is a continuation of a PCT Patent Application No. PCT/US2021/012146, entitled "ASSEMBLY METHODS FOR A PROSTHETIC HEART VALVE LEAFLET," filed Jan. 5, 2021, which claims the benefit of U.S. Provisional Application No. 62/959,723, entitled "PROSTHETIC HEART VALVE LEAFLET ASSEMBLIES AND METHODS," filed Jan. 10, 2020, all of which are incorporated by reference herein in their entirety.

FIELD

The present disclosure relates to prosthetic heart valves, in particular, to methods and assemblies for forming and installing leaflet assemblies to frames of such prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size. Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Expandable, transcatheter heart valves can comprise an annular metal frame or stent and prosthetic leaflets mounted inside the frame. The leaflets can be attached to commissure posts of the frame via commissure tab assemblies. Each commissure tab assembly can be preassembled by connecting tabs of adjacent leaflets to each other and then attached by suture to the commissure posts of the frame. However, such commissure tab assemblies may be relatively complex and time-consuming to assemble. Moreover, attachment of the commissure tab assembly to the commissure post may be subject to undesirable wear along the numerous stitches required. The stability of the mounted commissure tab assembly may deteriorate due to displacement of the commissure tab assembly during assembly handling, crimping, or valve expansion, for example, the assembly rotating around the commissure post or sliding axially along the commissure post.

SUMMARY

Described herein are embodiments of prosthetic heart valves and methods for assembling prosthetic heart valves. In some embodiments, a leaflet assembly, which forms a valvular structure, is supported by an expandable annular frame of the prosthetic heart valve. The leaflet assembly comprises a plurality of leaflets coupled together at adjacent tabs, which form respective commissure tab assemblies. These commissure tab assemblies can be inserted into corresponding commissure windows of support members of the annular frame in order to couple the leaflet assembly to the frame. One or more wedge members can be inserted into the commissure tab assembly, between the adjacent tabs or with the adjacent tabs therebetween, to restrain radial motion of the commissure tab assembly with respect to the commissure window. In some embodiments, the commissure window is a closed window (e.g., having openings only facing a radial direction of the annular frame), and the wedge member insertion is after the commissure tab assembly is inserted into the commissure window. In other embodiments, the commissure window is an open window or channel (e.g., having an opening that faces an axial direction of the annular frame), and the wedge member insertion is before the commissure tab assembly is inserted into the commissure window. Embodiments of the disclosed subject matter may thus offer simple and cost-effective methods for reliably mounting the leaflet assembly to the heart valve while avoiding stitching sutures (or at least reducing the impact thereof) through dynamic portions of the leaflets, thereby reducing the risk of leaflet tearing.

Any of the various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosed technology will become more apparent from the following detailed description, which proceeds with reference to the accompanying figures.

BRIEF DESCRIPTION OF THE DRAWINGS

FIGS. 7A-7C are top down views illustrating sequential stages in assembling a commissure tab assembly to a closed window of a support member, according to a third example.

FIGS. 10A-10B are top down and cross-sectional side views, respectively, of a first stage in assembling a commissure tab assembly to a tapered closed window of a support member, according to a sixth example.

FIGS. 16A-16C are various views illustrating sequential stages in assembling a commissure tab assembly to an open window of a support member, according to an eleventh example.

FIGS. 19A-19D are various views illustrating sequential stages in assembling a commissure tab assembly to an open window of a support member, according to a fourteenth example.

FIGS. 20A, 20B, and 20D are rear perspective, side, and front views, respectively, of an open commissure window formed using a wireform on a support member, according to one or more embodiments of the disclosed subject matter.

DETAILED DESCRIPTION

Described herein are examples of prosthetic heart valves, annular frames with commissure support posts and leaflet assemblies for prosthetic heart valves, and methods for assembling leaflet assemblies to commissure support posts of annular frames to form prosthetic heart valves. A leaflet assembly, which forms a valvular structure, is supported by an expandable annular frame of the prosthetic heart valve. The leaflet assembly comprises a plurality of leaflets coupled together at adjacent tabs, which form respective commissure tab assemblies. These commissure tab assemblies can be inserted into corresponding commissure windows of support members of the annular frame in order to couple the leaflet assembly to the frame. One or more wedge members can be inserted into the commissure tab assembly, between the adjacent tabs or with the adjacent tabs therebetween, to restrain radial motion of the commissure tab assembly with respect to the commissure window. In some embodiments, the commissure window is a closed window (e.g., having openings only facing a radial direction of the annular frame), and the wedge member insertion is after the commissure tab assembly is inserted into the commissure window. In other embodiments, the commissure window is an open window or channel (e.g., having an opening that faces an axial direction of the annular frame), and the wedge member insertion is before the commissure tab assembly is inserted into the commissure window. As a result, a position of the leaflet assembly for a prosthetic heart valve may be effectively locked in place during assembly and use of the prosthetic heart valve, and a time and effort for securing the leaflet assembly to the frame of the prosthetic heart valve may be reduced.

Figure 1A:
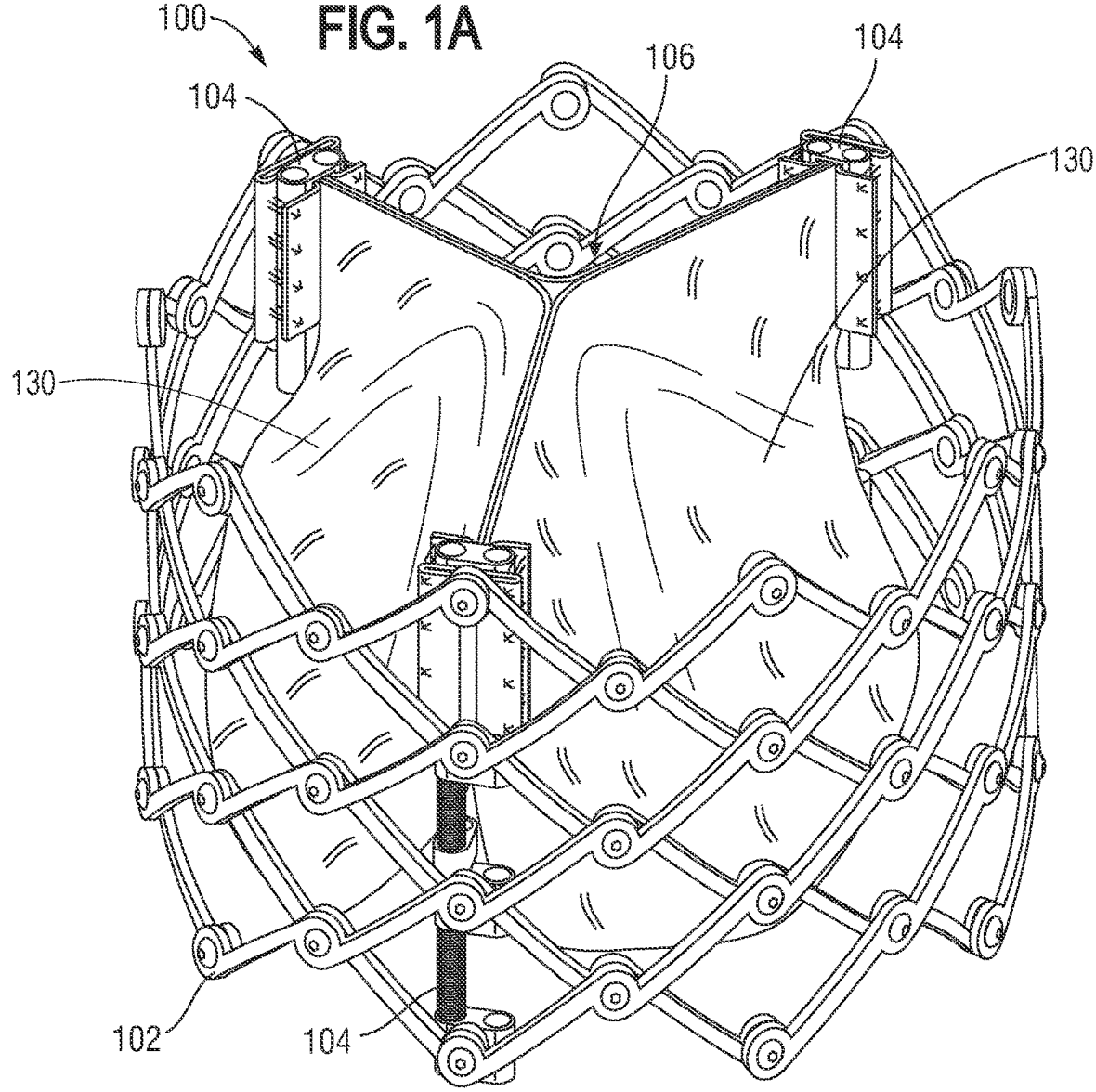
FIGS. 1A-1B are perspective views of exemplary mechanically-expandable prosthetic heart valves, according to one or more embodiments of the disclosed subject matter.

FIG. 1A shows an exemplary prosthetic heart valve 100, according to one or more embodiments of the disclosed subject matter. The prosthetic heart valve 100 can be radially compressible and expandable between a radially compressed configuration for delivery into a patient and a radially expanded configuration (as shown in FIG. 1A). In particular embodiments, the prosthetic heart valve 100 can be implanted within the native aortic annulus, although it also can be implanted at other locations in the heart, including within the native mitral valve, the native pulmonary valve, or the native tricuspid valve.

The prosthetic heart valve 100 can include an annular stent or frame 102. The prosthetic valve 100 also includes one or more actuators 104 for expanding/compressing the frame 102 and a valvular structure 106 configured for allowing blood flow through the frame 102 in one direction. The frame 102 can have a first axial end and a second axial end. In the depicted embodiment, the first axial end (e.g., where valvular structure 106 attaches to actuators 104) can be an inflow end, and the second axial end (e.g., opposite actuators 104) can be an outflow end. The outflow end can be coupled to a delivery apparatus for delivering and implanting the prosthetic heart valve 100 within the native aortic valve is a transfemoral, retrograde delivery approach. Thus, in the delivery configuration of the prosthetic heart valve, the outflow end is the proximal-most end of the prosthetic valve. In other embodiments, the inflow end can be coupled to the delivery apparatus, depending on the particular native valve being replaced and the delivery technique that is used (e.g., trans-septal, transapical, etc.). For example, the inflow end can be coupled to the delivery apparatus (and therefore would be the proximal-most end of the prosthetic heart valve in the delivery configuration) when delivering the prosthetic heart valve to the native mitral valve via a trans-septal delivery approach.

Figure 3:
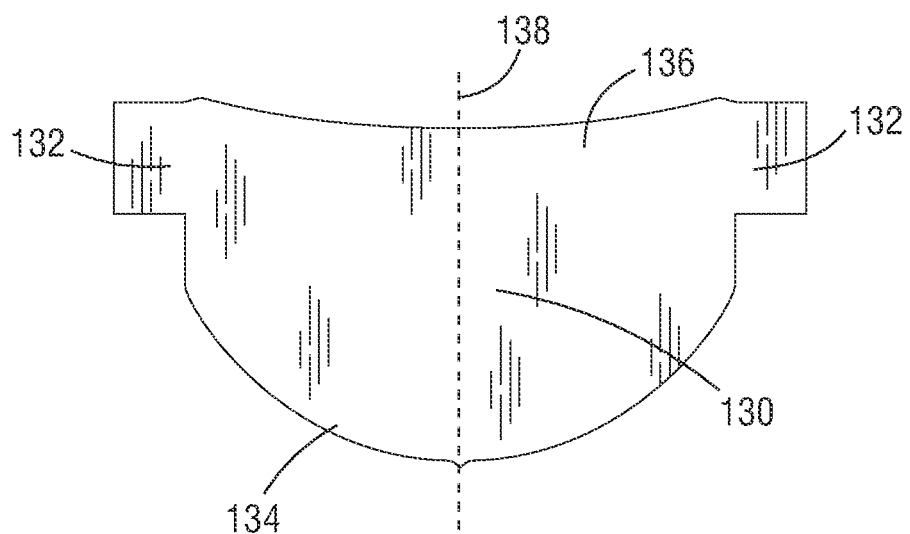
FIG. 3 is a plan view of an individual leaflet that can be used to form a leaflet assembly for a prosthetic heart valve, according to one or more embodiments of the disclosed subject matter.

The valvular structure 106 can be configured to regulate the flow of blood through the prosthetic heart valve 100 from the inflow end to the outflow end. The valvular structure 106 can include, for example, a leaflet assembly formed by one or more leaflets (three leaflets illustrated in FIG. 1A) made of a flexible material. As shown in FIG. 3, each leaflet 130 can comprise a main, cusp edge portion 134, two leaflet tabs (also referred to herein as commissure tabs) 132 at opposing ends of the cusp edge portion 134, and an upper edge portion 136. The cusp edge portion 134, leaflet tabs 132, and upper edge portion 136 may be arranged around an outer perimeter of the leaflet 130, with the upper edge portion 136 extending between the two leaflet tabs 132 at an upper edge of the leaflet 22 and the cusp edge portion 134 extending between the two leaflet tabs 132 at a lower edge of the leaflet 130. As used here, "upper" and "lower" may be relative to a central longitudinal axis of the prosthetic heart valve 100 when the leaflet assembly is installed and coupled to frame 102 of the prosthetic heart valve 100.

In some embodiments, the cusp edge portion 134 has a curved, scalloped shape (as shown in FIG. 3). Thus, the cusp edge portion 134 may curve between the two leaflet tabs 132. FIG. 3 further illustrates a centerline 138 for each of the individual leaflets 130, which may also be a centerline of the leaflet assembly. For example, when assembled, the centerlines 138 for each of the leaflets 130 may overlap. Further, as shown in FIG. 3, the leaflet tabs 132 may be arranged at opposing ends of the cusp edge portion 134, across the centerline 138 from one another. In some embodiments, the leaflets and/or components of the leaflet assembly may have symmetry with respect to the centerline 138.

The leaflets 130 of the leaflet assembly can be made from in whole or part, biological material, bio-compatible synthetic materials, or other such materials. Suitable biological material can include, for example, bovine pericardium (or pericardium from other sources). Further details regarding transcatheter prosthetic heart valves, including the manner in which the valvular structure can be coupled to the frame 102 of the prosthetic heart valve 100, can be found, for example, in U.S. Pat. Nos. 6,730,118, 7,393,360, 7,510,575, 7,993,394, and 8,652,202, and U.S. Patent Application Publication No. 2018/0325665, all of which are incorporated herein by reference in their entireties.

Figure 1B:
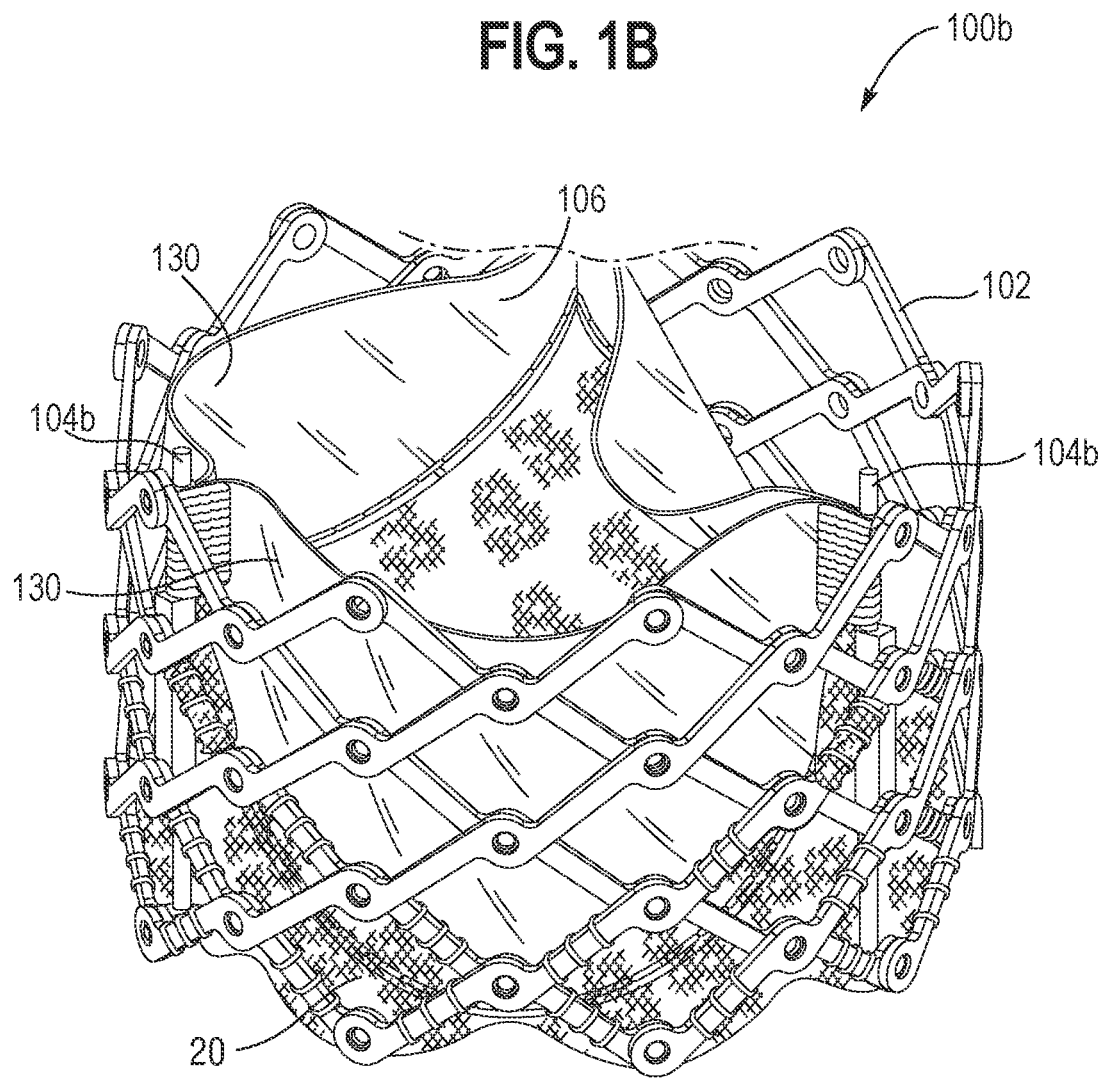

The prosthetic heart valve 100 can also include one or more skirts or sealing members. For example, the prosthetic heart valve 100 can include an inner skirt mounted on the inner surface of the frame 102 (e.g., similar to inner skirt 20 in the exemplary valve 100b of FIG. 1B) and/or an outer skirt mounted on the outer surface of the frame 102 (not shown in FIGS. 1A-1B). The inner skirt 20 can be a circumferential inner skirt that spans an entire circumference of the inner surface of the frame 102. The inner skirt 20 can function as a sealing member to prevent or decrease perivalvular leakage (e.g., when the valve is placed at the implantation site) and as an attachment surface to anchor a portion of the leaflets 130 to the frame 102. In particular embodiments, the cusp edge portions 134 of the leaflets can be sutured to the inner skirt 20, which in turn can be sutured to selected struts of the frame. Besides provision of inner skirt 20 and a different configuration for actuators 104b, the prosthetic heart valve 100b of FIG. 1B can be substantially similar to prosthetic heart valve 100 of FIG. 1A.

The outer skirt can function as a sealing member by sealing against the tissue of the native valve annulus and helping to reduce paravalvular leakage past the prosthetic valve 100. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame. Further details regarding the inner and outer skirts and techniques for assembling the leaflets to the inner skirt and assembling the skirts on the frame are disclosed in U.S. Patent Application Publication No. 2019/0192296 and International Publication Nos. WO/2020/159783 and WO/2020/198273, each of which is incorporated herein by reference.

As shown in FIG. 1A, frame 102 can include a plurality of interconnected struts arranged in a lattice-type pattern. The struts are shown as positioned diagonally, or offset at an angle relative to, and radially offset from, a longitudinal axis of the prosthetic heart valve 100 when the prosthetic heart valve 100 is in the expanded configuration. In other implementations, the struts can be offset by a different amount than depicted in FIG. 1A, or some or all of the struts can be positioned parallel to the longitudinal axis of the prosthetic heart valve 100. In the embodiment illustrated in FIG. 1A, the struts are pivotably coupled to one another at one or more pivot joints along the length of each strut. For example, each of the struts can be formed with apertures at opposing ends of the strut and apertures spaced along the length of the strut. Respective hinges can be formed at the locations where struts overlap each other via fasteners or pivot members, such as rivets or pins that extend through the apertures. The hinges can allow the struts to pivot relative to one another as the frame 102 is radially expanded or compressed, such as during assembly, preparation, or implantation of the prosthetic heart valve 100.

In some embodiments, the frame 102, or components thereof (e.g., struts and/or fasteners), can be made of any of various suitable plastically-expandable materials (e.g., stainless steel, etc.) or self-expanding materials (e.g., nickel titanium alloy (NiTi), such as Nitinol), as known in the art. In such configurations, Suitable plastically-expandable materials that can be used to form the frame 102 include, without limitation, stainless steel, biocompatible high-strength alloys (e.g., a cobalt-chromium or a nickel-cobaltchromium alloys), polymers, or combinations thereof. In particular embodiments, frame 102 is made of a nickel-cobalt-chromium-molybdenum alloy, such as MP35NR alloy (SPS Technologies, Jenkintown, Pennsylvania), which is equivalent to UNS R30035 alloy (covered by ASTM F562-02). MP35NR alloy/UNS R30035 alloy comprises 35% nickel, 35% cobalt, 20% chromium, and 10% molybdenum, by weight. When constructed of a plastically-expandable material, the frame 102 (and thus the prosthetic valve 100) can be crimped to a radially collapsed configuration on a delivery catheter and then expanded inside a patient by an inflatable balloon or equivalent expansion mechanism. Details of exemplary delivery apparatuses that can be used to deliver and implant plastically-expandable prosthetic valves are disclosed in U.S. Pat. Nos. 9,339,384, 10,076,638, and 10,588,744, all of which are incorporated herein by reference. When constructed of a self-expandable material, the frame 102 (and thus the prosthetic valve 100) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size. Details of exemplary delivery apparatuses that can be used to deliver and implant self-expandable prosthetic valves are disclosed in U.S. Pat. Nos. 8,652,202 and 9,867,700, both of which are incorporated herein by reference.

In some embodiments, the frame 102 can be constructed by forming individual components (e.g., the struts and fasteners of the frame) and then mechanically assembling and connecting the individual components together. In other embodiments, the struts are not coupled to each other with respective hinges but are otherwise pivotable or bendable relative to each other to permit radial expansion and contraction of the frame 102. For example, the frame 102 can be formed (e.g., via laser cutting, electroforming or physical vapor deposition) from a single piece of material (e.g., a metal tube). Further details regarding the construction of the frame 102 and the prosthetic heart valve 100 are described in U.S. Pat. Nos. 10,603,165 and 10,806,573, U.S. Patent Application Publication Nos. 2018/0344456 and 2020/0188099, and International Publication No. WO/2020/081893, each of which is incorporated herein by reference.

The plurality of actuators 104 can be mounted to and disposed around an inner surface of the frame 102. The actuators 104 can be configured to apply corresponding expansion and compression forces to the frame in order to radially expand or compress the prosthetic valve. For example, the actuators 104 can be linear actuators, each of which comprises an inner member or piston and an outer member or cylinder. The inner member is pivotably coupled to a junction of the frame 102, such as at the first axial end, while the outer member is pivotably coupled to another junction of the frame closer to the second axial end. Moving the inner member proximally relative to the outer member and/or moving the outer member distally relative to the inner member can be effective to radially expand the prosthetic valve 100. Conversely, moving the inner member distally relative to the outer member and/or moving the outer member proximally relative to the inner member can be effective to radially compress the prosthetic valve 100. The actuators 104 can include locking mechanisms that are configured to retain the prosthetic valve in an expanded state inside the patient's body. In alternative embodiments, the actuators can be screw type actuators that comprise, for example, a rotatable inner member coupled to an outer member via one or more threads. Rotation of the inner member relative to the outer member produces relative axial movement between the inner and outer members and corresponding radial expansion or compression of the frame.

In some embodiments, each of the actuators 104 can be configured to form a releasable connection with one or more respective actuators of a delivery apparatus of a transcatheter delivery system. The actuators of the delivery apparatus can transmit forces from a handle of the delivery apparatus to the actuators 104 for expanding or compressing the prosthetic valve. Further details of the actuators, locking mechanisms and delivery apparatuses for actuating the actuators can be found in U.S. Pat. Nos. 10,603,165 and 10,806,573, and U.S. Patent Application Publication No. 2018/0325665, each of which is incorporated herein by reference. Any of the actuators and locking mechanisms disclosed in the previously filed patents/applications can be incorporated in any of the prosthetic valves disclosed herein. Further, any of the delivery apparatuses disclosed in the previously filed patents/applications can be used to deliver and implant any of the prosthetic valves discloses herein.

Figure 21A:
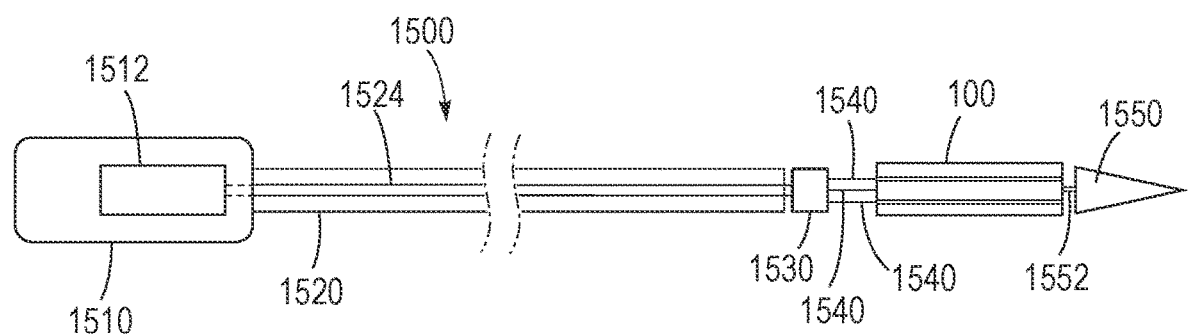
FIG. 21A shows an exemplary prosthetic valve delivery apparatus that can be used for implanting the prosthetic heart valve of FIG. 1A, according to one or more embodiments of the disclosed subject matter.
Figure 21B:
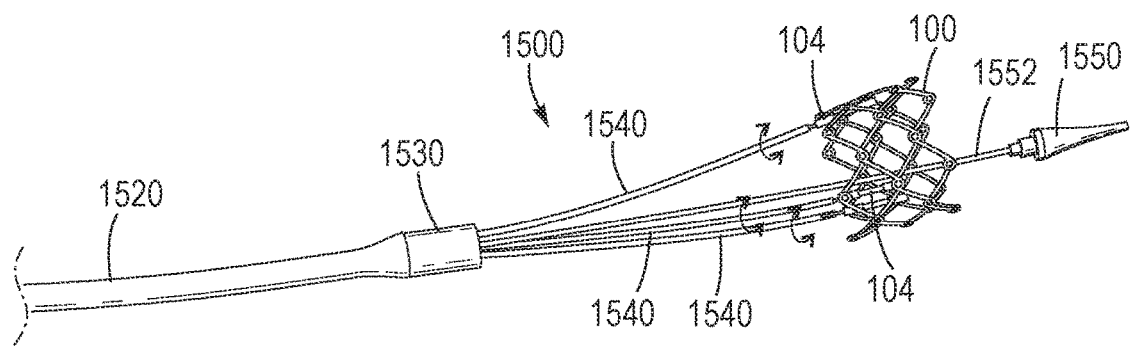
FIG. 21B shows a perspective view of the distal end portion of the delivery apparatus of FIG. 21A with the prosthetic valve of FIG. 1A in a radially-expanded state.

For example, referring to FIGS. 21A-21B, a delivery apparatus 1500 that can be used to deliver and implant a prosthetic heart valve, such as prosthetic heart valve 100 or prosthetic heart valve 100b, in the heart of a patient. The delivery apparatus 1500 can have a handle 1510, an outer elongated shaft 1520 (also referred to as a catheter) extending distally from the handle 1510, an input torque shaft 1524 extending distally from the handle 1510 through the outer shaft 1520, a gear mechanism 1530 (e.g., a gearbox) operatively connected to a distal end portion of the input torque shaft 1524, a plurality of output torque shafts 1540, and a nose cone 1550. The nose cone 1550 can be mounted on the distal end portion of an innermost shaft 1552 that serves as a guidewire lumen, which can extend coaxially through the input torque shaft 1524 and can have a proximal end portion coupled to the handle 1510.

A guidewire can extend through the guidewire lumen, and a distal end of the delivery apparatus can be advanced over the guidewire to the implant location. Each output torque shaft 1540 can have a proximal end portion connected to the gear mechanism 1530 and a distal end portion releasably connected to a respective screw of actuator 104. Each output torque shaft 1540 can have, for example, a rod, a rigid tube, a cable, a laser cut tube, a hypotube, or any other elongated annular structure (e.g., any tubular or cylindrical structure). A proximal end portion of the input torque shaft 1524 can be operatively connected to an actuator, such as a motor 1512, housed within or coupled to the handle 1510. The motor 1512 can be, for example, an electric motor powered by batteries, which can also be housed within the handle 1510. Alternatively, the motor 1512 can be a hydraulically-driven or a pneumatically-driven motor. The motor 1512 can be operable to actuate or rotate the input torque shaft 1524, which in turn actuates or rotates the output torque shafts 1540 via the gear mechanism 1530, which in turn actuates the prosthetic heart valve to radially expand or compress. Further details regarding construction and operation of a delivery apparatus for delivering and implanting a prosthetic heart valve can be found in U.S. Pat. Nos. 9,827,093, 10,076,638, and 10,806,573, all of which are incorporated herein by reference.

Figure 22:
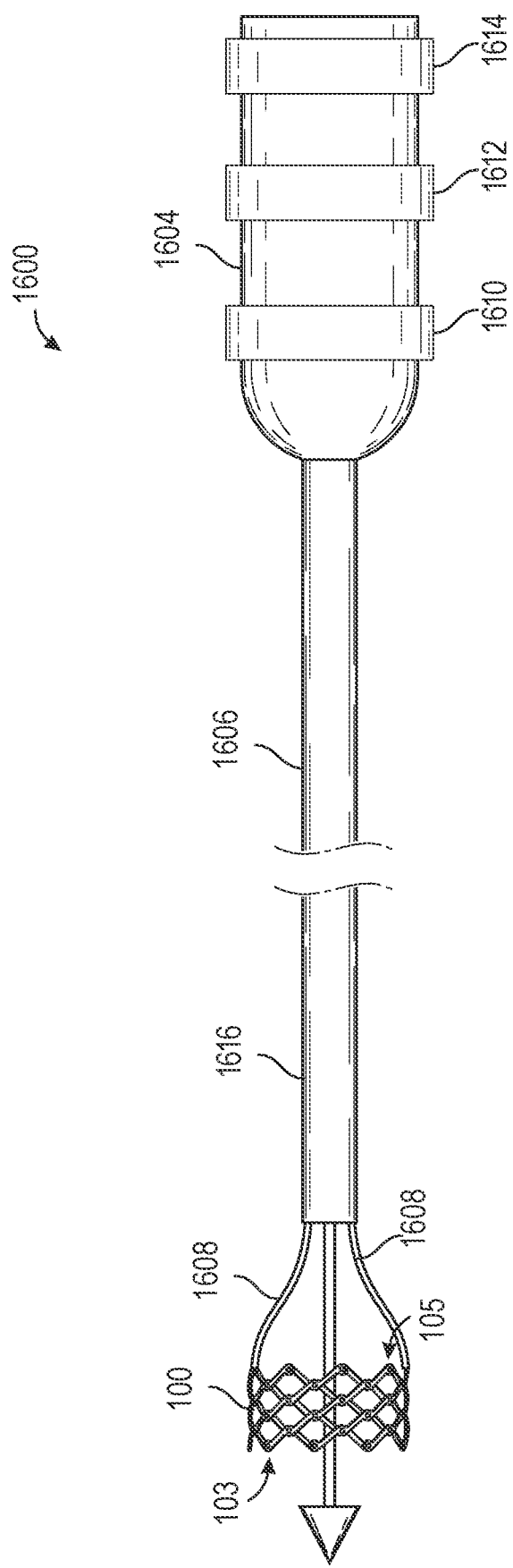
FIG. 22 shows another exemplary prosthetic valve delivery apparatus that can be used for implanting the prosthetic heart valve of FIG. 1A, according to one or more embodiments of the disclosed subject matter.

FIG. 22 illustrates another exemplary delivery apparatus 1600 adapted to deliver a prosthetic heart valve, such as prosthetic heart valve 100 or 100b described herein. The prosthetic valve 100 can be releasably coupled to the delivery apparatus 1600, such as via a removable coupling between a distal member of an expansion and locking mechanism of the prosthetic valve 100 and a second actuation member of an actuation assembly of the delivery apparatus 1600. The prosthetic valve 100 can include a distal end 103 and a proximal end 105, wherein the proximal end 105 is positioned closer to a handle 1604 of the delivery apparatus 1600 than the distal end 103, and wherein the distal end 103 is positioned farther from the handle 1604 than the proximal end 105. It should be understood that the delivery apparatus 1600 and other delivery apparatuses disclosed herein can be used to implant prosthetic devices other than prosthetic valves, such as stents or grafts.

The delivery apparatus 1600 in the illustrated embodiment generally includes the handle 1604, a first elongated shaft 1606 (which comprises an outer shaft in the illustrated embodiment) extending distally from the handle 1604, at least one actuator assembly 1608 extending distally through the outer shaft 1606. In some embodiments, a distal end portion 1616 of the shaft 1606 can be sized to house the prosthetic valve in its radially compressed, delivery state during delivery of the prosthetic valve through the patient's vasculature. In this manner, the distal end portion 1616 functions as a delivery sheath or capsule for the prosthetic valve during delivery.

The at least one actuator assembly 1608 can be configured to radially expand and/or radially collapse the prosthetic valve 100 when actuated, and may be removably coupled to the prosthetic heart valve 100. Although the illustrated embodiment shows two actuator assemblies 1608 for purposes of illustration, it should be understood that one actuator 1608 can be provided for each actuator of the prosthetic valve. For example, three actuator assemblies 1608 can be provided for a prosthetic valve having three actuators. In other embodiments, a greater or fewer number of actuator assemblies can be present. The actuator assemblies 1608 can be releasably coupled to the prosthetic valve 100. For example, in the illustrated embodiment, each actuator assembly 1608 can be coupled to a respective actuator of the prosthetic valve 100. Each actuator assembly 1608 can comprise a support tube or sleeve and an actuator member. In some embodiments, the actuator assembly 1608 also can include a locking tool. When actuated, the actuator assembly can transmit pushing and/or pulling forces to portions of the prosthetic valve to radially expand and collapse the prosthetic valve. The actuator assemblies 1608 can be at least partially disposed radially within, and extend axially through, one or more lumens of the outer shaft 1606. For example, the actuator assemblies 1608 can extend through a central lumen of the shaft 1606 or through separate respective lumens formed in the shaft 1606.

The handle 1604 of the delivery apparatus 1600 can include one or more control mechanisms (e.g., knobs or other actuating mechanisms) for controlling different components of the delivery apparatus 1600 in order to expand and/or deploy the prosthetic valve 100. For example, in the illustrated embodiment the handle 1604 comprises first, second, and third knobs 1610, 1612, and 1614. The first knob 1610 can be a rotatable knob configured to produce axial movement of the outer shaft 1606 relative to the prosthetic valve 100 in the distal and/or proximal directions in order to deploy the prosthetic valve from the delivery sheath 1616 once the prosthetic valve has been advanced to a location at or adjacent the desired implantation location with the patient's body. For example, rotation of the first knob 1610 in a first direction (e.g., clockwise) can retract the sheath 1616 proximally relative to the prosthetic valve 100 and rotation of the first knob 1610 in a second direction (e.g., counter-clockwise) can advance the sheath 1616 distally. In other embodiments, the first knob 1610 can be actuated by sliding or moving the knob 1610 axially, such as pulling and/or pushing the knob. In other embodiments, actuation of the first knob 1610 (rotation or sliding movement of the knob 1610) can produce axial movement of the actuator assemblies 1608 (and therefore the prosthetic valve 100) relative to the delivery sheath 1616 to advance the prosthetic valve distally from the sheath 1616.

The second knob 1612 can be a rotatable knob configured to produce radial expansion and/or contraction of the prosthetic valve 100. For example, rotation of the second knob 1612 can move the actuator member and the support tube axially relative to one another. Rotation of the second knob 1612 in a first direction (e.g., clockwise) can radially expand the prosthetic valve 100 and rotation of the second knob 1612 in a second direction (e.g., counter-clockwise) can radially collapse the prosthetic valve 100. In other embodiments, the second knob 1612 can be actuated by sliding or moving the knob 1612 axially, such as pulling and/or pushing the knob. The third knob 1614 can be a rotatable knob configured to retain the prosthetic heart valve 100 in its expanded configuration. For example, the third knob 1614 can be operatively connected to a proximal end portion of the locking tool of each actuator assembly 1608. Rotation of the third knob in a first direction (e.g., clockwise) can rotate each locking tool to advance the locking nuts to their distal positions to resist radial compression of the frame of the prosthetic valve. Rotation of the knob 1614 in the opposite direction (e.g., counterclockwise) can rotate each locking tool in the opposite direction to decouple each locking tool from the prosthetic valve 100. In other embodiments, the third knob 1614 can be actuated by sliding or moving the third knob 1614 axially, such as pulling and/or pushing the knob. Although not shown, in some embodiments, the handle 1604 can include a fourth rotatable knob operative connected to a proximal end portion of each actuator member. The fourth knob can be configured to rotate each actuator member, upon rotation of the knob, to unscrew each actuator member from the proximal portion of a respective actuator. Once the locking tools and the actuator members are uncoupled from the prosthetic valve 100, they can be removed from the patient.

Figure 2:
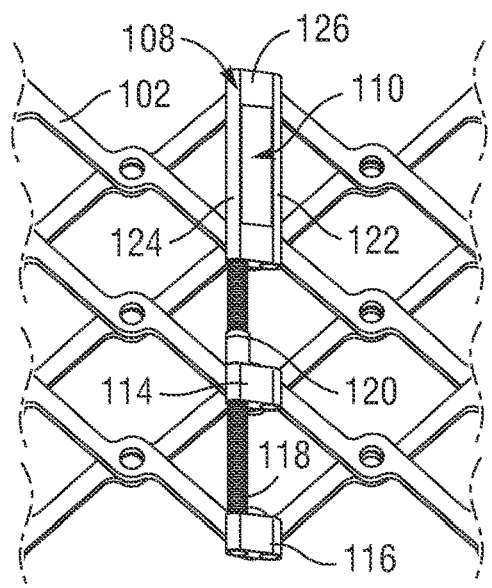
FIG. 2 is a detail view of an actuator and an interior side of the frame of the prosthetic heart valve of FIG. 1A.
Figure 4:
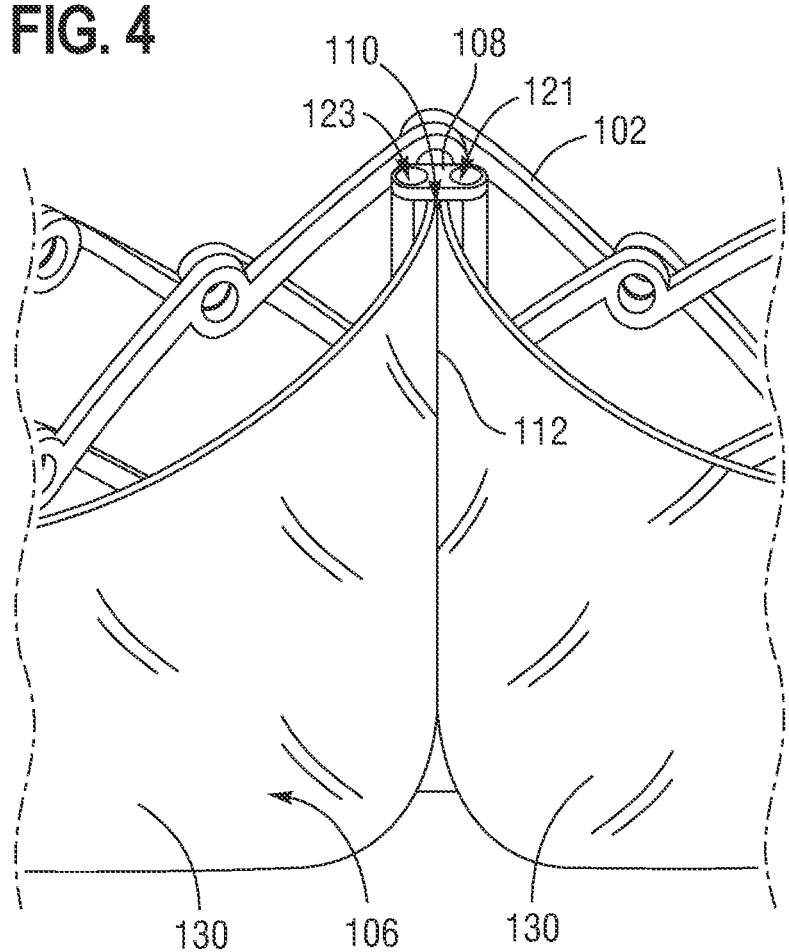
FIG. 4 is a magnified detail view showing an exemplary attachment of a commissure assembly to the frame of the prosthetic heart valve of FIG. 1A, according to one or more embodiments of the disclosed subject matter.

The tabs 132 of adjacent leaflets 130 can be arranged together to form commissures 112 (also referred to herein as commissure tab assemblies) that can be coupled to respective commissure support posts, thereby securing at least a portion of the leaflet assembly to the frame 102. In some embodiments, each of the actuators 104 can be used to support a respective commissure 112 (described below). As such, the actuators 104 can include commissure support posts (also referred to herein as commissure post or support member) for supporting and securing commissures 112 of the valvular structure 106 to the frame 102. In some embodiments, the proximal support members 108 of the actuators 104 comprise windows 110 configured to receive commissures 112 of the valvular structure 106, as shown in FIGS. 2 and 4. Alternatively or additionally, the frame 102 of the heart valve 100 can include commissure support posts as separate structures from the actuators 104. For example, the commissures 112 can be mounted to support members that are support struts or posts of the frame 102 that are separate from the actuators 104. In some embodiments, the commissure support posts (or a subsection thereof to which the commissures 112 are coupled) may be substantially aligned with, or extend along a direction substantially parallel to, the longitudinal axis of the frame 102.

As shown in FIGS. 2 and 4, a proximal support member 108 of one or more of the actuators 104 has a window 110 configured to receive leaflet commissures 112 of the valvular structure 106. For example, one or more of the actuators 104 of the prosthetic valve 100 can comprise a proximal support member 108, an intermediate support member 114, a distal support member 116, a locking member 118, and a locking nut 120. The support members 108, 114, 116 can each have an actuation lumen 121 and a locking lumen 123. The actuation lumens 121 can be configured for receiving an actuation shaft of a delivery apparatus. The actuation shaft can be releasably connected to the support member 116 and an outer support tube of the delivery apparatus can abut the upper end of the support member 108 such that axial movement of the actuation shaft in a proximal direction is effective to radially expand the frame. The locking lumens 123 can be configured for receiving the locking member 118 and a locking shaft of a delivery apparatus. The proximal support member 108 of actuator 104 can comprise an actuation tube 122, a locking tube 124, and one or more connection portions 126 (e.g., two illustrated in FIG. 2). The actuation lumen 121 can extend axially through the actuation tube 122, and the locking lumen 123 can extend axially through the locking tube 124. The connection portions 126 can also be configured for mounting the proximal support member 108 to the frame 102 (e.g., via radially-extending support projection 202, illustrated in FIG. 5A). Further details of the actuators and delivery apparatuses for actuating the actuators can be found in International Application No. PCT/US2020/040318, filed Jun. 30, 2020 and U.S. Provisional Application No. 62/869,948, filed Jul. 2, 2019, each of which is incorporated herein by reference.

The tubes 122, 124 can be spaced apart from each other, and the connection portions 126 can be disposed at the proximal and/or distal end portions of the tubes 122, 124 and extend therebetween. The tubes 122, 124 and the connection portions 126 can thus define a window 110. In particular, the tubes 122, 124 and the connections portions 126 define a passage radially extending through support member 108 that is closed at opposite axial ends, such that window 110 may be considered a closed window. As shown in FIG. 4, the closed window 110 can be configured to receive the commissures 112 of the valvular structure 106. For example, the commissures 112 can be assembled and a commissure tab assembly of the commissures passed through the window 110 outward along the radial direction of the frame 102 in order to secure the commissure 112 to the frame 102.

In some embodiments, attachment of the commissure tab assembly to the respective closed window of the support member can be achieved by a wedge element inserted into the commissure tab assembly once it has passed to the radially-outer side of the window. The wedge element can increase a width of the tab assembly such that the tab assembly cannot pass back through the window.

For example, FIGS. 5A-5D illustrate a first exemplary method of installing a commissure tab assembly 212 to a support member 208 of an actuator 204 using a wedge element 236. In alternative embodiments, the support member 208 need not be a component of actuator. In some embodiments, for example, a prosthetic valve can have support members 208 (one for each commissure) mounted to an inner surface of the frame separate from any actuators that the prosthetic valve may have. In other embodiments, a prosthetic valve can have support members 208 (one for each commissure) that are integral components of the frame, such as disclosed in U.S. Pat. No. 9,393,110, which is incorporated herein by reference. Thus, it should be understood that any commissure assembly and assembly method therefor disclosed herein can be use in a prosthetic valve having support members that are portions of actuators, separate components from the actuators, or integral components of the frame. Further, although certain illustrated embodiments of commissure assemblies are disclosed for mechanically expandable prosthetic valves, any of the disclosed embodiments can be implemented in balloon-expandable prosthetic valves, such as disclosed in U.S. Pat. No. 9,393,110, or self-expandable prosthetic valves, such as disclosed in U.S. Pat. No. 8,652,202, each of which is incorporated herein by reference.

Figure 5A:
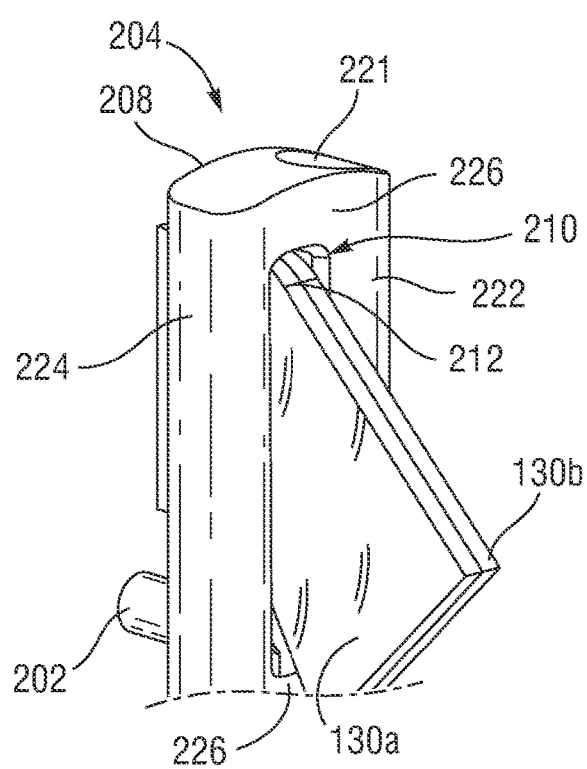
FIG. 5A is a perspective view of a first example for assembling a commissure tab assembly to a closed window of a support.

Referring to FIG. 5A, the closed window 210 of the support member 208 can be defined by first member 222, second member 224, and top and bottom connection portions 226. The first and second members 222, 224 can extend along an axial direction of the frame 102, while the connection portions 226 extend along a circumferential direction of the frame 102 to connect together the first and second members 222, 224 at opposite ends thereof. The bottom connection portion 226 can include a projection 202 at a radially outer side of the actuator 204. The projection 202 can couple actuator 204 to a corresponding portion of the frame 102. In some embodiments, one or both of the first and second members 222, 224 can include a respective lumen 221 (e.g., actuator lumen or locking lumen, as described above) that extends through the member along the axial direction of the frame 102. The support member 208 can have an inner side that faces radially inward to a centerline of the frame 102, and an outer side that faces in an opposite direction toward the anatomy when the valve 100 is installed within a patient.

Figure 5B:
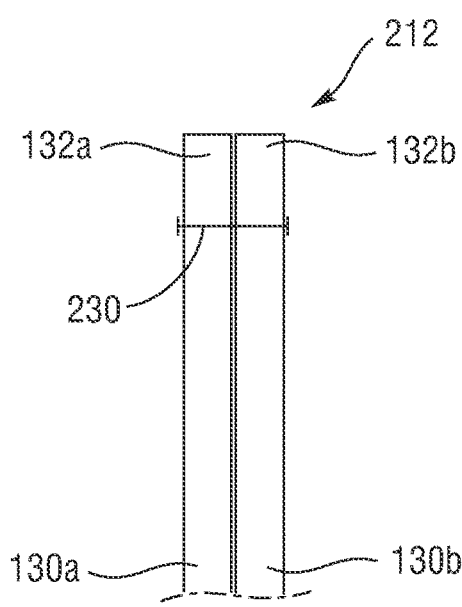
FIGS. 5B-5D are top down views illustrating sequential stages in assembling the commissure tab assembly to the closed window of the support member, according to the first example.
Figure 5C:
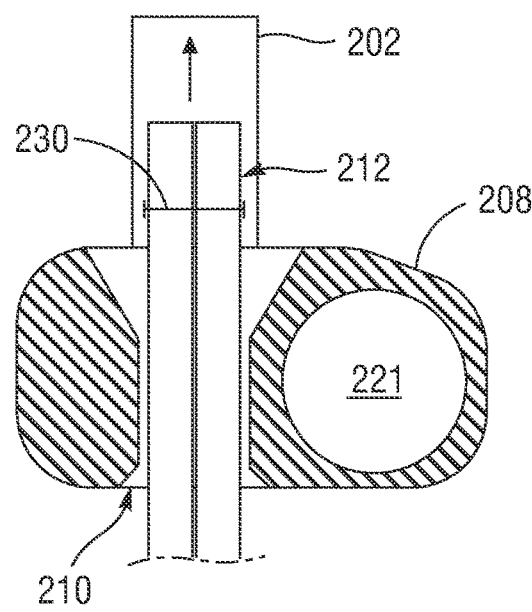
Figure 5D:
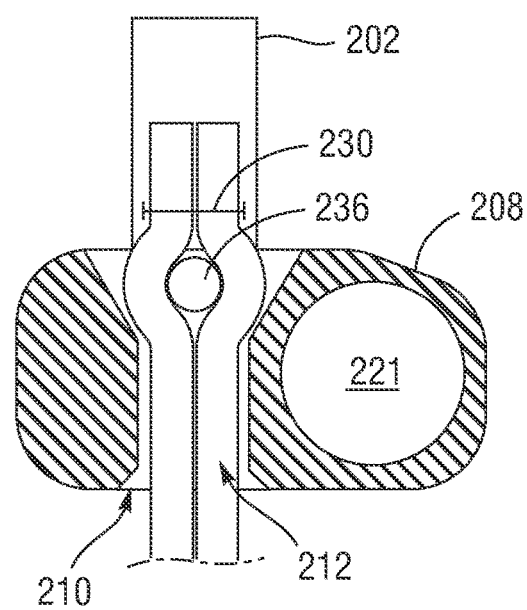

Referring to FIG. 5B, the commissure tab assembly 212 can be formed by disposing tabs 132a, 132b of adjacent leaflets 130a, 130b together. The tabs 132a, 132b can then be joined together by stitching, for example, via stitches or suture loops 230, in order to form a tail. The sutured tail may reduce the risk of the leaflet tabs of being caught between struts of the frame during valve crimping. The commissure tab assembly 212 can then be passed through a radially inner end of window 210 to extend beyond a radially outer end of window 210, as shown in FIG. 5C. Once fully inserted through window 210, a wedge element 236 can be inserted between the tabs of the commissure tab assembly 212, as shown in FIG. 5D.

For example, wedge element 236 can be conveyed axially with respect to the frame 102 and inserted between facing surfaces of the tabs. For example, a needle can be used to convey the wedge element 236 between the tabs. In some embodiments, suture loops 230 may be left relatively loose prior to insertion of wedge element 236, thereby providing sufficient flexibility in spacing between tabs through which the wedge element 236 can extend. In such embodiments, the suture loops 230 may be tightened once the wedge element 236 is in its final position between tabs of the commissure tab assembly 212.

The wedge element 236 can be disposed along the radial direction between the frame 102 and the support member 208, for example, between suture 230 and the radially outer end of the window 210 along the radial direction. The wedge element 236 can be any biocompatible material or structure capable of being inserted between the leaflet tabs without causing damage thereto (e.g., tearing or ripping) and without degrading when disposed in the patient. For example, the wedge element 236 can be formed from a relatively thick polymer suture or cable (e.g., a braided suture, such as an Ethibond suture or a monofilament suture), a piece of cloth or fabric (which can be folded one or more times to increase its thickness), or any other structure.

The wedge element can be sized/shaped so as to increase a width of a portion the commissure tab assembly 212 along a circumferential direction of the frame 102. This increased width portion of the commissure tab assembly 212 due to the inserted wedge element 236 may be greater than a width of the radially outer end of window 210, such that the commissure tab assembly 212 is prevented, or at least restrained, from passing back through window 210 (e.g., radially inward toward a centerline of the frame 102) by interaction between the increased width portion of commissure tab assembly 212 and window 210.

Installing the commissures tab assembly 212 of the leaflets 130a, 130b to the support member 208 in this manner can provide several advantages. For example, the configuration illustrated in FIGS. 5A-5D can allow a significant portion of the commissure tab assembly 212 to be pre-assembled prior to attachment to the frame 102. Attachment of the assembly 212 to the frame 102 may be relatively simple, involving only wedge element 236 insertion as opposed to suturing of the assembly 212 to the support member 208 in the narrow region between support member 208 and the surrounding frame 102. In some embodiments, no sutures are used to attach the commissure tab assembly to the support member 208, and in particular, there are no sutures that extend through the commissure tab assembly and around the support member or through openings or slots in the support member. Moreover, in some embodiments, no sutures are used for further assembly of the commissure tab assembly after the commissure tab assembly is inserted through the window 210. Instead, the commissure tab assembly is fixed against movement in a radial inward direction by virtue of the wedge element sized larger than the width of the window 210 and fixed against movement in an axial direction by upper and lower connecting portions 226.

In some embodiments, the commissure tab assembly can have a coupling member, such as a flexible cloth or fabric, disposed around external surfaces of the leaflet tabs. The coupling member can be attached to the commissure tab assembly prior to passing through the closed window of the support member. Once inserted into the closed window, a wedge element can be inserted into the commissure tab assembly at the radially-outer side of the window, thereby increasing a width of the commissure tab assembly such that the tab assembly cannot pass back through the window. The coupling member can protect portions of the leaflets from abrasion by interaction with the support member, and may assist in providing reliable attachment of tabs of the commissure tab assembly together.

Figure 6A:
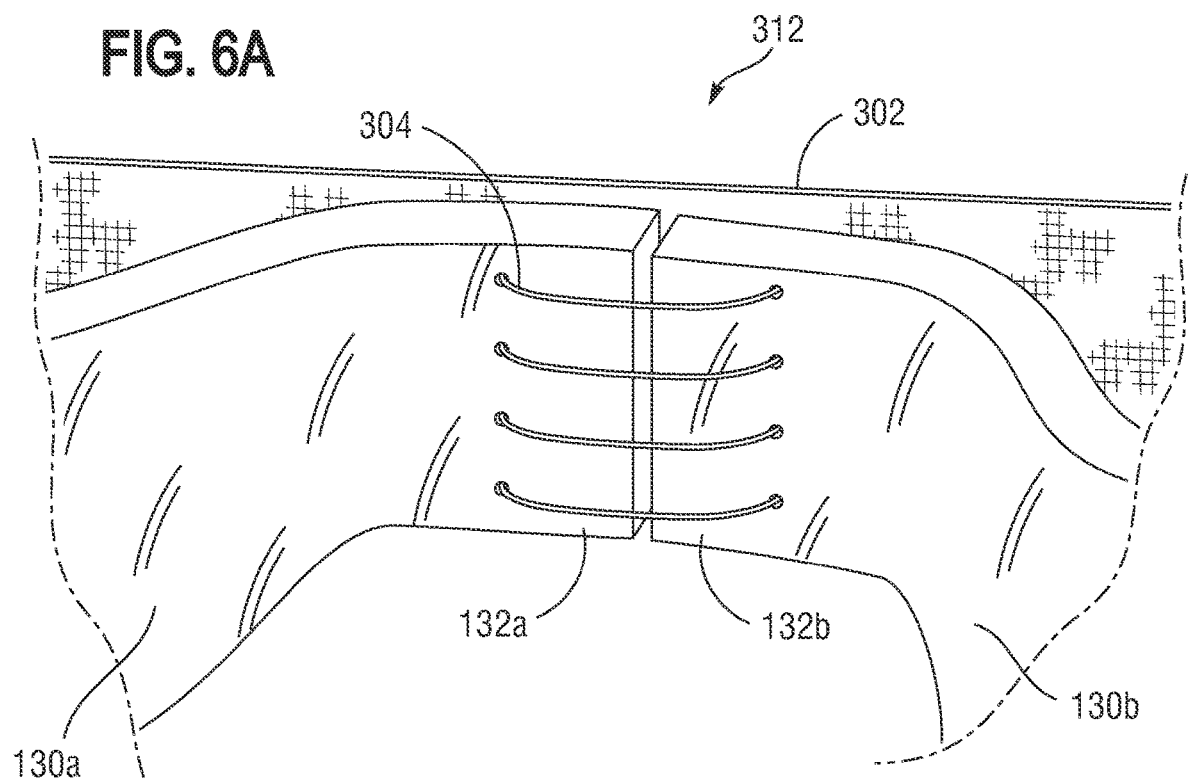
FIGS. 6A-6H are various views illustrating sequential stages in assembling a commissure tab assembly to a closed window of a support member, according to a second example.
Figure 6B:
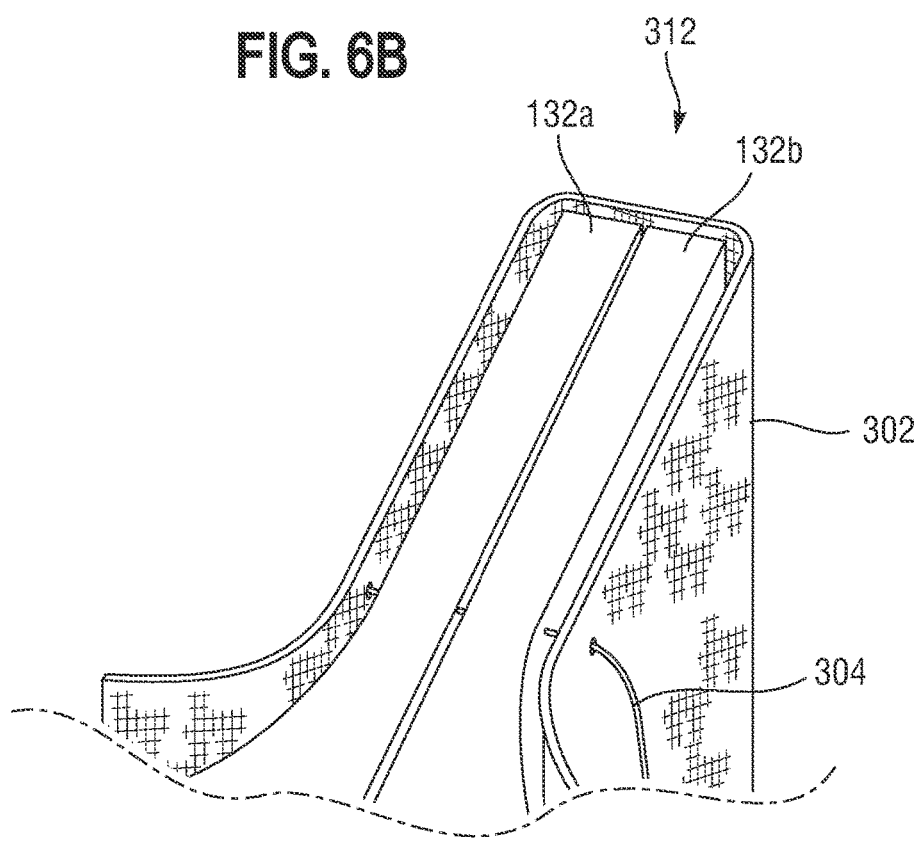

For example, FIGS. 6A-6H illustrate a second exemplary method of installing a commissure tab assembly 312 to a support member 208 using a wedge element 310. Referring initially to FIG. 6A, the commissure tab assembly 312 can be formed by disposing tabs 132a, 132b of adjacent leaflets 130a, 130b together. For example, the tabs 132a, 132b can be arranged flat with end surfaces facing each other. A coupling member 302 (also referred to as a "reinforcing member") can be disposed over first surfaces of the tabs 132a, 132b, as shown in FIG. 6A. The tabs 132a, 132b and the coupling member 302 can then be joined together by stitching, for example, via first stitches or first suture loops 304. After stitching, the tabs 132a, 132b can be rotated or flexed toward each other (e.g., about the facing end surfaces) to form the commissure tab assembly 312 illustrated in FIG. 6B.

Figure 6C:
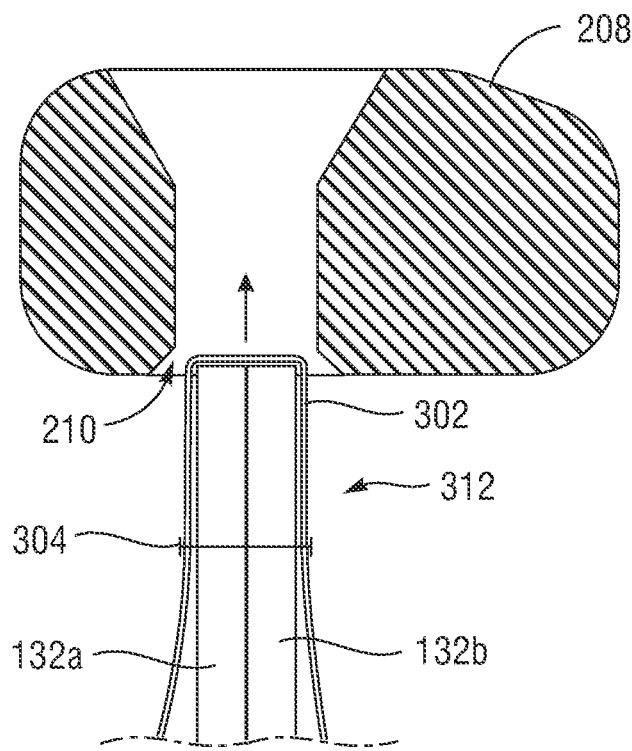
Figure 6D:
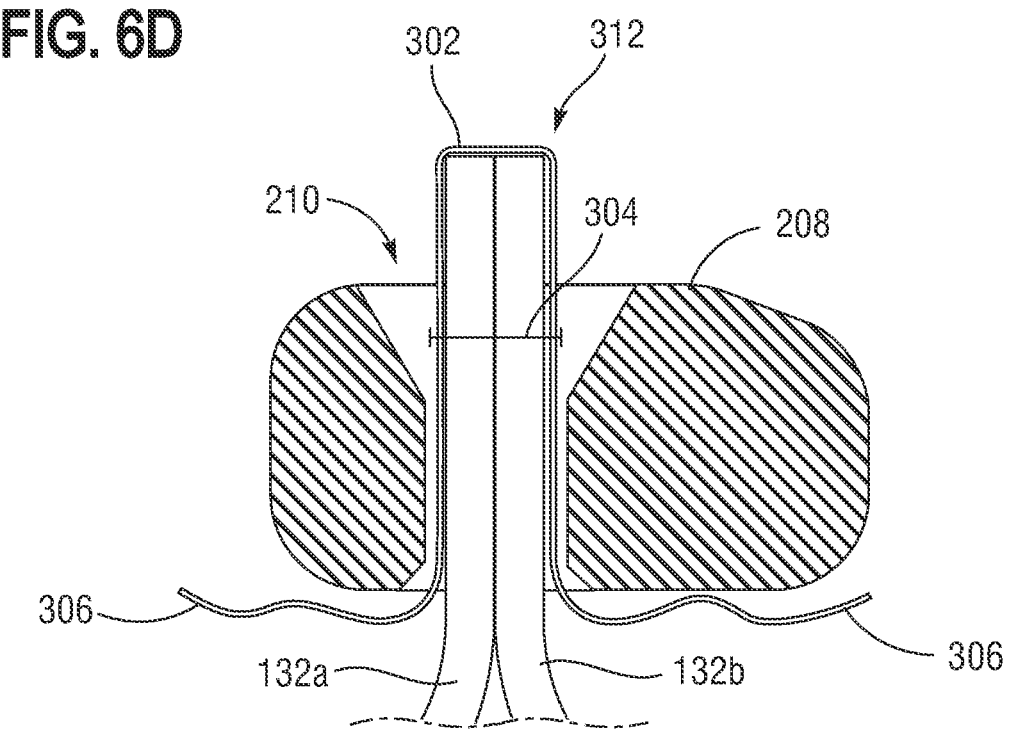
Figure 6E:
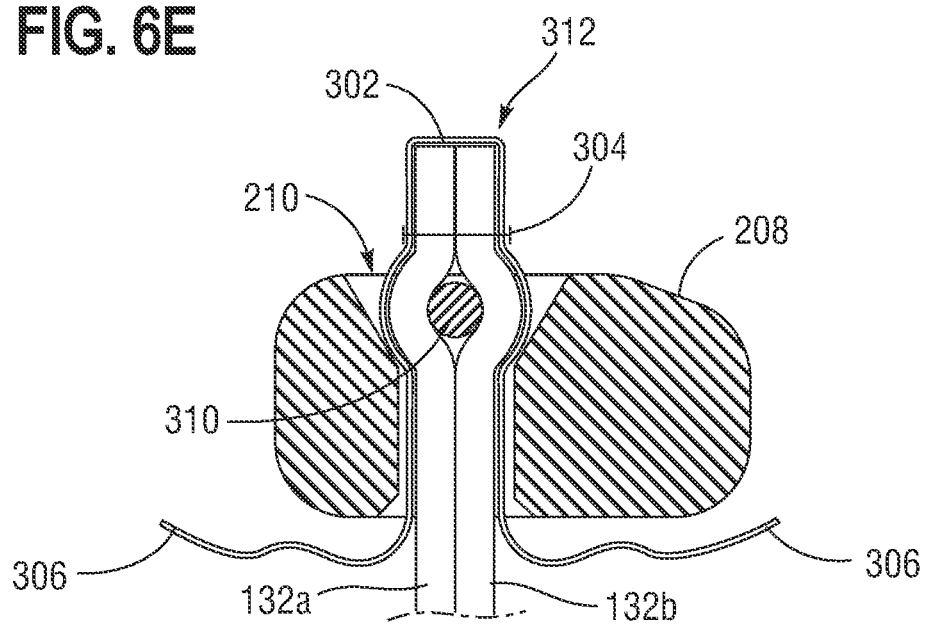

The commissure tab assembly 312, with coupling member 302, can then be passed through a radially inner end of window 210 to extend beyond a radially outer end of window 210, as shown in FIGS. 6C-6D. For example, the insertion may be such the coupling member 302 passes back through the window 210, with free ends 306 extending from the radially inner end of window 210, as shown in FIG. 6D. Once fully inserted through window 210, a wedge element 310 can be inserted between the tabs of the commissure tab assembly 312, as shown in FIG. 6E.

For example, wedge element 310 can be conveyed axially with respect to the frame 102 and inserted between facing surfaces of the tabs. For example, a needle can be used to convey the wedge element 310 between the tabs. In some embodiments, first suture loops 304 may be left relatively loose prior to insertion of wedge element 310, thereby providing sufficient flexibility in spacing between tabs through which the wedge element 310 can extend. In such embodiments, the first suture loops 304 may be tightened once the wedge element 310 is in its final position between tabs of the commissure tab assembly 312.

The wedge element 310 can be disposed along the radial direction between the frame 102 and the support member 208, for example, between first suture 304 and the radially outer end of the window 210 along the radial direction. The wedge element 310 can be any biocompatible material or structure capable of being inserted between the leaflet tabs without causing damage thereto (e.g., tearing or ripping) and without degrading when disposed in the patient. For example, the wedge element 310 can be formed from a relatively thick polymer suture or cable (e.g., polyester suture, such as Ethibond), folded piece of cloth, or any other structure.

The wedge element 310 can be sized/shaped so as to increase a width, along a circumferential direction of the frame 102, for a portion the commissure tab assembly 312. This increased width portion of the commissure tab assembly 312 due to the inserted wedge element 310 may be greater than a width of the radially outer end of window 210, such that the commissure tab assembly 312 is prevented, or at least restrained, from passing back through window 210 (e.g., radially inward toward a centerline of the frame 102) by interaction between the increased width portion of commissure tab assembly 312 and window 210.

Figure 6F:
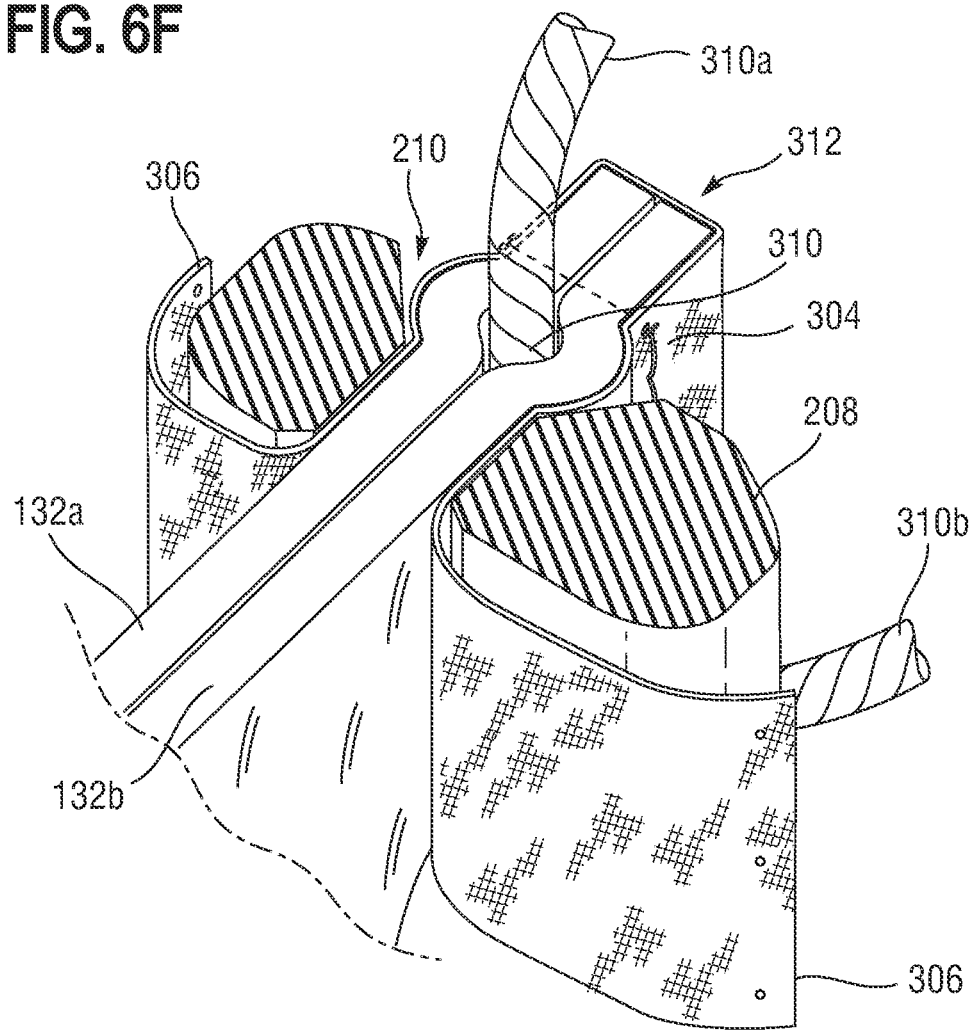

In some embodiments, the wedge element 310 can have opposite ends 310a, 310b along the radial direction that extend beyond a height of the commissure tab assembly 312 once fully inserted, for example, as illustrated in FIG. 6F. As loose ends 310a, 310b of the wedge element 310 may interfere with installation or operation of the heart valve, the loose ends 310a, 310b can be folded over and inserted into another portion of the commissure tab assembly 312. In profile, the wedge element 310 can be substantially C-shaped, with a top exposed portion of the wedge element 310 extending above the commissure tab assembly 312 being substantially U-shaped and a bottom exposed portion of the wedge element 310 extending below the commissure tab assembly 312. For example, each loose end 310a, 310b can be bent radially outward over the line of the first suture 304 and inserted into a portion of the commissure tab assembly 312 between the first suture 304 and a radially outermost end of the commissure tab assembly 312, as shown in FIGS. 6F-6H.

In some embodiments, the loose ends 310a, 310b can have a thickness or diameter less than a middle portion of wedge element 310 between the loose ends 310a, 310b, such that insertion of the loose ends 310a, 310b into the commissure tab assembly 312 does not substantially increase a thickness of the commissure tab assembly 312. Alternatively, the wedge element 310 can have a substantially constant thickness or diameter along its entire length, such that insertion of the loose ends 310a, 310b into the commissure tab assembly 312 increases the thickness of the commissure tab assembly 312 between the first suture 304 and the radially outermost end of the commissure tab assembly 312 in a similar manner as insertion of the wedge element 310 in the commissure tab assembly 312 between the first suture 304 and the support member 208.

Figure 6G:
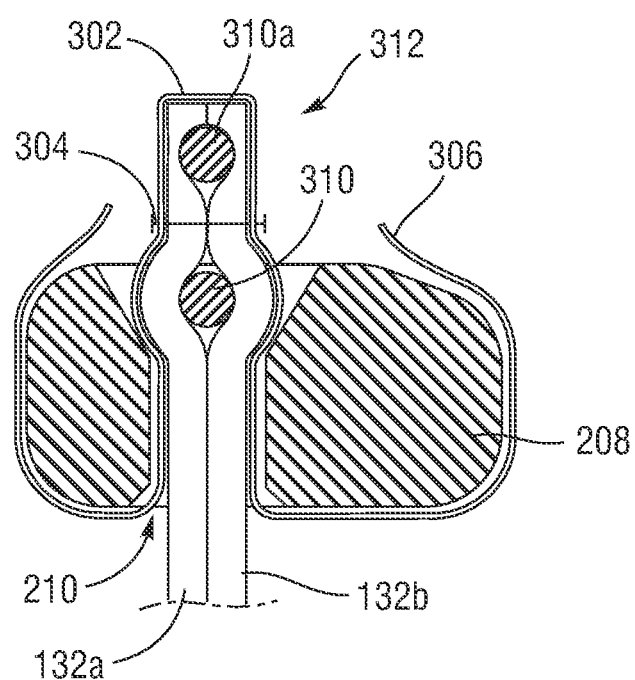
Figure 6H:
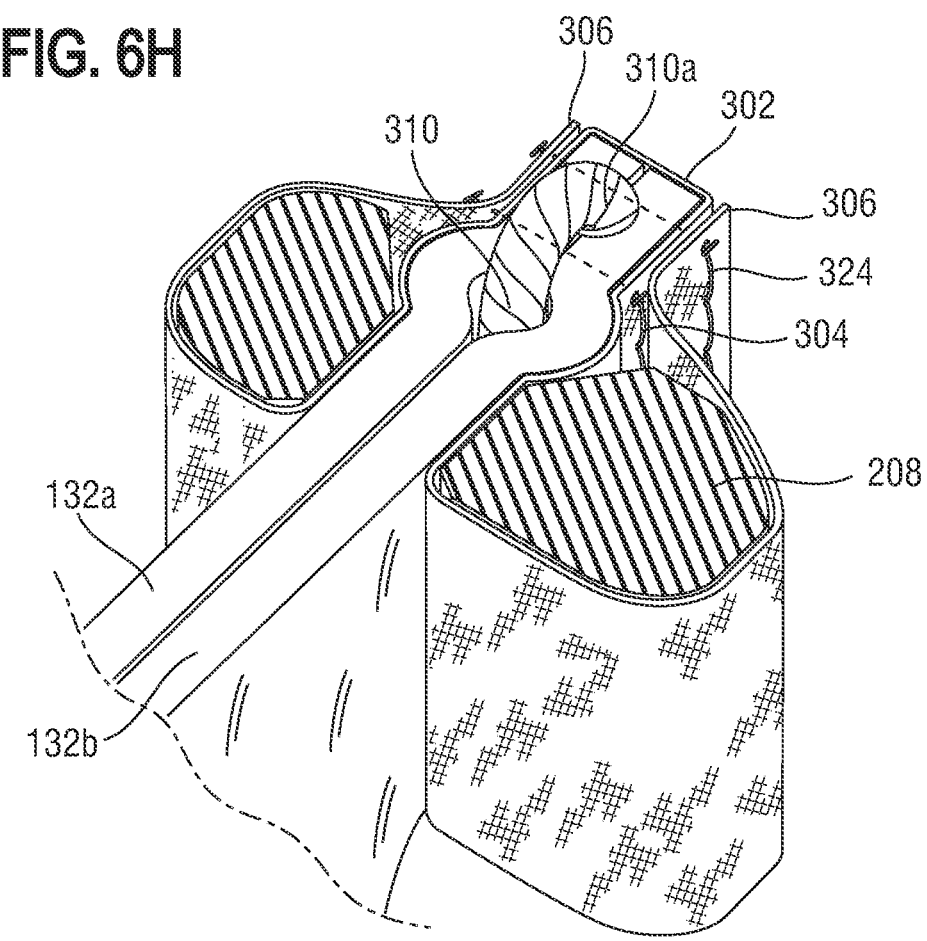

Once the commissure tab assembly 312 is fully inserted through window 210 and prior to or after insertion of wedge element 310, the free ends 306 of the coupling member 302 that extend radially inward can be wrapped around the window frame portions of the support member 208 back toward the radially outer side of the support member, as illustrated in FIGS. 6F-6H. In some embodiments, the free ends 306 of coupling member 302 can optionally be secured, for example, by stitching the free ends 306 to a radially outer end portion of the commissure tab assembly 312 via one or more second sutures 324, as illustrated in FIG. 6H. The wrapping and stitching of the coupling member 302 can further secure the commissure tab assembly 312 to the support member 208. For example, the second suture 324 may extend through a width of the commissure tab assembly 312 at a location along the radial direction between a radially outermost end of the commissure tab assembly 312 and the first suture 304.

When the loose ends 310a, 310b of wedge element 310 are further inserted into the commissure tab assembly 312, the loose ends 310a, 310b can be between the first suture 304 and the second suture 324 along the radial direction. Alternatively, the second suture 324 can pass through loose ends 310a, 310b of wedge element 310 as well as the free ends 306 of coupling member 302 to secure them to the commissure tab assembly 312. Alternatively, a third suture (not shown) is separately used to secure the loose ends 310a, 310b of wedge element 310 in their inserted position, while the second suture 324 securing the free ends 306 of the coupling member is spaced radially outward from the third suture.

Installing the commissures tab assembly 312 of the leaflets 130a, 130b to the support member 208 in this manner can provide several advantages. For example, the configuration illustrated in FIGS. 6A-6F can allow a significant portion of the commissure tab assembly 312 to be pre-assembled prior to attachment to the frame 102. Attachment of the assembly 312 to the frame 102 may be relatively simple, involving insertion of wedge element 310 and securing of the coupling member once the commissure tab assembly 312 is inserted into the support member window 210. Moreover, the coupling member 302 can serve as a protective layer between the leaflet tabs 132a, 132b and the portions of the support member 208 forming window 210.

In some embodiments, the coupling member can be disposed between the tabs of the commissure tab assembly as well as around the external surfaces of the tabs. The coupling member can be attached to the commissure tab assembly prior to passing through the closed window of the support member. Once inserted into the closed window, a wedge element can be inserted into the commissure tab assembly, for example, between facing surfaces of the coupling member that is between the tabs. The wedge element can be inserted into the commissure tab assembly at the radially-outer side of the window, thereby increasing a width of the commissure tab assembly such that the tab assembly cannot pass back through the window. The coupling member can thus protect portions of the leaflets from abrasion by interaction with the support member as well as protect portions of the tabs from abrasion with the wedge element.

Figure 7A:
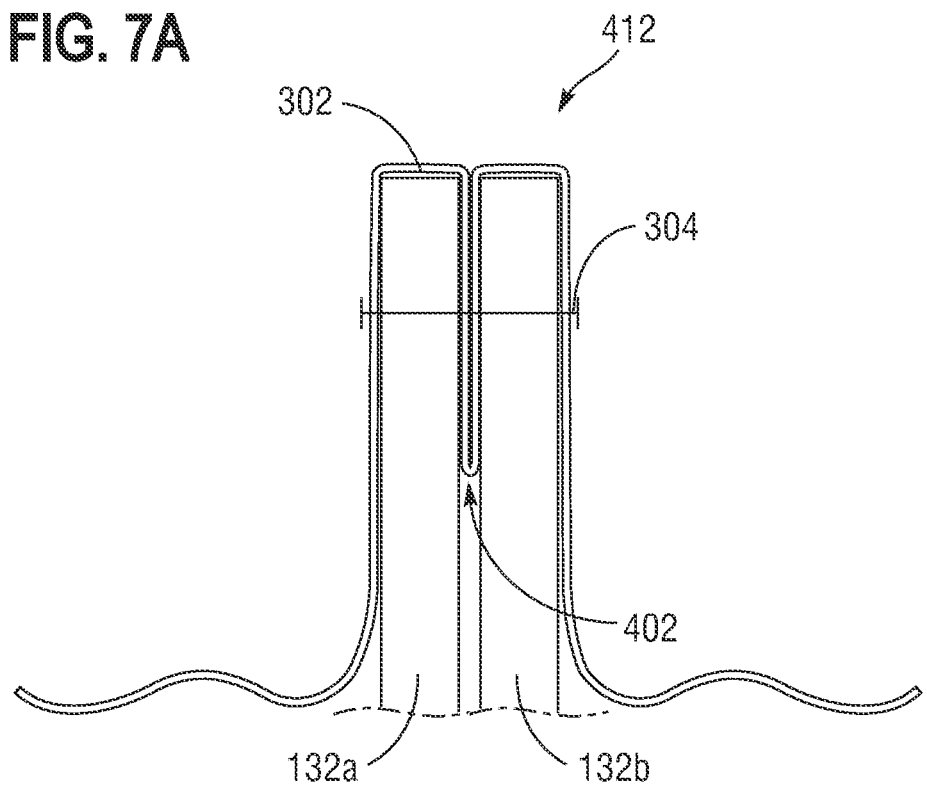
Figure 7B:
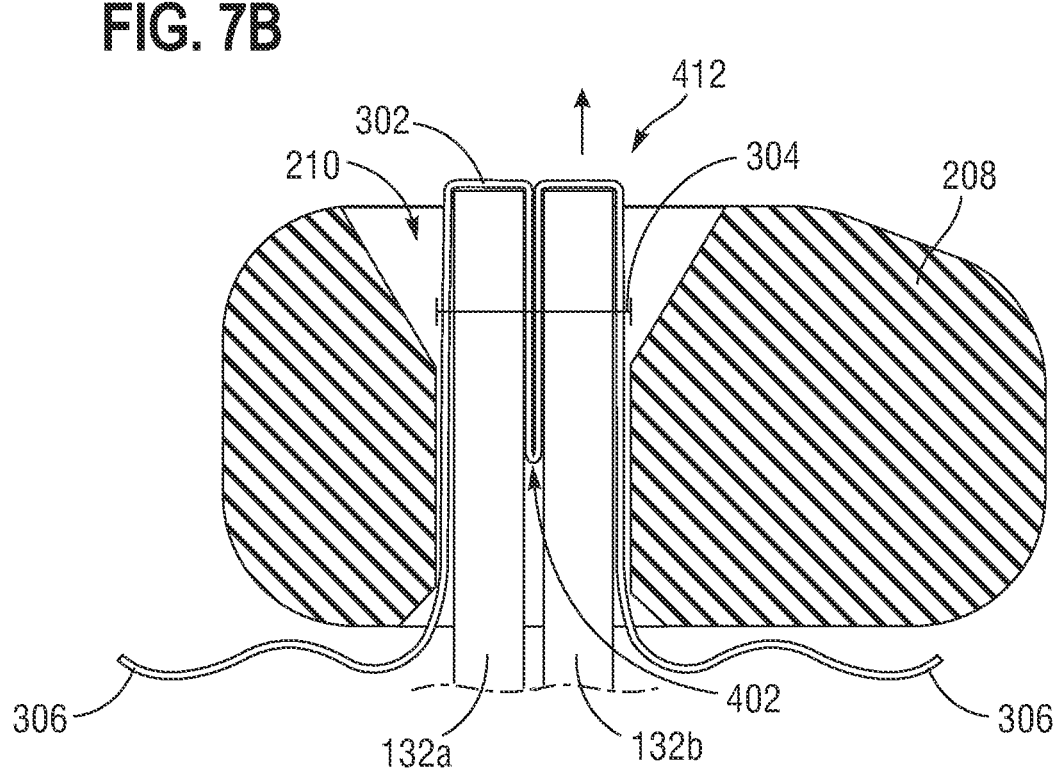

For example, FIGS. 7A-7C illustrate a third exemplary method of installing a commissure tab assembly 412 to a support member 208 using a wedge element 310. The third exemplary method of FIGS. 7A-7C may be similar in many respects to the second exemplary method of FIGS. 6A-6F. However, coupling member 302 is disposed between facing surfaces of adjacent tabs 132a, 132b as well as over the external surfaces of the tabs, as illustrated in FIG. 7A. For example, the leaflet tabs 132a, 132b can be disposed adjacent to each other and then flexed in opposite directions to form a T-shape. The coupling member 302 can then be disposed over the surfaces of the leaflet tabs 132, 132b, after which the tabs can be straightened. The coupling member 302 can thus form a folded portion or collapsed internal pocket 402 between the tabs 132a, 132b. The tabs 132a, 132b and the coupling member 302 can then be joined together by stitching, for example, via first stitches or first suture loops 304, to form commissure tab assembly 412.

The commissure tab assembly 412, with coupling member 302, can then be passed through a radially inner end of window 210 to extend beyond a radially outer end of window 210, as shown in FIGS. 7B-7C. For example, the insertion may be such the coupling member 302 passes back through the window 210, with free ends 306 extending from the radially inner end of window 210, as shown in FIG. 7B. Once fully inserted through window 210, a wedge element 310 can be inserted into the pocket 402 formed by coupling member 302 between the tabs of the commissure tab assembly 312, as shown in FIG. 7C.

Details regarding the wedge element 310 (e.g., method of insertion, location of insertion, material composition, handling of loose ends 310a, 310b, etc.), wrapping and securing free ends 306 of the coupling member 302, and/or other details of the third assembly method may otherwise be similar to that described above for the second assembly method in FIGS. 6A-6F. Thus, the third assembly method may offer advantages similar to those offered by the second assembly method. Moreover, the location of the coupling member 302 between the wedge element 310 and the tabs 132a, 132b may further protect the tabs from damage.

In some embodiments, the wedge element or multiple wedge elements can be disposed outside the tabs (e.g., with the tabs therebetween along a circumferential direction of the frame) rather than between the tabs. To allow the wedge element and commissure tab assembly to pass through the closed window, a suture retaining the coupling member to the tabs can be left in a loose state such that the coupling member extends beyond an end of the tabs. The wedge element can be inserted between the coupling member and the suture at a location spaced from the end of the tabs. The coupling member and wedge element can then be inserted through the window first, followed by the tabs of the commissure tab assembly. Once inserted into the closed window, the suture can be tightened, thereby pulling the coupling member and wedge element into contact with the tabs. The wedge element can thus effectively increase a width of the commissure tab assembly such that the tab assembly cannot pass back through the window. The location of the wedge element outside the coupling member can insulate the tabs from potential damage due to interaction with the wedge element.

Figure 8A:
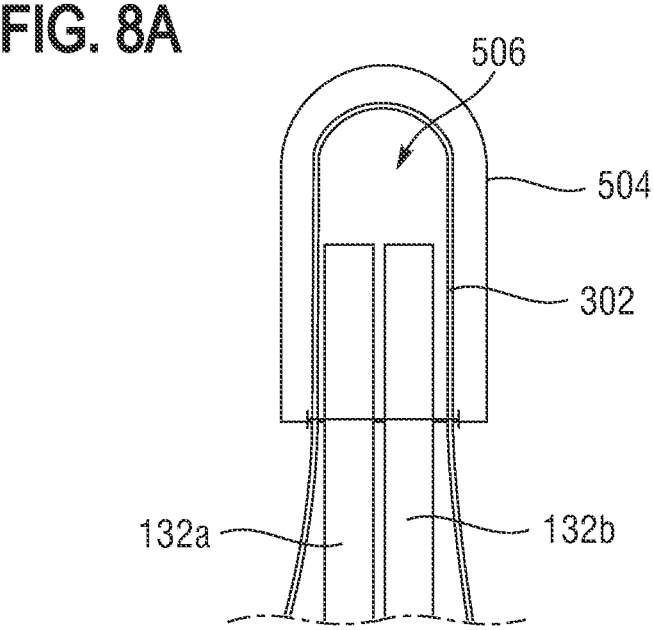
FIGS. 8A-8D are various views illustrating sequential stages in assembling a commissure tab assembly to a closed window of a support member, according to a fourth example.

For example, FIGS. 8A-8D illustrate a fourth exemplary method of installing a commissure tab assembly to a support member 208 using a wedge element 502. Referring initially to FIG. 8A, an initial assembly, comprised of adjacent tabs 132a, 132b and coupling member 302, can be formed in a manner similar to that described above with respect to FIGS. 6A-6B. However, the one or more first sutures 504 that stitch the coupling member 302 and the tabs 132a, 132b is left in a loose state, such that coupling member 302 can be pulled from the ends of the tabs 132a, 132b to form a collapsible external pocket 506.

Figure 8B:
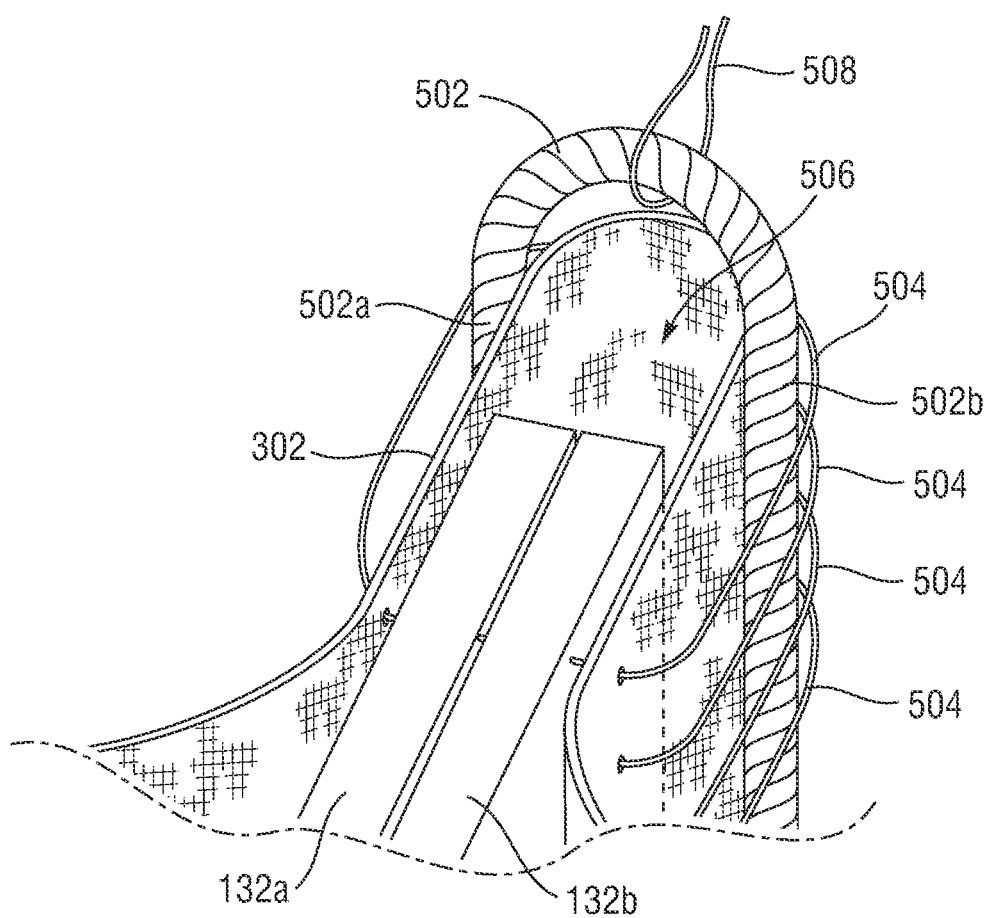

A wedge element 502 can be positioned over external surfaces of the collapsible pocket 506 formed by the coupling member 302, between the loose sutures 504 and the coupling member 302, as illustrated in FIG. 8B. For example, the wedge element 502 can be a substantially U-shaped member with legs portions 502a, 502b disposed on opposite sides of the collapsible pocket 506. For example, the wedge element 502 can be a flexible member, such as a suture, that is bent from a substantially straight initial configuration to the illustrated U-shape configuration. A removable positioning member 508, such as a wire loop, a suture, or other structure, can be used to insert the wedge element 502 at the appropriate position between the coupling member 302 and suture 504. Alternatively, each leg portion 502a, 502b may instead be a separate wedge element, in which case suture 504 may also pass through the leg portions 502a, 502b to retain the wedge elements to the coupling member 302 during assembly without otherwise falling off. The wedge element or elements 502 can be formed of any biocompatible material or structure, for example, a relatively thick polymer suture or cable (e.g., polyester suture, such as Ethibond), folded piece of cloth, or any other structure.

Figure 8C:
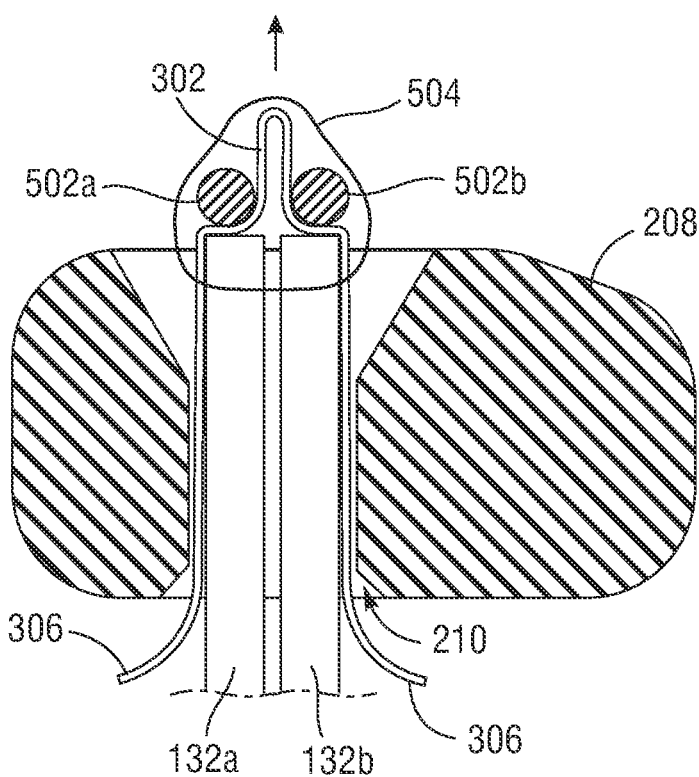

The combination of wedge element 502 and coupling member 302 with pocket 506 collapsed can have a maximum width (e.g., twice the thickness of the wedge element 502 and the coupling member 302) that is less than a width of the closed window 210. The wedge element 502, with pocket 506 collapsed, can thus be inserted through the window 210 first, followed by insertion of the tabs 132a, 132b and coupling member 302, as illustrated in FIG. 8C. For example, the insertion may be such the coupling member 302 passes back through the window 210, with free ends 306 extending from the radially inner end of window 210, as shown in FIG. 8C.

In some embodiments, the removable positioning member 508 is wrapped around a portion of the wedge element 502 between the leg portions 502a, 502b. Alternatively, the removable positioning member 508 can pass through pocket 506 to wrap around the coupling member and/or wedge element 502. In either case, the removable positioning member 508 can assist in passing the wedge element 502, coupling member 302, and tabs 132a, 132b from the radially inner end of window 210 to the radially outer end of window 210. Once insertion through the window is complete, the positioning member 508 can be removed from the assembly.

Figure 8D:
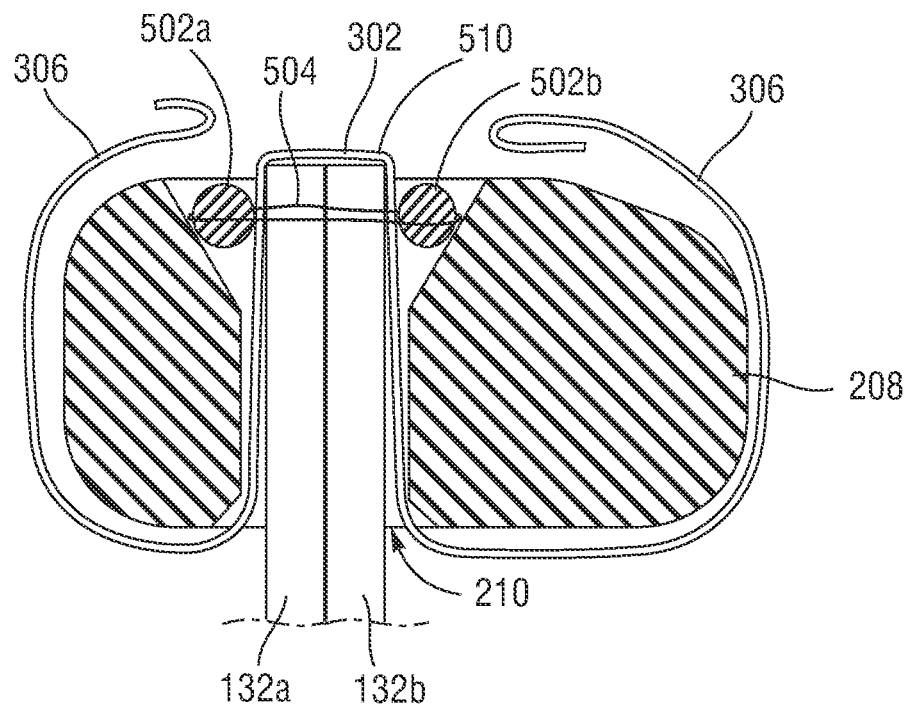

Once the tabs 132a, 132b are fully inserted through window 210, sutures 504 can be tightened, thereby eliminating pocket 506. In particular, coupling member 302 is displaced into contact with the radially outermost end of the tabs 132a, 132b, while wedge element 502 is moved to a position along the radial direction coinciding with the tabs 132a, 132b, as shown in FIG. 8D. The wedge element 502 can be disposed along the radial direction between the frame 102 and the support member 208, for example, between the radially outermost end of the tabs 132a, 132b and the radially outer end of the window 210. The wedge element 502 can be sized/shaped so as to provide an effective increased width along a circumferential direction for a portion of the commissure tab assembly 510. This increased width portion of the commissure tab assembly 510 may be greater than a width of the radially outer end of window 210, such that the commissure tab assembly 510 is prevented, or at least restrained, from passing back through window 210 (e.g., radially inward toward a centerline of the frame 102) by interaction between the increased width portion of commissure tab assembly 510 and window 210.

Once the commissure tab assembly 510 is inserted through window 210 and sutures 504 are tightened, the free ends 306 of the coupling member 302 that extend radially inward can be wrapped around the window frame portions of the support member 208 back toward the radially outer side of the support member, as illustrated in FIG. 8D. In some embodiments, the free ends 306 of coupling member 302 can optionally be secured, for example, by stitching the free ends 306 to a radially outer end portion of the commissure tab assembly 510 via one or more second sutures, in a manner similar to that illustrated in FIG. 6H. The wrapping and stitching of the coupling member 302 can further secure the commissure tab assembly 510 to the support member 208. In some embodiments, the free ends 306 may include folded over portions to which the second sutures are attached.

Installing the commissures tab assembly 510 to the support member 208 in this manner can provide several advantages. For example, the configuration illustrated in FIGS. 8A-8D can allow a significant portion of the commissure tab assembly 510 to be pre-assembled prior to attachment to the frame 102. Attachment of the assembly 510 to the frame 102 may be relatively simple, involving tightening of suture 504 after insertion into window 210 and securing of the coupling member 302 once the commissure tab assembly. Moreover, the coupling member 302 can serve as a protective layer between the leaflet tabs 132a, 132b and the portions of the support member 208 forming window 210.

In some embodiments, one or more additional wedge elements can be provided at a radially inner end of the closed window as well as at the radially outer end, thereby restricting radial motion of the commissure tab assembly in inward and outward directions. A coupling member can be wrapped around external surfaces of a pair of adjacent leaflet tabs and attached thereto. One or more first wedge elements can optionally be disposed on the coupling member and attached to the coupling member and tabs to form the commissure tab assembly. The commissure tab assembly can be inserted through the closed window of the support member until further insertion is restricted by the first wedge elements. After insertion, a second wedge element can be inserted into the commissure tab assembly at the radially outer side of the window, thereby increasing a width of the commissure tab assembly such that the tab assembly cannot pass back through the window. In some embodiments, the window may have a height along the axial direction that tapers from the radially inner side toward the radially outer side of the window. The first wedge element may thus have a length, corresponding to the height at the radially inner side of the window, longer than that of the second wedge element, corresponding to the height at the radially outer side of the window.

Figure 9A:
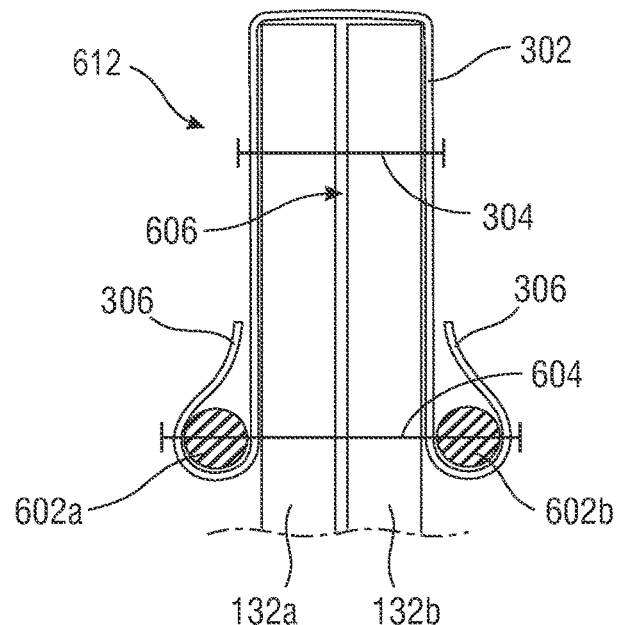
FIGS. 9A-9B are top down and cross-sectional side views, respectively, of a first stage in assembling a commissure tab assembly to a tapered closed window of a support member, according to a fifth example.

For example, FIGS. 9A-9E illustrate a fifth exemplary method of installing a commissure tab assembly 612 to a support member 608 using a first wedge element 310. Referring initially to FIG. 9A, an initial assembly, comprised of adjacent tabs 132a, 132b and coupling member 302, can be formed in a manner similar to that described above with respect to FIGS. 6A-6B. After stitching at 304 and flexing of the tabs 132a, 132b toward each other, one or more second wedge elements 602a, 602b can be disposed on external surfaces of the coupling member 302 at a location spaced from the ends of the tabs 132a, 132b. The free ends 306 of the coupling member 302 can optionally be wrapped around the second wedge elements 602a, 602b. One or more second sutures 604 are passed through the free ends 306, second wedge elements 602a, 602b, and tabs 132a, 132b to stitch together the components to form the commissure tab assembly 612, as shown in FIG. 9A. In some embodiments where first suture 304 is employed, the second wedge elements 602a, 602b and second suture 604 may optionally be omitted. In other embodiments where second suture 604 and second wedge elements 602a, 602b are employed, first suture 304 may be omitted. However, as illustrated in FIGS. 9A-9E, it may be preferable to include first suture 304, second suture 604, and second wedge elements 602a, 602b.

For example, the second wedge element 602 can be a substantially U-shaped member with 602a, 602b being separate leg portions disposed on opposite sides of the tabs 132a, 132b. For example, the second wedge element 602 can be a flexible member, such as a suture, that is bent from a substantially straight initial configuration to a U-shaped configuration. Alternatively, each of 602a, 602b may instead be a separate wedge element. The second wedge element or elements 602 can be formed of any biocompatible material or structure, for example, a relatively thick polymer suture or cable (e.g., polyester suture, such as Ethibond), folded piece of cloth, or any other structure.

The commissure tab assembly 612, with coupling member 302, can then be passed through a radially inner end 610a of window 610 to extend beyond a radially outer end 610b of window 610 until second wedge elements 602a, 602b (or separate leg portions of a U-shaped second wedge element) abut the radially inner end 610a, as shown in FIGS. 9B-9E. The window 610 can have a height along the axial direction of the frame that varies along the radial direction. In particular, a height of the window 610 at the radially inner end 610a can be greater than a height of the window 610 at the radially outer end 610b. For example, the height at the radially inner end 610a can be 1.5-2 times greater than the height at the radially outer end 610b.

Figure 9B:
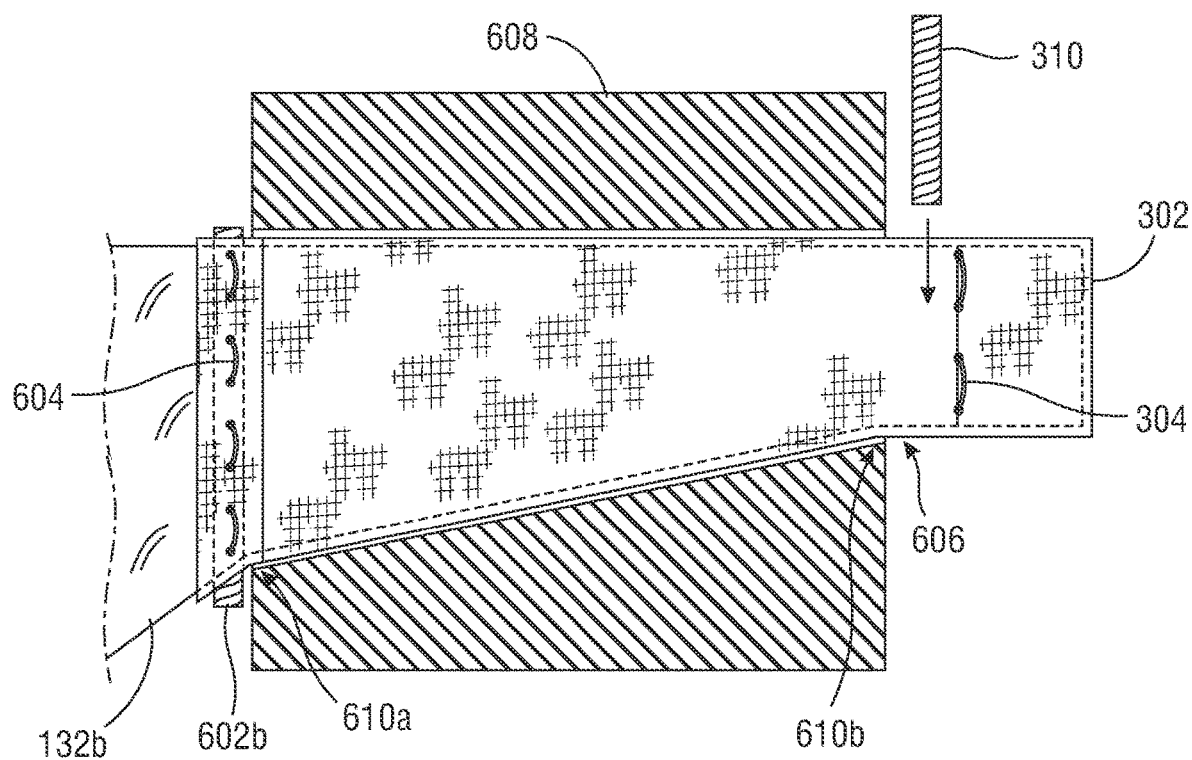
Figure 9C:
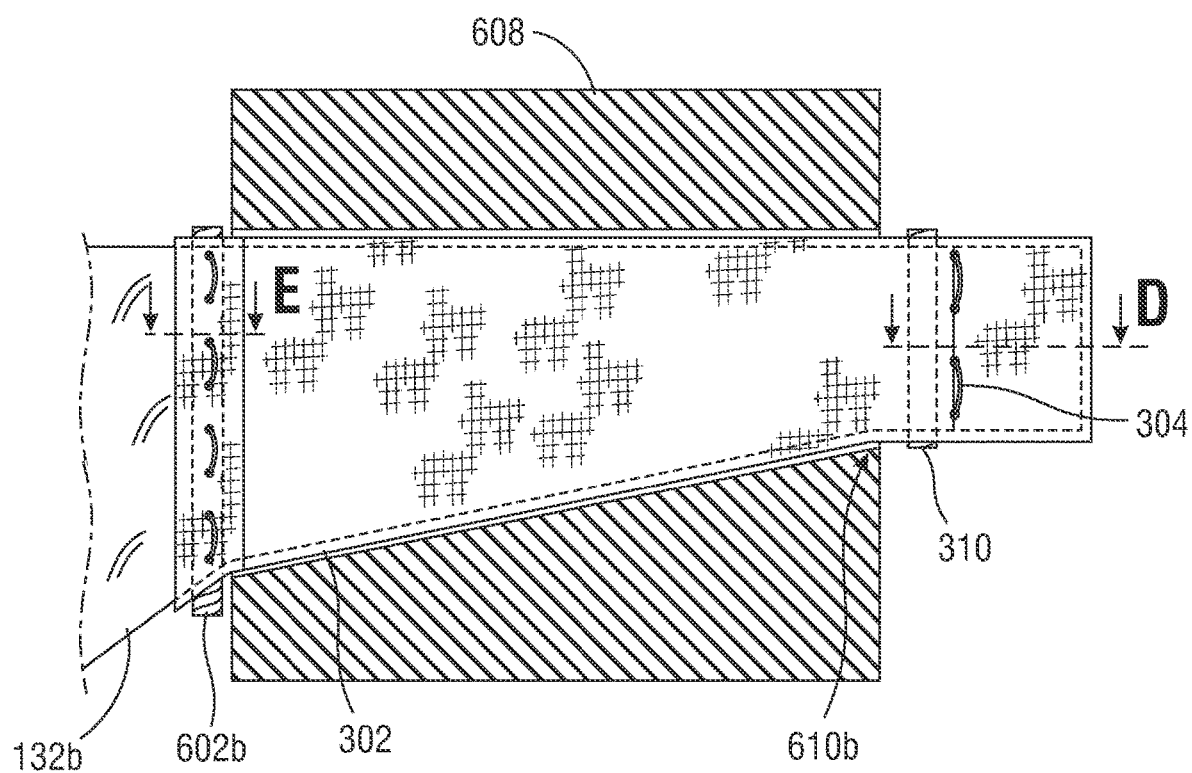
FIGS. 9C and 9D-9E are cross-sectional side and top down views, respectively, of a second stage in assembling the commissure tab assembly to the tapered closed window of the support member, according to the fifth example.

Although FIGS. 9B-9C show an upper edge (e.g., proximal edge) of window 610 being straight and a lower edge (e.g., distal edge) of window 610 being inclined, other configurations are also possible according to one or more contemplated embodiments. For example, the upper edge of window 610 could instead be inclined with the lower edge being straight. In still another example, both edges of window 610 may be at an angle, where the respective angles of inclination/declination may be substantially the same as each other or different from each other.

Figure 9D:
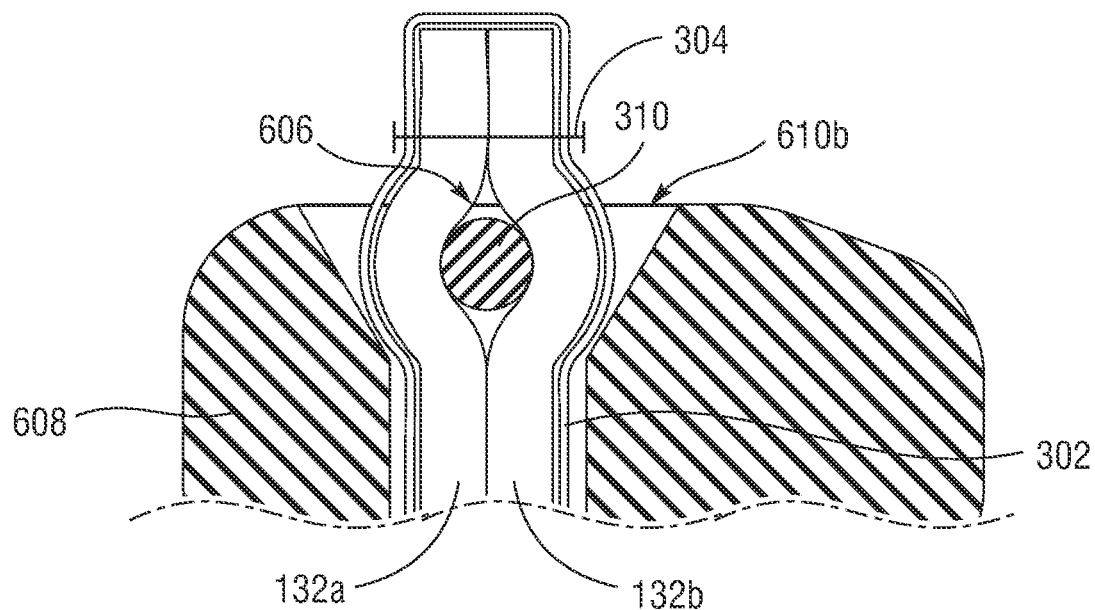
Figure 9E:
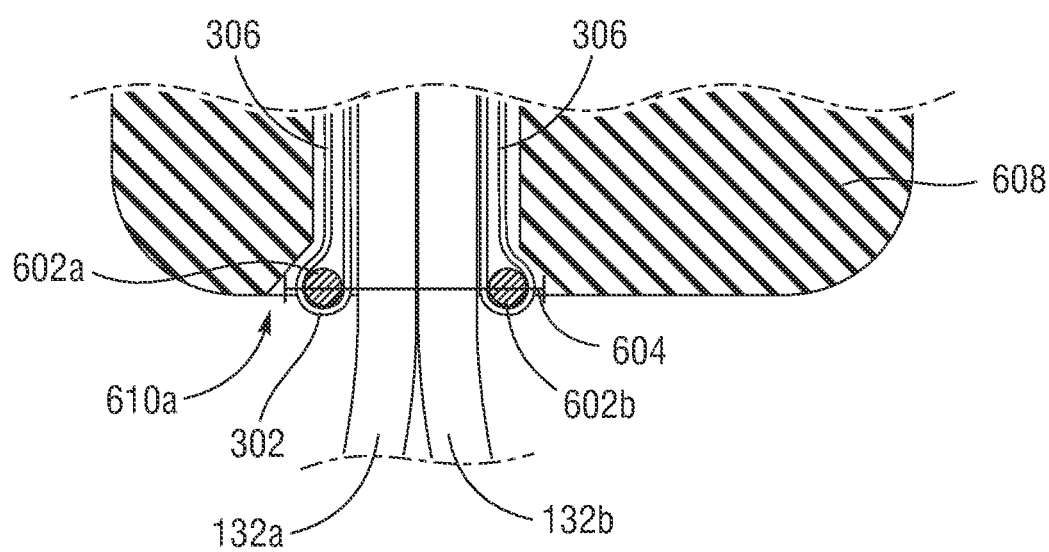

Once fully inserted through window 610, the first wedge element 310 can be inserted into a pocket 606 between adjacent tabs 132a, 132b of the commissure tab assembly 612, as shown in FIGS. 9B-9D. Details regarding the first wedge element 310 (e.g., method of insertion, location of insertion, material composition, handling of loose ends 310a, 310b, etc.), and/or other details of the fifth assembly method may otherwise be similar to that described above for the second assembly method in FIGS. 6A-6F. Thus, the fifth assembly method may offer advantages similar to those offered by the second assembly method. Alternatively, any of the commissure tab assemblies or assembly methods described above with respect to FIGS. 5-8 can be used to form the commissure tab assembly and insert the first wedge element in the fifth assembly method.

Moreover, the use of a tapered window 610, where the radially outer end 610b has a smaller height than the radially inner end 610a, may offer additional advantages. For example, the tapered window 610 can enable the use of tab portions 132a, 132b with a smaller height along the axial direction, which may reduce materials costs for the leaflets, coupling member 302, and wedge element 310. The smaller tab portions can further simplify the assembly procedure, since shorter suture lines can be used to attach the tabs 132a, 132b to coupling member 302.

The tapered window 610 in combination with the second wedge element 602 may also improve the durability of leaflets 130. For example, the second wedge element 602 can insulate the portions of the commissure tab assembly 612 within window 610 from motion of the leaflets 130 during valve operation, thus creating an immobile area within the window 610, which can reduce the risk of damage or abrasion due to impact of the tabs with the support member 608.

Moreover, the longer stitching offered by second suture 604 at the radially inner end 610a of the window can better distribute forces from motion of leaflets 130 during operation to further improve durability. Indeed, in some embodiments, this distribution of forces can allow the size of the leaflet tabs 132a, 132b to be further reduced. For example, the leaflet tabs 132a, 132b may terminate at or just beyond a radial location where the second wedge element 602a, 602b is disposed, such that the leaflet tabs do not extend to the radially outer end 610b of the window 610.

Figure 10C:
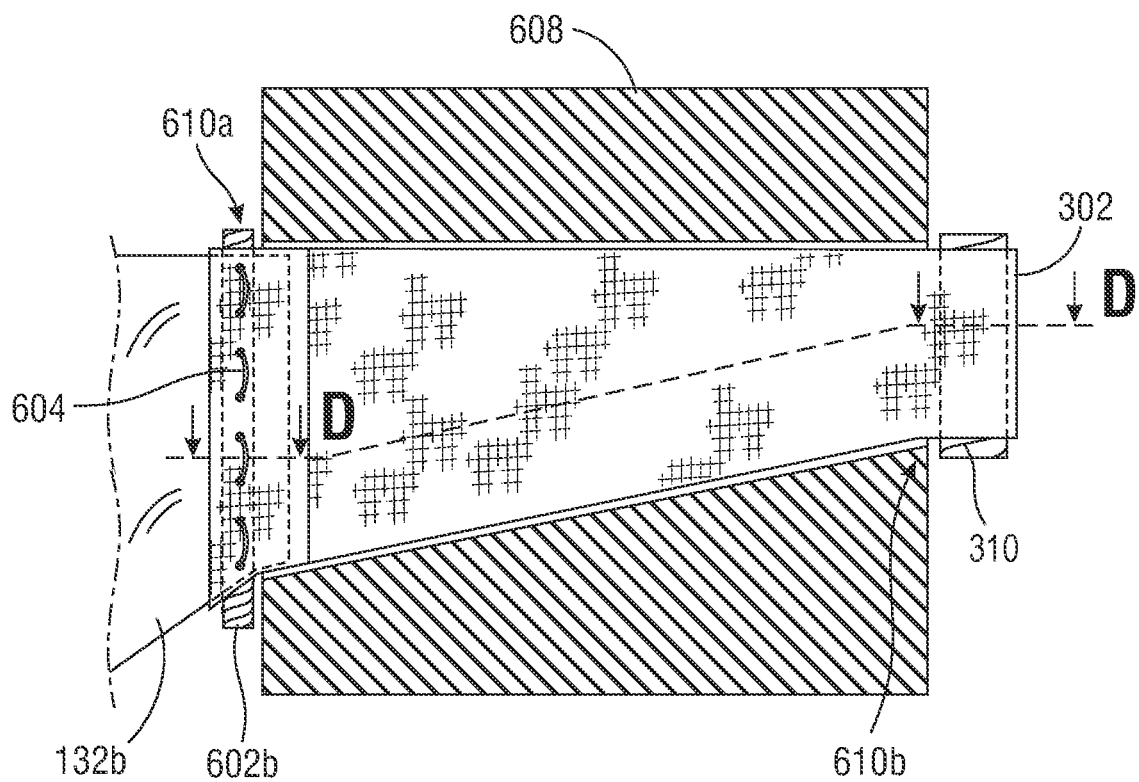
FIGS. 10C-10D are cross-sectional side and top down views, respectively, of a second stage in assembling the commissure tab assembly to the tapered closed window of the support member, according to the sixth example.

For example, FIGS. 10A-10D illustrate a sixth exemplary method of installing a commissure tab assembly to a support member 608 using a first wedge element 310. The sixth assembly method is substantially similar to the fifth method illustrated in FIGS. 9A-9E, but the coupling member 302 extends beyond the ends of the leaflet tabs 132a, 132b to form an internal pocket 616, as illustrated in FIG. 10A. One or more second wedge elements 602a, 602b are disposed on external surfaces of the coupling member at region near the ends of the tabs 132a, 132. The free ends 306 of the coupling member 302 can optionally be wrapped around the second wedge elements 602a, 602b. One or more second sutures 604 are passed through the free ends 306, second wedge elements 602a, 602b, and tabs 132a, 132b to stitch together the components to form the commissure tab assembly, as shown in FIG. 10A.

Figure 10D:
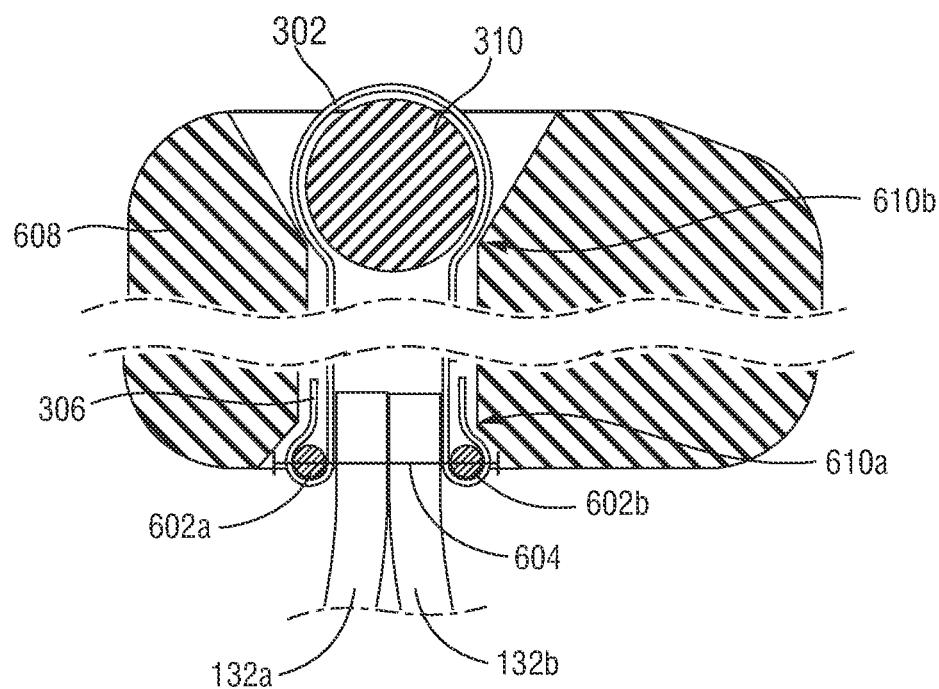

The coupling member 302 can then be passed through the radially inner end 610a of window 610 to extend beyond the radially outer end 610b of window 610 until second wedge elements 602a, 602b (or separate leg portions of a U-shaped second wedge element) abut the radially inner end 610a, as shown in FIGS. 10B-10D. In some embodiments, the insertion may be such that the ends of the leaflet tabs 132a, 132b only minimally (e.g., less than 10% of the length of the window 610 along the radial direction) enter the window 610 at the radially inner end 610a. In other embodiments, the insertion may be such that no portion of the leaflet tabs 132a, 132b enters the window 610.

Once the coupling member 302 is fully inserted through window 610, the first wedge element 310 can be inserted, as shown in FIGS. 10B-10D. For example, wedge element 310 can be conveyed axially with respect to the frame 102 and inserted into pocket 616 between facing surfaces of the coupling member 302. For example, a needle can be used to convey the wedge element 310 into the pocket 616. The wedge element 310 can be disposed along the radial direction between the frame 102 and the support member 608, for example, between an end of pocket 616 formed by coupling member 302 and the radially outer end 610*b* of the window 610 along the radial direction. The wedge element 310 can be any biocompatible material or structure capable of being inserted between surfaces of the coupling member without causing damage thereto (e.g., tearing or ripping) and without degrading when disposed in the patient. For example, the wedge element 310 can be formed from a relatively thick polymer suture or cable (e.g., polyester suture, such as Ethibond), folded piece of cloth, or any other structure.

The wedge element 310 can be sized/shaped so as to define an increased width, along a circumferential direction of the frame 102, for the coupling member pocket 616. The coupling member pocket 616 with wedge element 310 thus has a width greater than a width of the radially outer end 610*b* of window 610, as shown in FIGS. 10C-10D. The commissure tab assembly, which is connected to the coupling member at the other end 610*a* of the window, is prevented, or at least restrained, from moving radially inward toward a centerline of the frame 102 due to interaction between the increased-width coupling member pocket 616 and window 610. The sixth assembly method may otherwise offer advantages similar to those offered by the fifth assembly method, described above.

Figure 11:
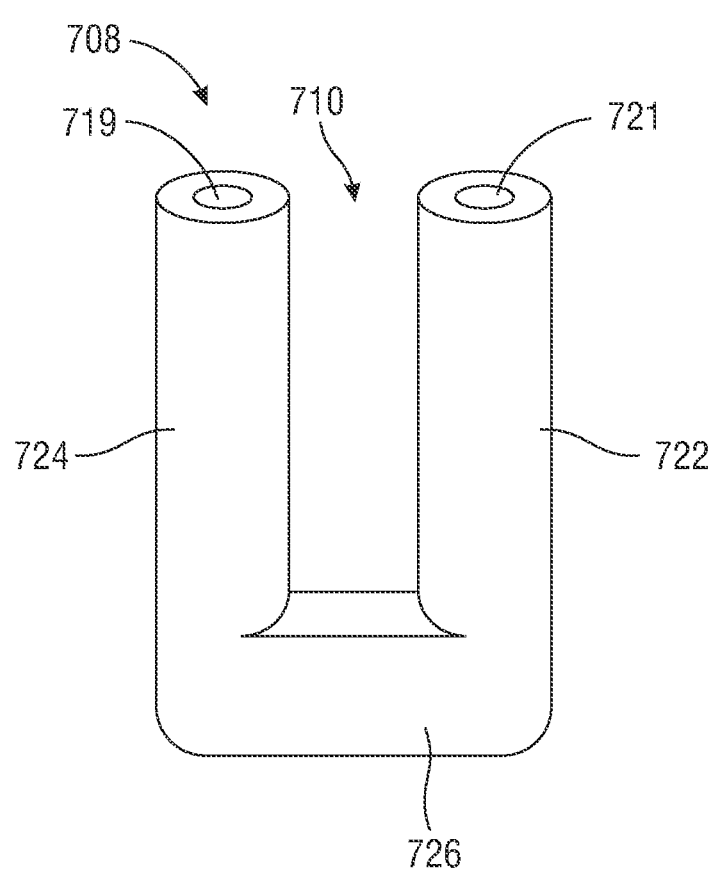
FIG. 11 is a perspective view of an exemplary support member having an open window, according to one or more embodiments of the disclosed subject matter.

Although the description above has focused on support members with closed windows, embodiments of the disclosed subject matter are not limited thereto. Rather, support member window configurations other than closed windows are also possible according to one or more contemplated embodiments. For example, FIG. 11 shows a support member 708, according to another embodiment. Support member 708 can be used, for example, in lieu of support member 108, support member 208, or support member 608 described above. The support member 708 is configured generally similar to any of the previously described support members, but the support member 708 has a window 710 that is open at one axial end, rather than a completely enclosed window 210 of support member 208. The window 710 can thus be considered an open window of the support member 708.

The support member 708 can be a proximal support member of an actuator can comprise an actuation tube 722, a locking tube 724, and a connection portion 726. The tubes 722, 724 can be spaced apart from each other and the connection portion 726 can extend between distal end portions of the tubes 722, 724. The actuation tube 722 can comprise an actuation lumen 721 configured to receive an actuation shaft of a delivery apparatus. The locking tube 724 can comprise a locking lumen 719 configured to receive a locking shaft of a delivery apparatus. The connection portion 726 can be configured for mounting the proximal support member 708 to a frame of a prosthetic valve (e.g., the frame 102). The window 710 of the proximal support member 708 is defined by the tubes 722, 724, and the connection portion 726. In FIG. 11, the window 710 is generally "U" shaped; however, in other embodiments, the window 710 can be tapered or "V" shaped or comprise any other shape capable of receiving therein a commissure tab assembly of the valve structure.

In some embodiments, attachment of the commissure tab assembly to the respective open window of the support member can be achieved by sliding the assembly along the axial direction of the frame into the open window. The commissure tab assembly can include a wedge element that is disposed on a radially outer side of the support member once slid into the open window. The wedge element can define an increased width portion that prevents the commissure tab assembly from passing radially inward through the window.

Figure 12A:
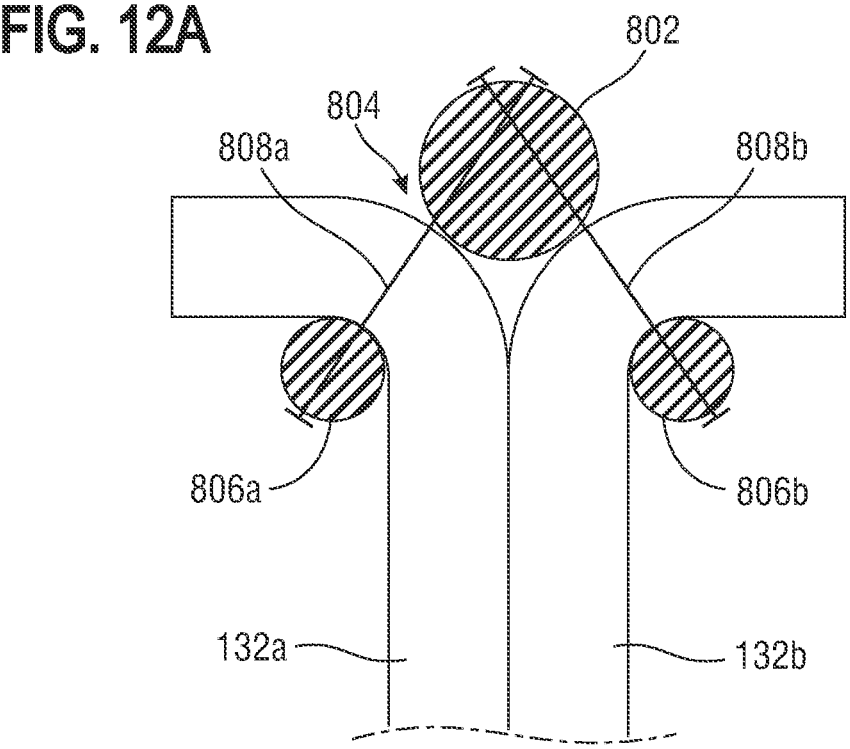
FIGS. 12A-12D are various views illustrating sequential stages in assembling a commissure tab assembly to an open window of a support member, according to a seventh example.

For example, FIGS. 12A-12D illustrate a seventh exemplary method of installing a commissure tab assembly to a support member 708. Referring to FIG. 12A, the commissure tab assembly can be formed by disposing tabs 132*a*, 132*b* of adjacent leaflets 130*a*, 130*b* together. The tabs 132*a*, 132*b* can be flexed in opposite directions at their ends to form a T-shape. An internal wedge element 802 can be disposed at the center of the T-shape. One or more external wedge elements 806*a*, 806*b* can be disposed on opposite sides of the tabs 132*a*, 132*b*, with the internal wedge element 802 therebetween. For example, the external wedge element 806 can be a substantially U-shaped member with legs portions 806*a*, 806*b*. For example, the external wedge element 806 can be a flexible member, such as a suture, that is bent from a substantially straight initial configuration to a U-shaped configuration.

Alternatively, each leg portion 806*a*, 806*b* may instead be a separate wedge element. The internal wedge element 802 and the external wedge element 806*a*, 806*b* can be formed of any biocompatible material or structure, for example, a relatively thick polymer suture or cable (e.g., polyester suture, such as Ethibond), folded piece of cloth, or any other structure.

Figure 12B:
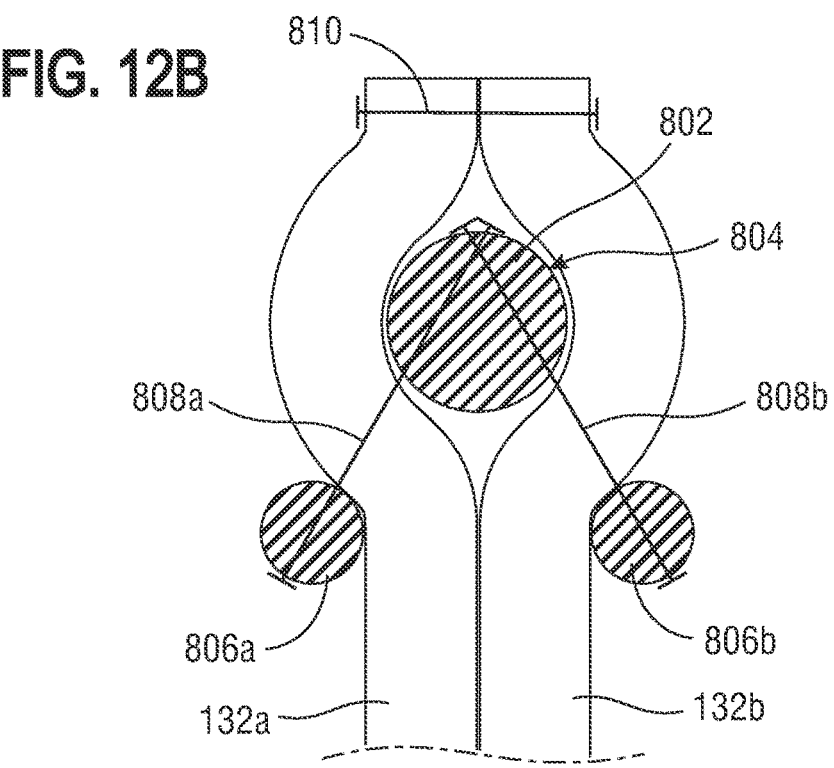

The wedge elements and tabs can then be joined together by stitching, for example, by passing first stitches or suture loops 808*a* through internal wedge element 802, tab 132*a*, and external wedge element 806*a* and by passing second stitches or suture loops 808*b* through internal wedge element 802, tab 132*b*, and external wedge element 806*b*. After stitching, the tabs 132*a*, 132*b* can be straightened from their bent configuration, thereby enclosing the internal wedge element 802 within a pocket 804 between facing surfaces of the tabs 132*a*, 132*b*, as shown in FIG. 12B. In particular, the internal wedge element 802 is disposed along the radial direction between an outer end of the leaflet tabs and the remainder of the leaflets, thereby forming the commissure tab assembly with a portion having an increased width. In some embodiments, the ends of the leaflet tabs 132*a*, 132*b* can be further joined together by stitching, for example, via third stitches or suture loops 810.

Figure 12C:
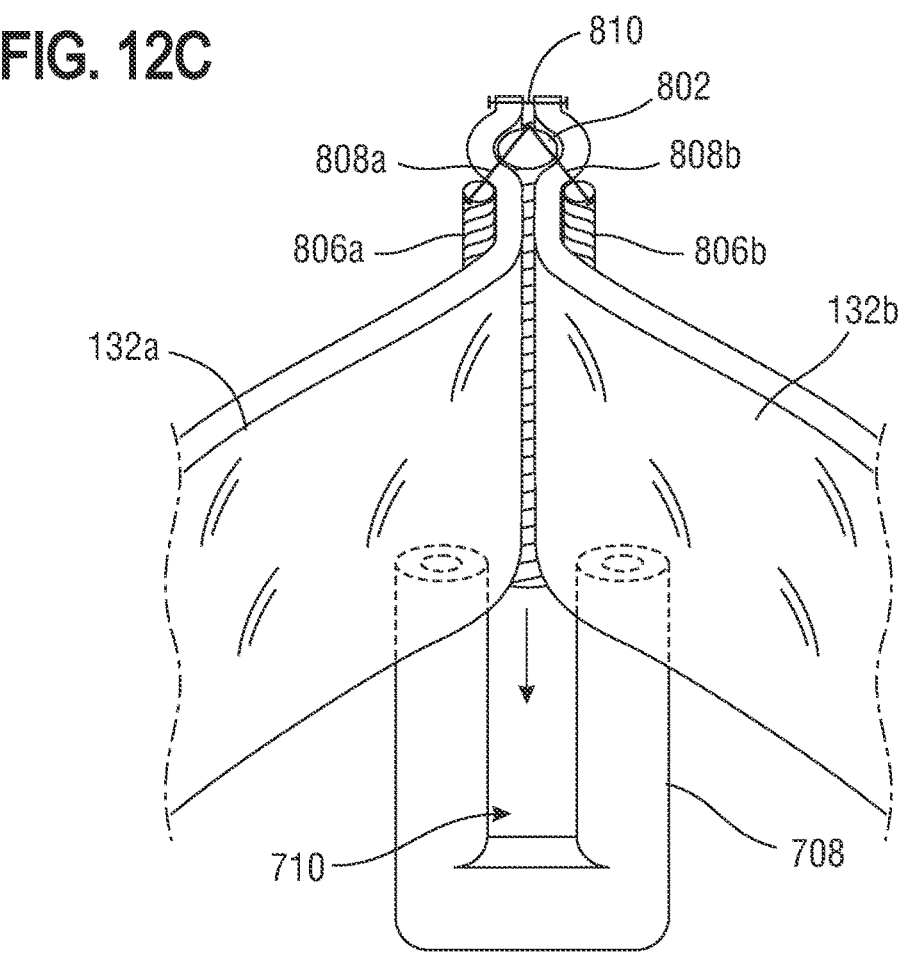
Figure 12D:
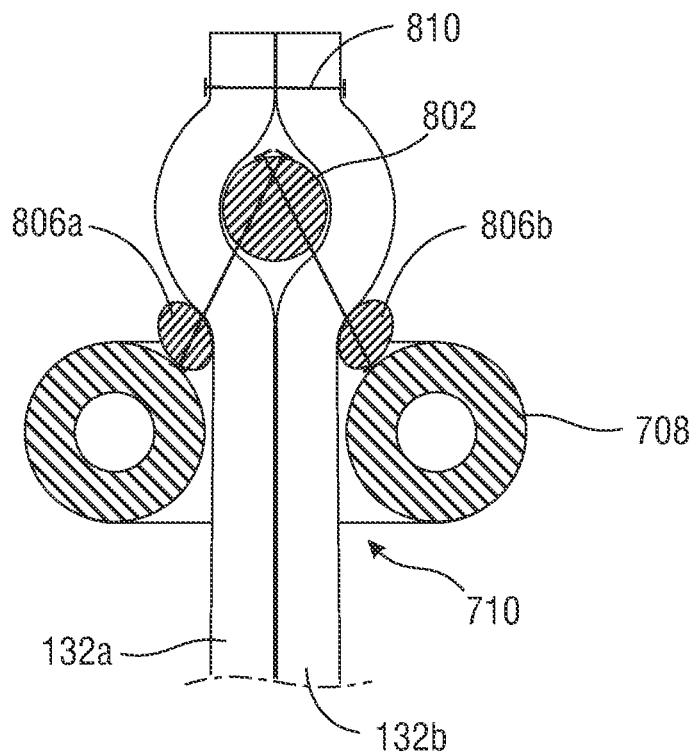

As shown in FIG. 12C, the preassembled commissure tab assembly can then be inserted into the open window 710 of the support member 708. For example, the commissure tab assembly can be conveyed along the axial direction of the annular frame from the proximal end toward the distal end. The increased width portion of the commissure tab assembly can be disposed on a radially outer side of support member 708. Moreover, the increased width of the commissure tab assembly portion may be greater than a width of the radially outer end of window 710. Alternatively or additionally, the external wedge elements 806*a*, 806*b* may define part of the increased width portion of the commissure tab assembly that abuts the radially outer side of window 710, as shown in FIG. 12D. Thus, commissure tab assembly can be prevented, or at least restrained, from passing inward through window 710 (e.g., radially inward toward a centerline of the frame 102) by interaction between the increased width portion of commissure tab assembly and window 710.

The commissure tab assembly can be restrained from moving axially in an upstream direction against retrograde blood flow (e.g., during diastole if implanted at the aortic position) by the connection portion 726. The pressure gradient from antegrade blood flow (e.g., during systole if implanted at the aortic position) typically is insufficient to cause any movement of the commissure tab assembly out of the open end of the support member 708 in a downstream direction. In some embodiments, the frictional engagement between the increased width portion of the commissure tab assembly and the adjacent surfaces of the support member can help resist axial movement of the commissure tab assembly in an upstream direction.

Installing the commissures tab assembly of the leaflets to the support member 708 in this manner can provide several advantages. For example, the configuration illustrated in FIGS. 12A-12D can allow all or substantially all of the commissure tab assembly to be pre-assembled prior to installation to the frame 102. Attachment of the assembly to the frame 102 may be relatively simple, involving only axially sliding the commissure tab assembly into the open window 710 (e.g., slot open toward an axial end of the valve) of the support member 708. This can, for example, make assembling a prosthetic valve easier, improve manufacturing throughput, and/or improve quality. In particular embodiments, the commissure tab assembly is fully assembled prior to installation on the frame and no sutures or other connection structures are used for further assembling the commissure tab assembly or for connecting the commissure tab assembly to the frame.

In some embodiments, the external wedge elements can be replaced with a coupling member, such as a flexible cloth or fabric, disposed around external surfaces of the leaflet tabs. The coupling member can be attached to the internal wedge element and the tabs prior to installation in the open window of the support member. Once inserted into the open window, the coupling member may be wrapped around the support member and attached to the radially outer portion of the commissure tab assembly to further secure the assembly to the support member. The coupling member can thus protect portions of the leaflets from abrasion by interaction with the support member as well as protect portions of the tabs from abrasion with the wedge element.

For example, FIGS. 13A-13D illustrate an eighth exemplary method of installing a commissure tab assembly to a support member 708. The eighth exemplary method of FIGS. 13A-13D may be similar in many respects to the seventh exemplary method of FIGS. 12A-12C. However, coupling member 302 is disposed between facing surfaces of adjacent tabs 132a, 132b as well as over the external surfaces of the tabs. For example, the leaflet tabs 132a, 132b can be disposed adjacent to each other and then flexed in opposite directions to form a T-shape. The coupling member 302 can then be disposed over the surfaces of the leaflet tabs 132, 132b. An internal wedge element 902 can be disposed over the coupling member 302 at the center of the T-shape. The internal wedge element 902 can be formed of any biocompatible material or structure, for example, a relatively thick polymer suture or cable (e.g., polyester suture, such as Ethibond), folded piece of cloth, or any other structure.

Figure 13A:
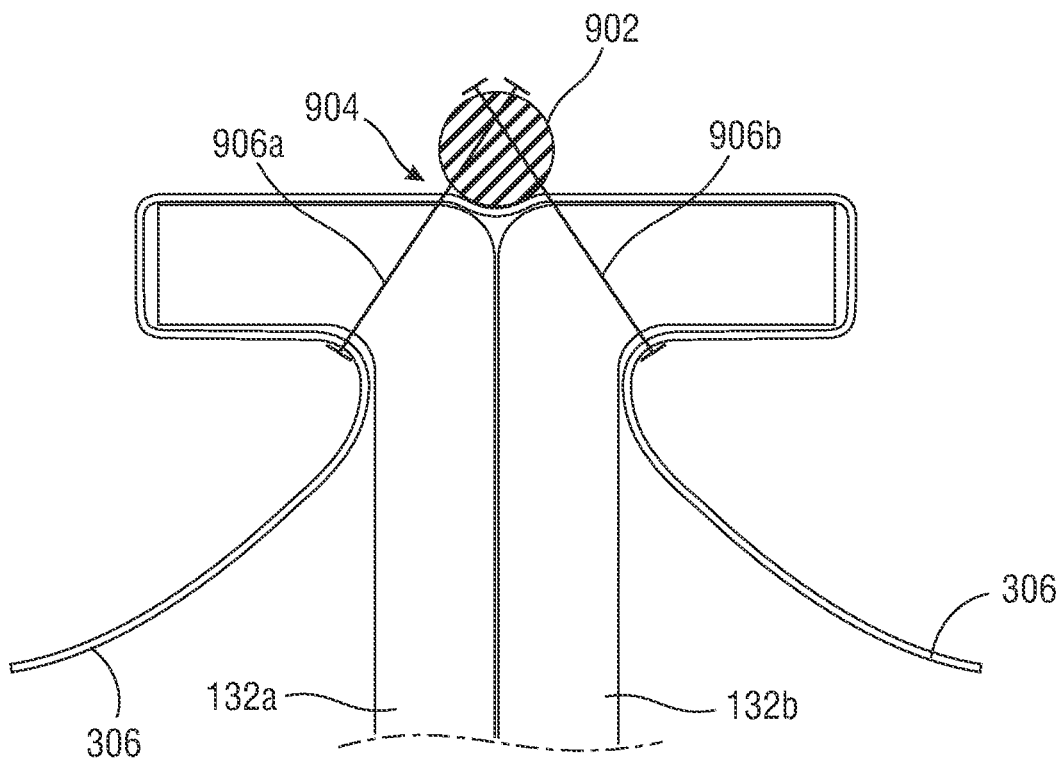
FIGS. 13A-13D are various views illustrating sequential stages in assembling a commissure tab assembly to an open window of a support member, according to an eighth example.
Figure 13B:
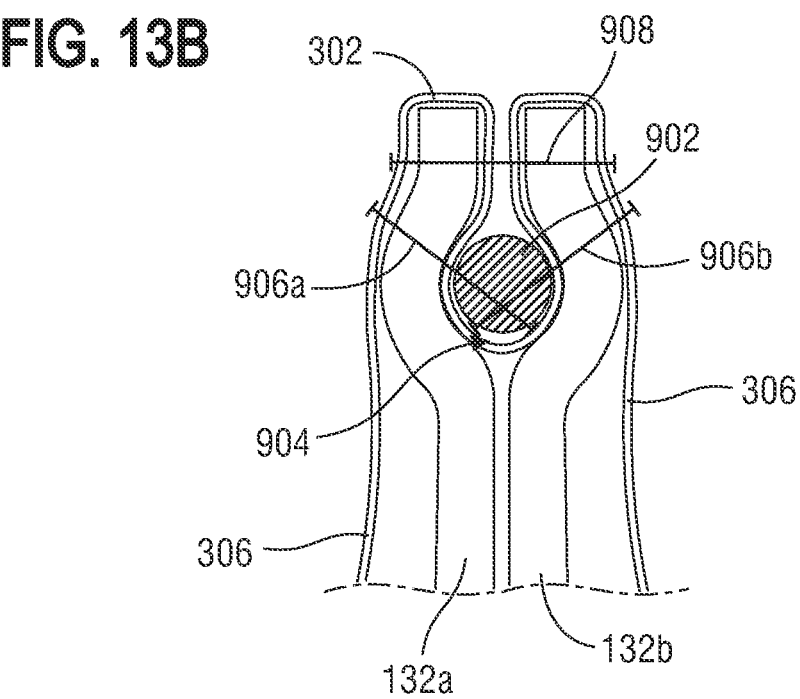

The wedge element 902, coupling member 302, and tabs 132a, 132b can then be joined together by stitching, for example, by passing first stitches or suture loops 906a through one portion of coupling member 302, tab 132a, and wedge element 902 and by passing second stitches or suture loops 906b through another portion of coupling member 302, tab 132b, and wedge element 902. After stitching, the tabs 132a, 132b can be straightened from their bent configuration, thereby enclosing the internal wedge element 902 within a pocket 904 formed by coupling member 302, as shown in FIG. 13B. In particular, the internal wedge element 902 is disposed along the radial direction between an outer end of the leaflet tabs and the remainder of the leaflets, thereby forming the commissure tab assembly with a portion having an increased width. In some embodiments, the ends of the leaflet tabs 132a, 132b can be further joined together by stitching, for example, via third stitches or suture loops 908.

Figure 13C:
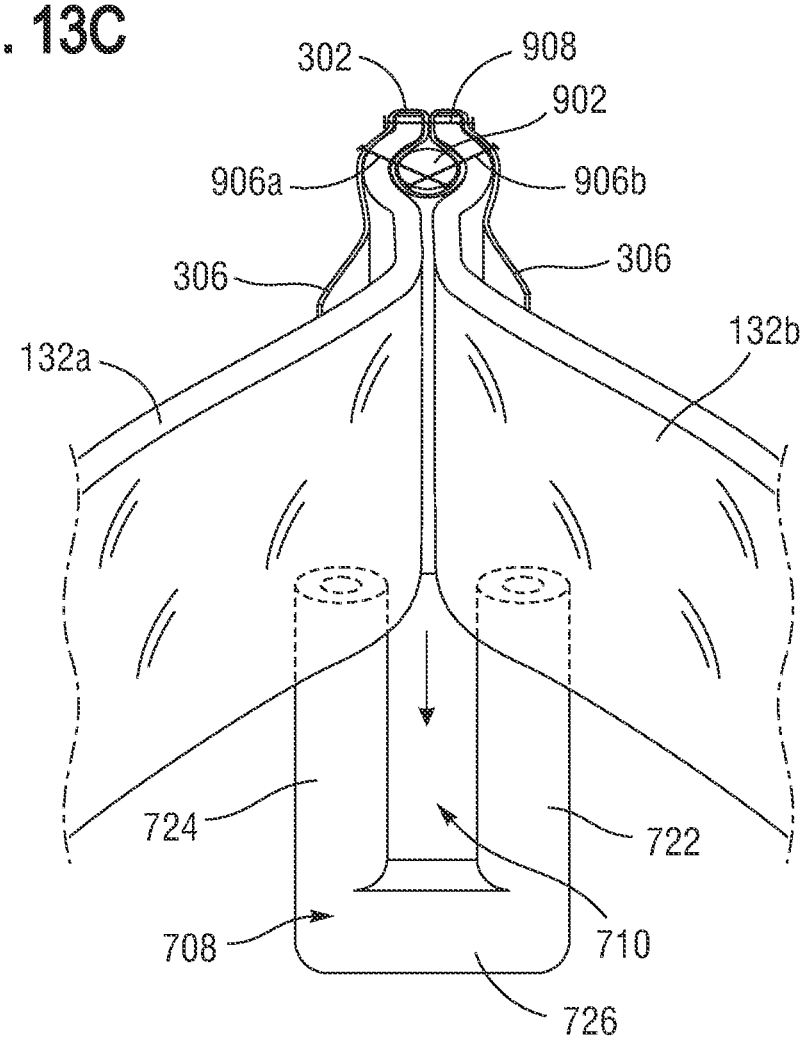

As shown in FIG. 13C, the preassembled commissure tab assembly can then be inserted into the open window 710 of the proximal support member 708. For example, the commissure tab assembly can be conveyed along the axial direction of the annular frame from the proximal end toward the distal end, and the insertion may be such that the coupling member 302 passes back through the window 710, with free ends 306 extending from the radially inner end of window 710, as shown in FIG. 13D.

The increased width portion of the commissure tab assembly can be disposed on a radially outer side of support member 708. Moreover, the increased width of the commissure tab assembly portion may be greater than a width of the radially outer end of window 710. Thus, commissure tab assembly can be prevented, or at least restrained, from passing inward through window 710 (e.g., radially inward toward a centerline of the frame 102) by interaction between the increased width portion of commissure tab assembly and window 710, as shown in FIG. 13D.

Figure 13D:
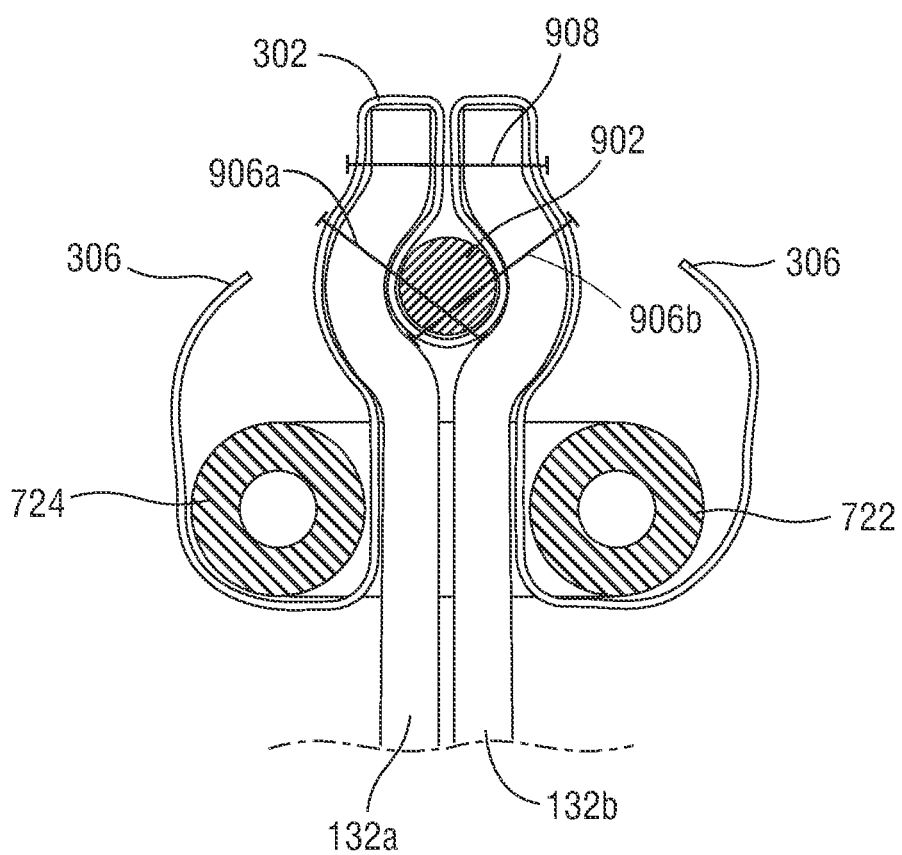

Once the commissure tab assembly is fully inserted into window 710, the free ends 306 of the coupling member 302 that extend radially inward can be wrapped around respective window frame portions 722, 724 of the support member back toward the radially outer side of the support member, as illustrated in FIG. 13D. In some embodiments, the free ends 306 of coupling member 302 can optionally be secured, for example, by stitching the free ends 306 to a radially outer end portion of the commissure tab assembly via one or more additional sutures, for example, similar to attachment of coupling member 302 via sutures 324 in FIG. 6H. In some embodiments, the stitching via third sutures 908 can be delayed until after inserting into window 710. The third sutures 908 can thus be used to attach the free ends 306 of the coupling member 302 as well as the ends of the leaflet tabs 132a, 132b together. The wrapping and stitching of the coupling member 302 can further secure the commissure tab assembly to the support member 708.

Installing the commissures tab assembly of the leaflets to the support member 708 in this manner can provide several advantages. For example, the configuration illustrated in FIGS. 13A-13D can allow all or substantially all of the commissure tab assembly to be pre-assembled prior to installation to the frame 102. Attachment of the assembly to the frame 102 may be relatively simple, involving only axially sliding the commissure tab assembly into the open window 710 (e.g., slot open toward an axial end of the valve) of the support member 708. This can, for example, make assembling a prosthetic valve easier, improve manufacturing throughput, and/or improve quality. Moreover, the coupling member 302 can serve as a protective layer between the leaflet tabs 132a, 132b and the portions of the support member 708 forming window 710.

In some embodiments, the coupling member can be disposed around external surfaces only of the leaflet tabs rather than between the leaflet tabs. The internal wedge element can remain between the leaflet tabs. The coupling member can be attached to the internal wedge element and the tabs prior to installation in the open window of the support member. Once inserted into the open window, the coupling member may be wrapped around the support member and attached to the radially outer portion of the commissure tab assembly to further secure the assembly to the support member. In alternative embodiments, free ends of the coupling member may be otherwise attached to the commissure tab assembly without wrapping around the support member. The coupling member can thus protect portions of the leaflets from abrasion by interaction with the support member.

Figure 14A:
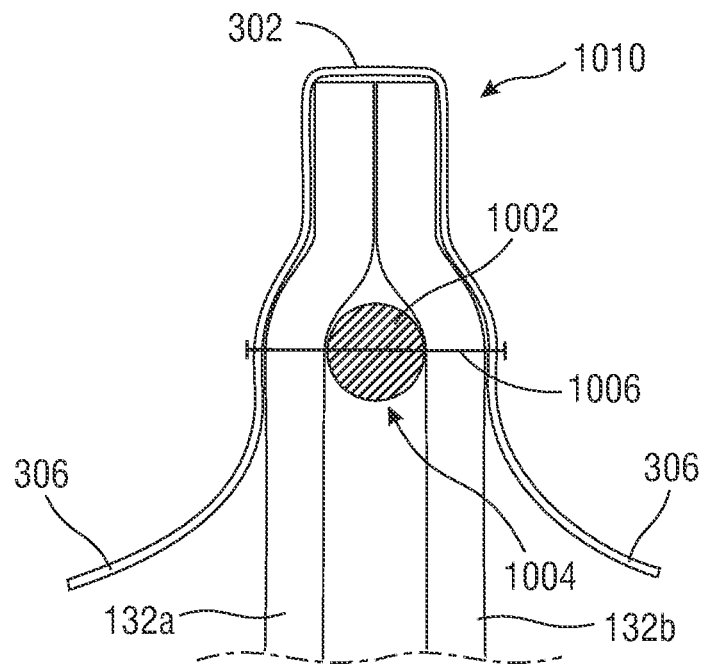
FIGS. 14A-14D are various views illustrating sequential stages in assembling a commissure tab assembly to an open window of a support member, according to a ninth example.
Figure 14B:
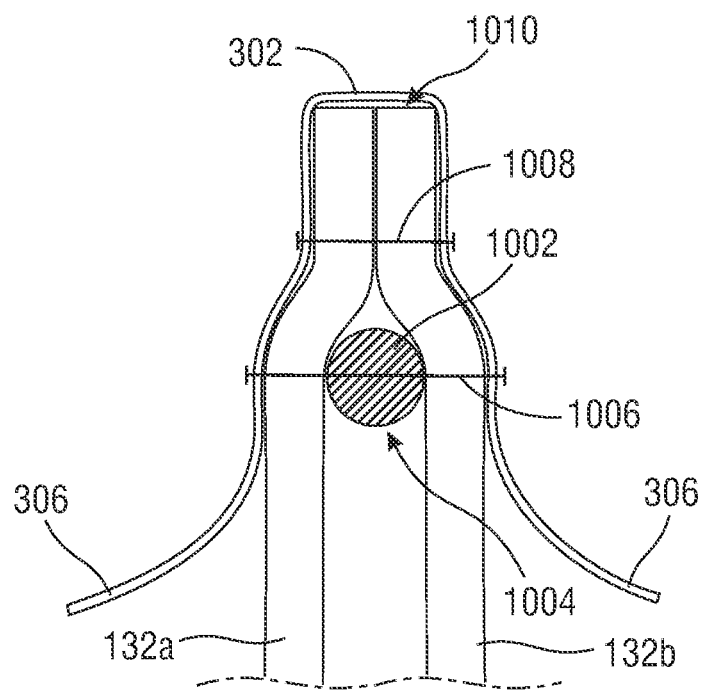

For example, FIGS. 14A-14D illustrate a ninth exemplary method of installing a commissure tab assembly 1010 to a support member 708. The ninth exemplary method of FIGS. 14A-14D may be similar in many respects to the eighth exemplary method of FIGS. 13A-13C. An internal wedge element 1002 can be disposed on a surface of one tab 132a and another tab 132b can be overlaid on top, thereby providing the internal wedge element 1002 in an internal pocket 1004 formed between the adjacent tabs 132a, 132b, as illustrated in FIG. 14A. The internal wedge element 1002 can be formed of any biocompatible material or structure, for example, a relatively thick polymer suture or cable (e.g., polyester suture, such as Ethibond), folded piece of cloth, or any other structure.

A coupling member 302 can then be disposed over the surfaces of the leaflet tabs 132, 132b. However, in contrast to the eighth exemplary method, coupling member 302 is disposed only over the external surfaces of the adjacent tabs 132a, 132b. The wedge element 1002, coupling member 302, and tabs 132a, 132b can then be joined together by stitching, for example, via first stitches or suture loops 1006, to form the commissure tab assembly 1010. The internal wedge element 1002 is disposed along the radial direction between an outer end of the leaflet tabs and the remainder of the leaflets, thereby forming the commissure tab assembly 1010 with a portion having an increased width. In some embodiments, the ends of the leaflet tabs 132a, 132b can be further joined together by stitching, for example, via second stitches or suture loops 1008.

Figure 14C:
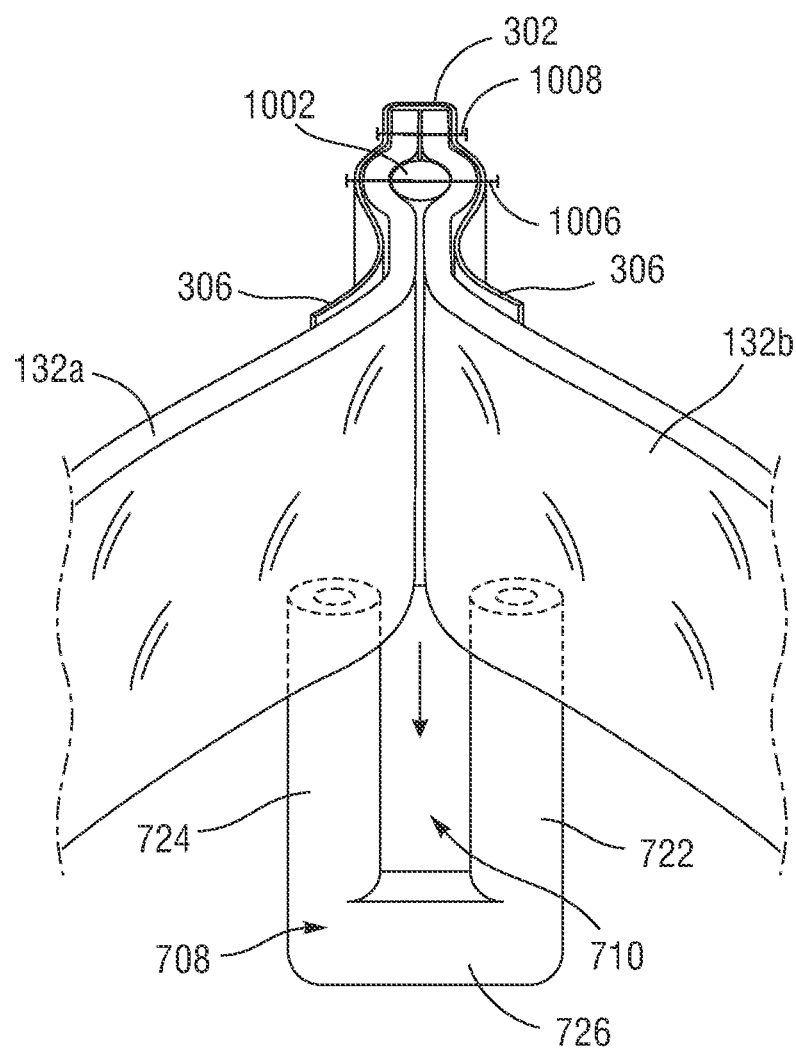

As shown in FIG. 14C, the preassembled commissure tab assembly can then be inserted into the open window 710 of the proximal support member 708. For example, the commissure tab assembly 1010 can be conveyed along the axial direction of the annular frame from the proximal end toward the distal end, and the insertion may be such that the coupling member 302 passes back through the window 710, with free ends 306 extending from the radially inner end of window 710, as shown in FIG. 14D.

The increased width portion of the commissure tab assembly 1010 can be disposed on a radially outer side of support member 708. Moreover, the increased width of the commissure tab assembly portion may be greater than a width of the radially outer end of window 710. Thus, commissure tab assembly 1010 can be prevented, or at least restrained, from passing inward through window 710 (e.g., radially inward toward a centerline of the frame 102) by interaction between the increased width portion of commissure tab assembly and window 710, as shown in FIG. 14D.

Figure 14D:
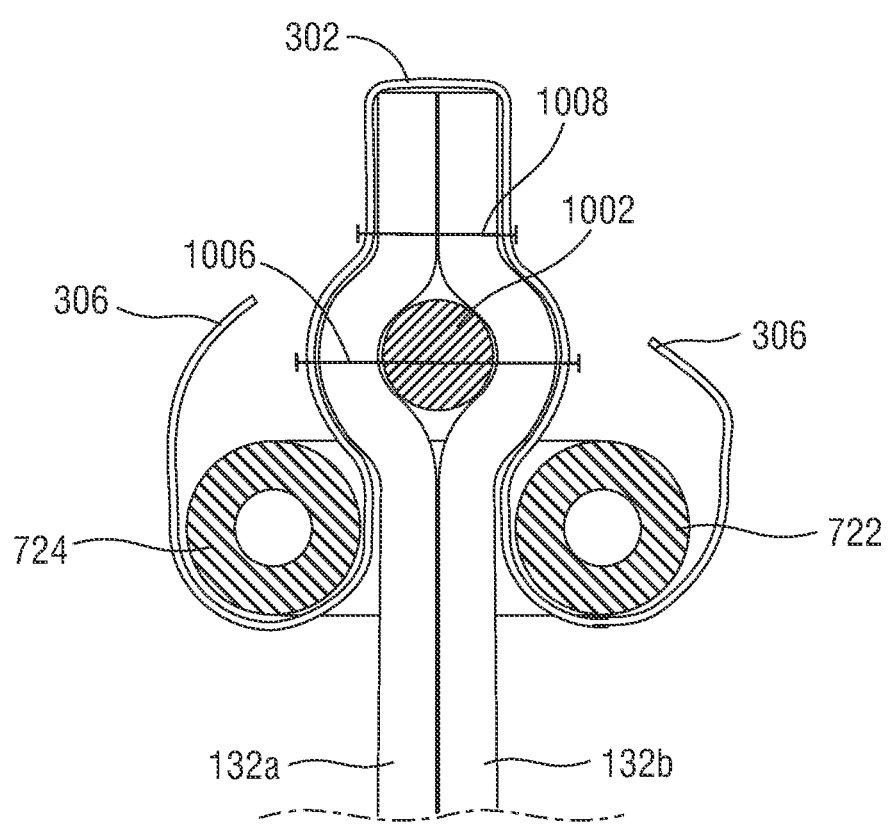

Once the commissure tab assembly 1010 is fully inserted into window 710, the free ends 306 of the coupling member 302 that extend radially inward can be wrapped around respective window frame portions 722, 724 of the support member back toward the radially outer side of the support member, as illustrated in FIG. 14D. In some embodiments, the free ends 306 of coupling member 302 can optionally be secured, for example, by stitching the free ends 306 to a radially outer end portion of the commissure tab assembly via one or more additional sutures, for example, similar to attachment of coupling member 302 via sutures 324 in FIG. 6H. In some embodiments, the stitching via second suture 1008 can be delayed until after inserting the commissure tab assembly 1010 into window 710. The second suture 1008 can thus be used to attach the free ends 306 of the coupling member 302 as well as the ends of the leaflet tabs 132a, 132b together. The wrapping and stitching of the coupling member 302 can further secure the commissure tab assembly 1010 to the support member 708.

In some embodiments, the free ends 306 of the coupling member 302 may be positioned without wrapping around the support member 708. For example, each free end 306 may be folded back on itself through the window 710, such that the free end 306 extends from the radially inner side 1012 to the radially outer side 1016 of the window 710. This may advantageously provide a double thickness portion of the coupling member on each side of the leaflet tabs 132a, 132b to provide further protection. However, since the free ends 306 remain unsecured, they may slide radially outward during operation of the valve, as shown in FIG. 14E.

Figure 14E:
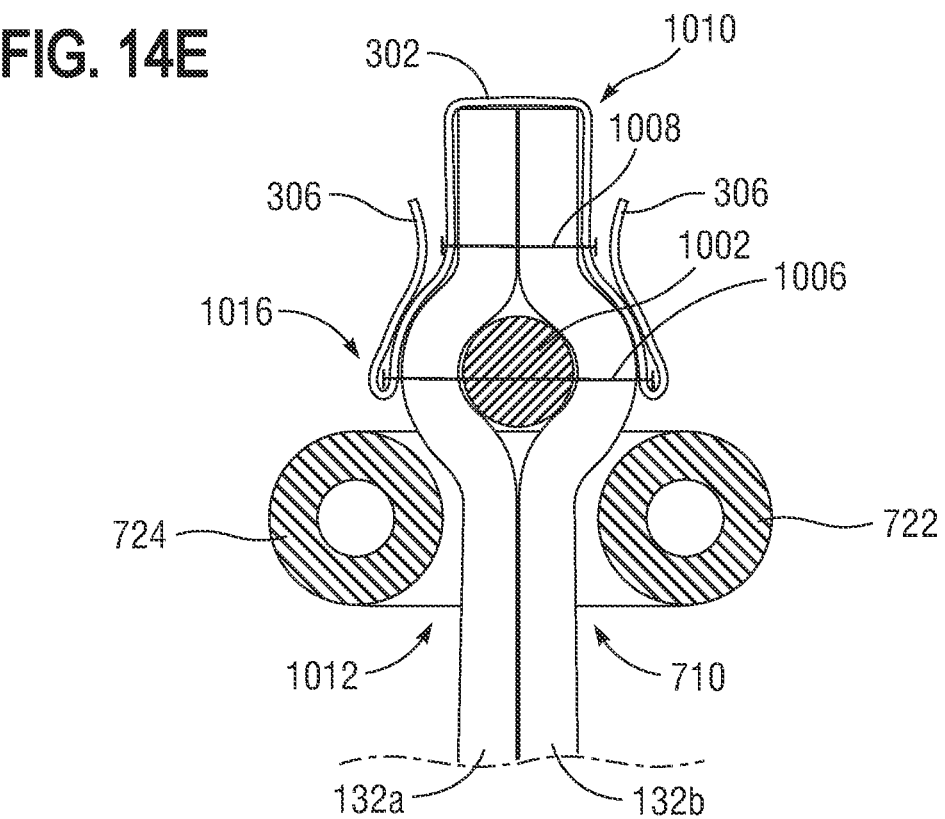
FIG. 14E is a top-down view illustrating a first variation of the ninth example with respect to positioning of a coupling member of the commissure tab assembly.
Figure 14F:
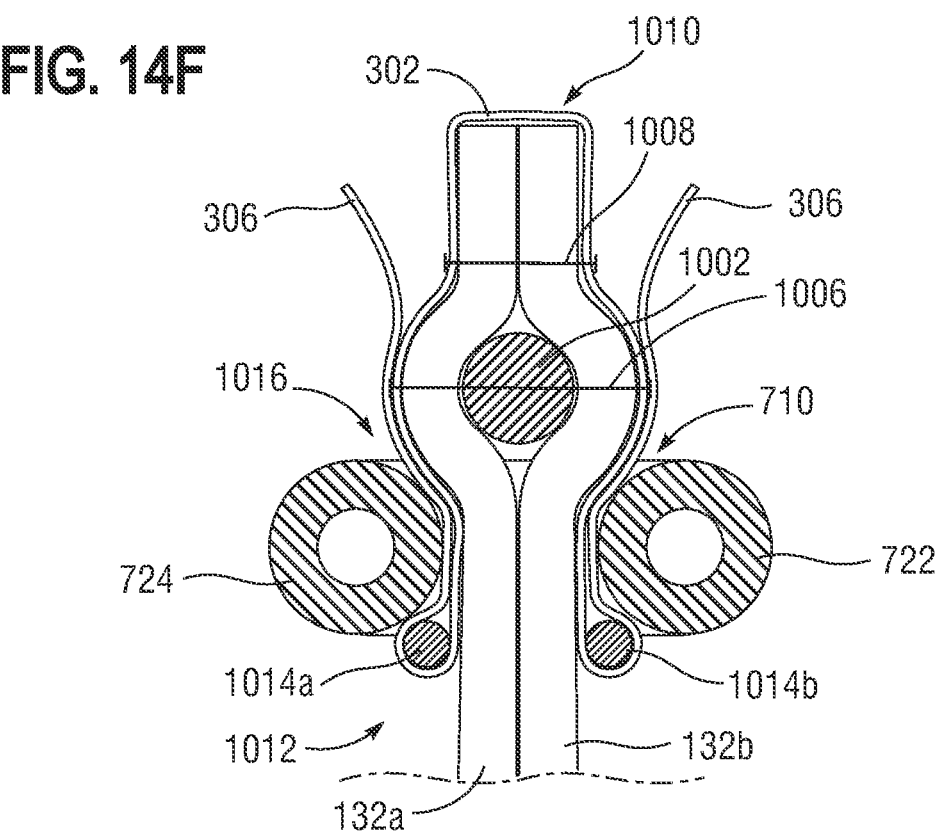
FIG. 14F is a top-down view illustrating a second variation of the ninth example with respect to positioning of a coupling member of the commissure tab assembly.

To avoid the scenario illustrated in FIG. 14E, one or more external wedge elements 1014 can be provided between facing surfaces of the coupling member 302 at the radially inner side 1012 of the window 710, as illustrated in FIG. 14F. External wedge element 1014 can be conveyed axially with respect to the frame 102 and inserted into pockets formed by the folded portion of each coupling member free end 306. For example, a needle can be used to convey the wedge element 1014 between the coupling member portions. In some embodiments, the wedge element 1014 can be a substantially U-shaped member with legs portions 1014a, 1014b disposed on opposite sides of the tabs 132a, 132b. For example, the wedge element 1014 can be a flexible member, such as a suture, that is bent from a substantially straight initial configuration to the illustrated U-shape configuration. Alternatively, each leg portion 1014a, 1014b may instead be a separate wedge element. The wedge element or elements 1014a, 1014b can be formed of any biocompatible material or structure, for example, a relatively thick polymer suture or cable (e.g., polyester suture, such as Ethibond), folded piece of cloth, or any other structure.

Installing the commissures tab assembly 1010 of the leaflets to the support member 708 in this manner can provide several advantages. For example, the configuration illustrated in FIGS. 14A-14F can allow all or at least a significant portion of the commissure tab assembly 1010 to be pre-assembled prior to installation to the frame 102. Attachment of the assembly to the frame 102 may be relatively simple, involving axially sliding the commissure tab assembly 1010 into the open window 710 (e.g., slot open toward an axial end of the valve) of the support member 708 and optionally stitching of the coupling member or insertion of a wedge element into the coupling member. This can, for example, make assembling a prosthetic valve easier, improve manufacturing throughput, and/or improve quality. Moreover, the coupling member 302 can serve as a protective layer between the leaflet tabs 132a, 132b and the portions of the support member 708 forming window 710.

In some embodiments, the coupling member and the internal wedge element can be attached to each other by a suture. The internal wedge element and coupling member can then be inserted between adjacent leaflet tabs, and the coupling member can be further wrapped around the external surfaces of the tabs. The ends of the tabs can be connected together by one or more additional sutures to form the commissure tab assembly. The commissure tab assembly can be inserted into the open window of the support member. Once inserted into the open window, the coupling member may be wrapped around the support member and attached to the radially outer portion of the commissure tab assembly to further secure the assembly to the support member. The coupling member can thus protect portions of the leaflets from abrasion by interaction with the support member, as well as protect portions of the tabs from abrasion with the wedge element.

Figure 15A:
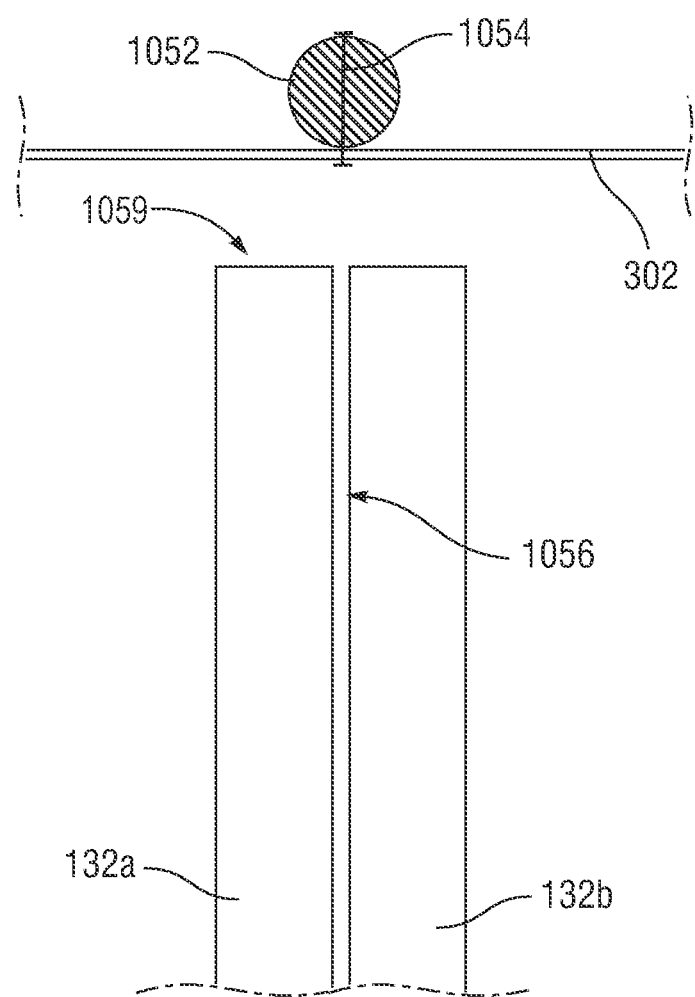
FIGS. 15A-15C are various views illustrating sequential stages in assembling a commissure tab assembly to an open window of a support member, according to a tenth example.
Figure 15B:
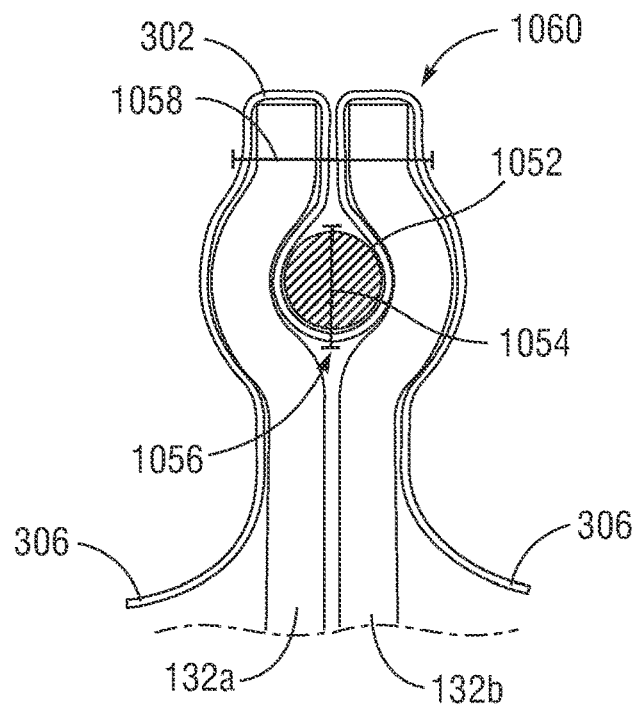
Figure 15C:
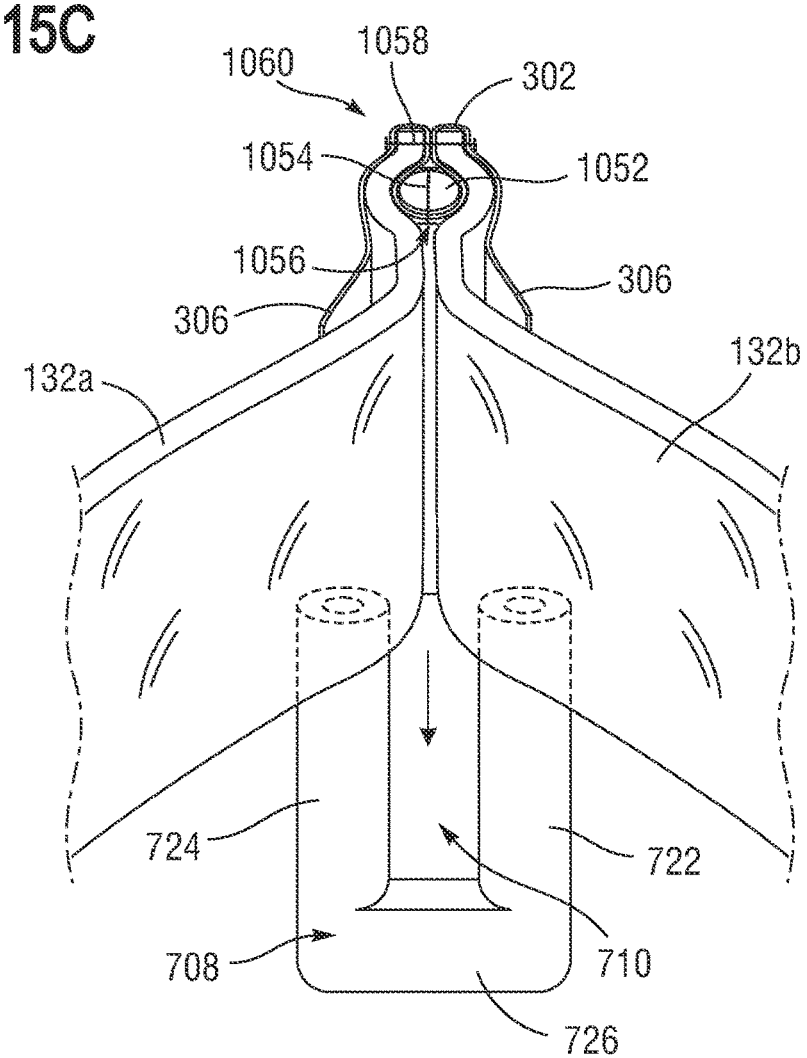

For example, FIGS. 15A-15C illustrate a tenth exemplary method of installing a commissure tab assembly 1060 to a support member 708. The tenth exemplary method of FIGS. 15A-15C may be similar in many respects to the ninth exemplary method of FIGS. 13A-13C. However, the internal wedge element 1052 is attached only to the coupling member 302 rather than to the leaflet tabs 132a, 132b. For example, the internal wedge element 1052 can be disposed on a surface of the coupling member 302, as illustrated in FIG. 15A. The internal wedge element 1052 can be connected to the coupling member 302 by stitching, for example, by one or more first stitches or suture loops 1054. The internal wedge element 902 can be formed of any biocompatible material or structure, for example, a relatively thick polymer suture or cable (e.g., polyester suture, such as Ethibond), folded piece of cloth, or any other structure.

The leaflet tabs 132a, 132b can be disposed adjacent to each other and then flexed in opposite directions to form a T-shape. The combination of coupling member 302 and internal wedge element 1052 can then be disposed over the surfaces of the leaflet tabs 132, 132b, with the internal wedge element 1052 at the center of the T-shape. The tabs 132a, 132b can then be straightened from their bent configuration, thereby enclosing the internal wedge element 1052 within a pocket 1056 between the tabs, as shown in FIG. 15B. In particular, the internal wedge element 1052 is disposed along the radial direction between an outer end 1059 of the leaflet tabs and the remainder of the leaflets, thereby forming the commissure tab assembly 1060 with a portion having an increased width. In some embodiments, the ends of the leaflet tabs 132a, 132b can be further joined together by stitching, for example, via second stitches or suture loops 1058.

As shown in FIG. 15C, the preassembled commissure tab assembly 1060 can then be inserted into the open window 710 of the proximal support member 708. For example, the commissure tab assembly 1060 can be conveyed along the axial direction of the annular frame from the proximal end toward the distal end, and the insertion may be such that the coupling member 302 passes back through the window 710, with free ends 306 extending from the radially inner end of window 710.

The increased width portion of the commissure tab assembly 1060 can be disposed on a radially outer side of support member 708. Moreover, the increased width of the commissure tab assembly portion may be greater than a width of the radially outer end of window 710. Thus, commissure tab assembly 1060 can be prevented, or at least restrained, from passing inward through window 710 (e.g., radially inward toward a centerline of the frame 102) by interaction between the increased width portion of commissure tab assembly and window 710. Once the commissure tab assembly 1060 is fully inserted into window 710, the free ends 306 of the coupling member 302 can be wrapped around the support member 708 (in a manner similar to that described above for FIG. 14D), passed back through window 710 (in a manner similar to that described above for FIGS. 14E-14F), or in any other manner.

In some embodiments, the wedge element or multiple wedge elements can be disposed outside the tabs (e.g., with the tabs therebetween along a circumferential direction of the frame) rather than between the tabs. A coupling member can be wrapped around external surfaces of the tabs, after which a wedge element can be disposed on opposite sides of the coupling member. The wedge element, coupling member, and tabs can be connected together by one or more sutures to form the commissure tab assembly. The commissure tab assembly can be inserted into the open window of the support member. Once inserted into the open window, the coupling member may be wrapped around the support member and attached to the radially outer portion of the commissure tab assembly to further secure the assembly to the support member. The coupling member can thus protect portions of the leaflets from abrasion by interaction with the support member, as well as protect portions of the tabs from abrasion with the wedge element.

Figure 16A:
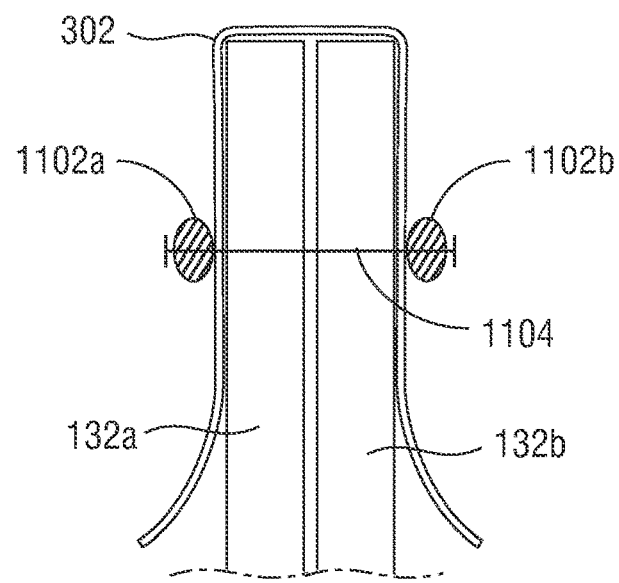
Figure 16B:
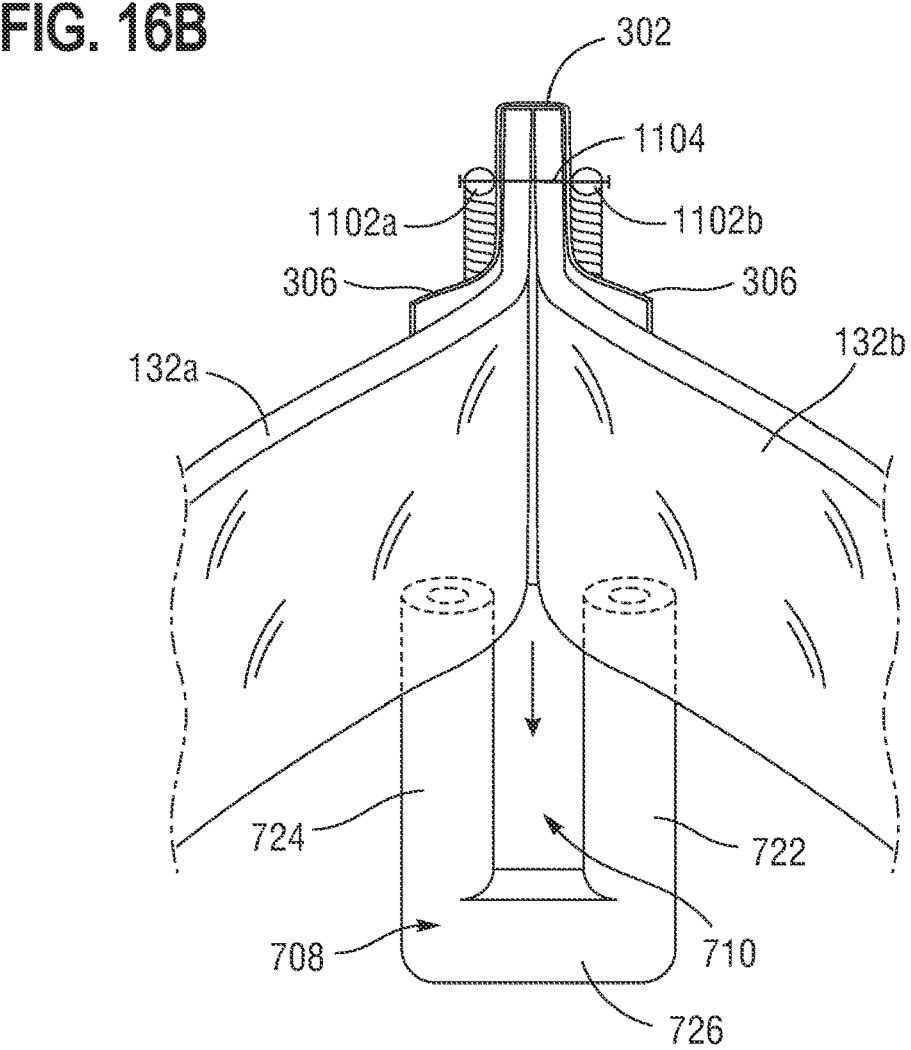

For example, FIGS. 16A-16C illustrate an eleventh exemplary method of installing a commissure tab assembly to a support member 708. Referring initially to FIG. 16A, the commissure tab assembly can be formed by disposing tabs 132a, 132b of adjacent leaflets 130a, 130b together. The coupling member 302 can then be disposed over the external surfaces of the leaflet tabs 132, 132b. One or more external wedge elements 1102a, 1102b can be disposed on opposite sides of the tabs 132a, 132b. For example, the external wedge element 1102 can be a substantially U-shaped member with legs portions 1102a, 1102b. For example, the external wedge element 1102 can be a flexible member, such as a suture, that is bent from a substantially straight initial configuration to a U-shaped configuration.

Alternatively, each leg portion 1102a, 1102b may instead be a separate wedge element. The external wedge element 1102a, 1102b can be formed of any biocompatible material or structure, for example, a relatively thick polymer suture or cable (e.g., polyester suture, such as Ethibond), folded piece of cloth, or any other structure.

The external wedge element 1102a, 1102b and tabs 132a, 132b can then be joined together by stitching, for example, via one or more first stitches or suture loops 1104. The external wedge element 1102a, 1102b is disposed along the radial direction between an outer end of the leaflet tabs and the remainder of the leaflets, thereby effectively forming the commissure tab assembly with a portion having an increased width.

As shown in FIG. 16C, the preassembled commissure tab assembly can then be inserted into the open window 710 of the proximal support member 708. For example, the commissure tab assembly can be conveyed along the axial direction of the annular frame from the proximal end toward the distal end. The increased width portion of the commissure tab assembly can be disposed on a radially outer side of support member 708. Moreover, the combined width of the commissure tab assembly and the external wedge element 1102a, 1102b along the circumferential direction may be greater than a width of the radially outer end of window 710. Thus, the commissure tab assembly can be prevented, or at least restrained, from passing inward through window 710 (e.g., radially inward toward a centerline of the frame 102) by interaction between the external wedge element 1102a, 1102b and window 710. Once the commissure tab assembly is fully inserted into window 710, the free ends 306 of the coupling member 302 can be wrapped around the support member 708 (in a manner similar to that described above for FIG. 14D), passed back through window 710 (in a manner similar to that described above for FIGS. 14E-14F), or in any other manner.

Installing the commissures tab assembly of the leaflets to the support member 708 in this manner can provide several advantages. For example, the configuration illustrated in FIGS. 16A-16C can allow all or substantially all of the commissure tab assembly to be pre-assembled prior to installation to the frame 102. Attachment of the assembly to the frame 102 may be relatively simple, involving only axially sliding the commissure tab assembly into the open window 710 (e.g., slot open toward an axial end of the valve) of the support member 708, and optional attachment of the coupling member free ends. This can, for example, make assembling a prosthetic valve easier, improve manufacturing throughput, and/or improve quality.

In some embodiments, the leaflet tabs can be wrapped around an internal wedge element. Ends of the leaflet tabs can be overlapped with each other and extending in opposite directions. The internal wedge element can be disposed on one of the leaflet tabs. A secondary wedge element can be disposed on a side of the overlapped portion of the leaflet tabs opposite from the internal wedge element. The internal wedge element and the secondary wedge element can be coupled together by one or more sutures, and the leaflet tabs can then be wrapped around the internal wedge element to form the commissure tab assembly. The commissure tab assembly can then be inserted into the open window of a support member.

Figure 17A:
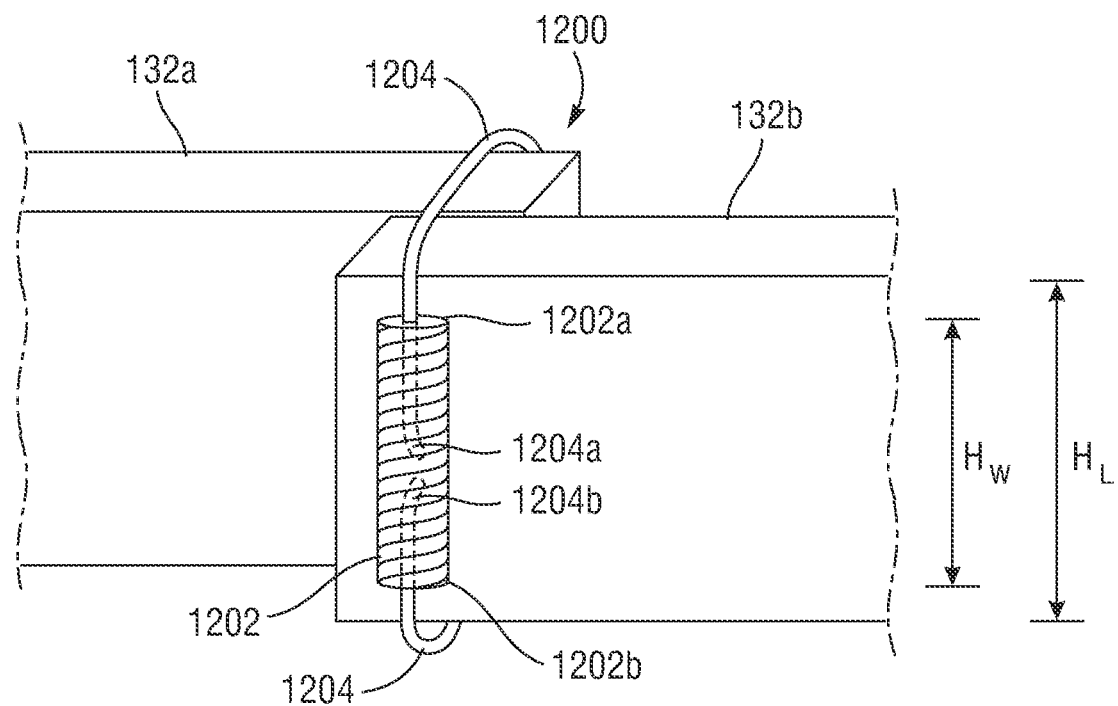
FIGS. 17A-17E are various views illustrating sequential stages in assembling a commissure tab assembly to an open window of a support member, according to a twelfth example.
Figure 17B:
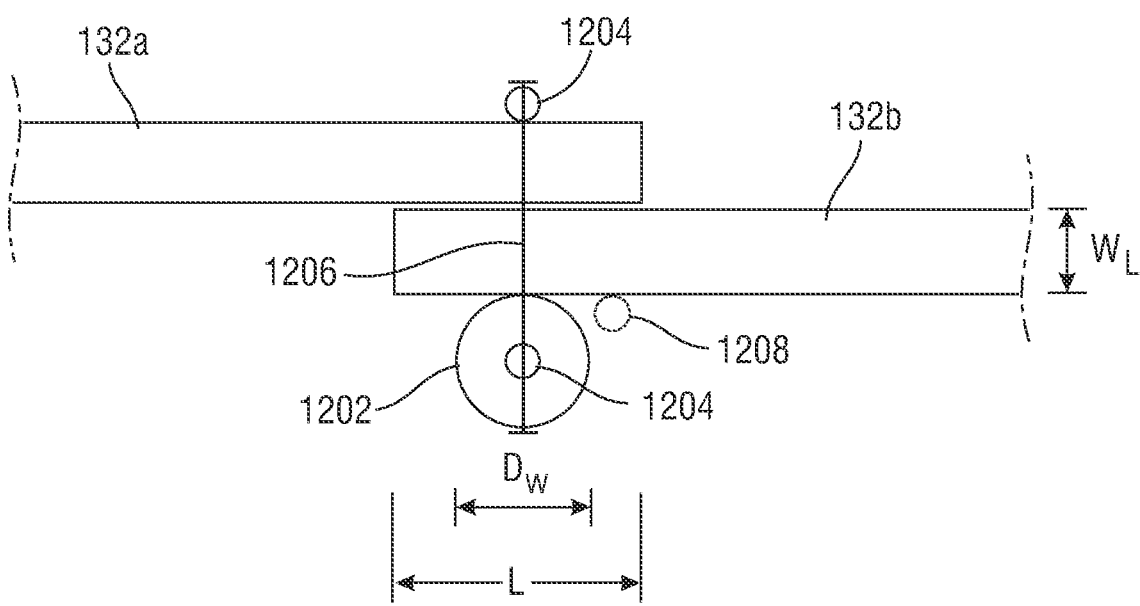
Figure 17C:
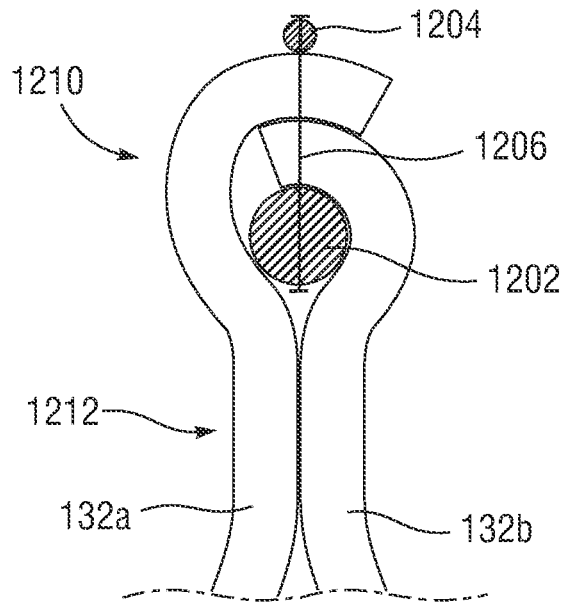

For example, FIGS. 17A-17E illustrate a twelfth exemplary method of installing a commissure tab assembly 1200 to a support member 708. Referring initially to FIGS. 17A-17B, the commissure tab assembly 1200 can be formed by overlapping tabs 132a, 132b. For example, the tabs 132a, 132b can be arranged flat with end surfaces overlapping by a length, L, and the leaflets extending in opposite directions. An internal wedge element 1202 can be disposed on one side of the overlapping section of the leaflet tabs, for example, a surface of tab 132b. For example, the internal wedge element 1202 can have a thickness, $D_w$, less than the length, L, of the overlap, and may be positioned at a midpoint of the overlapped portions (e.g., L/2 from either end of the tabs 132a, 132b).

A secondary wedge element 1204 can be disposed on a side of the overlapping section of the leaflet tabs opposite that of the internal wedge element 1202, for example, a surface of tab 132a. For example, the secondary wedge element 1204 can have a thickness less than the thickness, $D_w$, of the internal wedge element 1202. For example, the internal wedge element 1202 and/or the secondary wedge element 1204 can be formed from a relatively thick polymer suture or cable (e.g., polyester suture, such as Ethibond), folded piece of cloth, or any other structure.

In some embodiments, the internal wedge element 1202 can have a height, $H_w$, (e.g., along an axial direction of the frame when installed) that is less than that the corresponding height, $H_L$, of the overlapped portion of the leaflet tabs. For example, the wedge height, $H_w$, can be less than the tab height, $H_L$, such that the proximal end portion 1202a and distal end portion 1202b of the internal wedge element 1202 are substantially covered by the leaflet tabs 132a, 132b once the tabs are wrapped around the internal wedge element. Such a configuration may mitigate tissue ingrowth by covering portions 1202a, 1202b that may be susceptible when otherwise exposed.

In some embodiments, the secondary wedge element 1204 can have a height greater than height, $H_L$, of the overlapped portion of the leaflet tabs, such that the secondary wedge element 1204 has free ends 1204a, 1204b that extend above or below the leaflet tabs. In such embodiments, the free ends of the secondary wedge element 1204 can be placed in a secured position in an interior of the commissure tab assembly 1200. For example, one free end 1204a of the secondary wedge element 1204 can be inserted into a proximal end portion 1202a of the internal wedge element 1202, while the opposite free end 1204b of the secondary wedge element 1204 can be inserted into a distal end portion 1202b of the internal wedge element 1202, as shown in FIG. 17A. For example, when the internal wedge element 1202 is formed of a multistrand suture, the free ends 1204a, 1204b of the secondary wedge element may be inserted between strands or otherwise woven into wedge element 1202. Alternatively, the free ends 1204a, 1204b may be tucked into a position 1208 adjacent to the internal wedge element 1202, as shown in FIG. 17B.

The wedge elements 1202, 1204 and the leaflet tabs 132a, 132b can be joined together by stitching, for example, by passing first stitches or suture loops 1206 therethrough, as illustrated in FIG. 17B. After stitching, the tabs 132a, 132b can be flexed toward each other to wrap around the internal wedge element 1202 and with facing surfaces contacting each other to form the commissure tab assembly illustrated in FIG. 17C. The internal wedge element 1202 is thus enclosed by the wrapped leaflet tabs 132a, 132b, with the secondary wedge element 1204 disposed at radially outermost end of the commissure tab assembly.

Figure 17D:
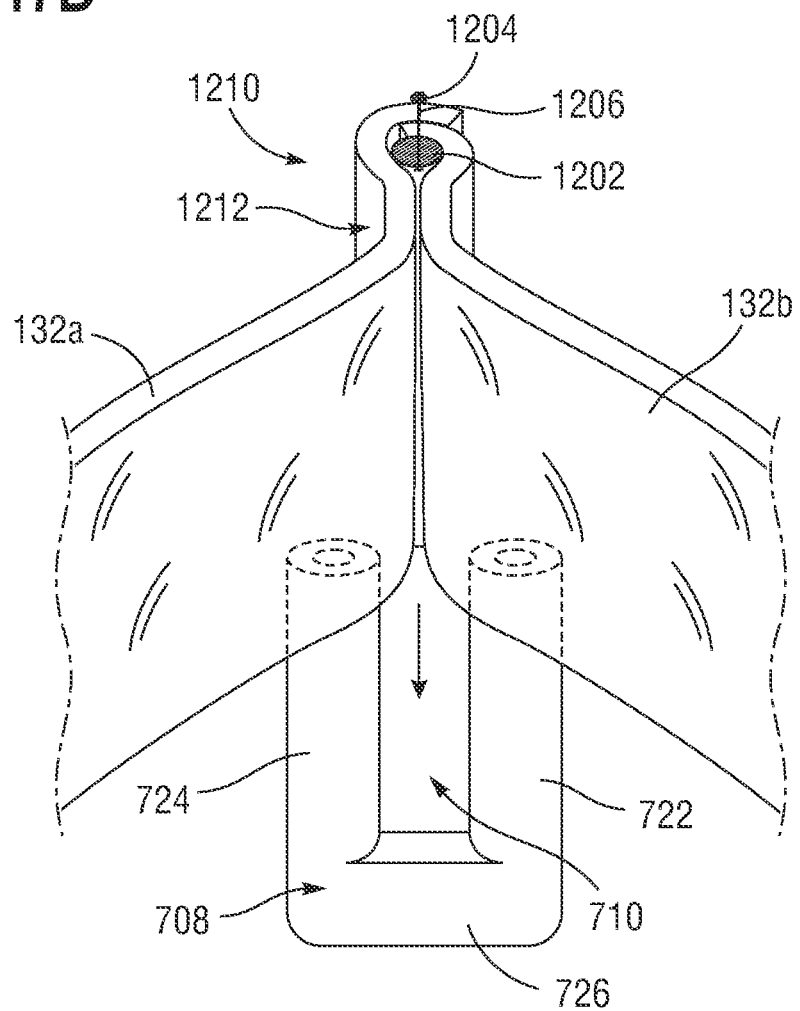
Figure 17E:
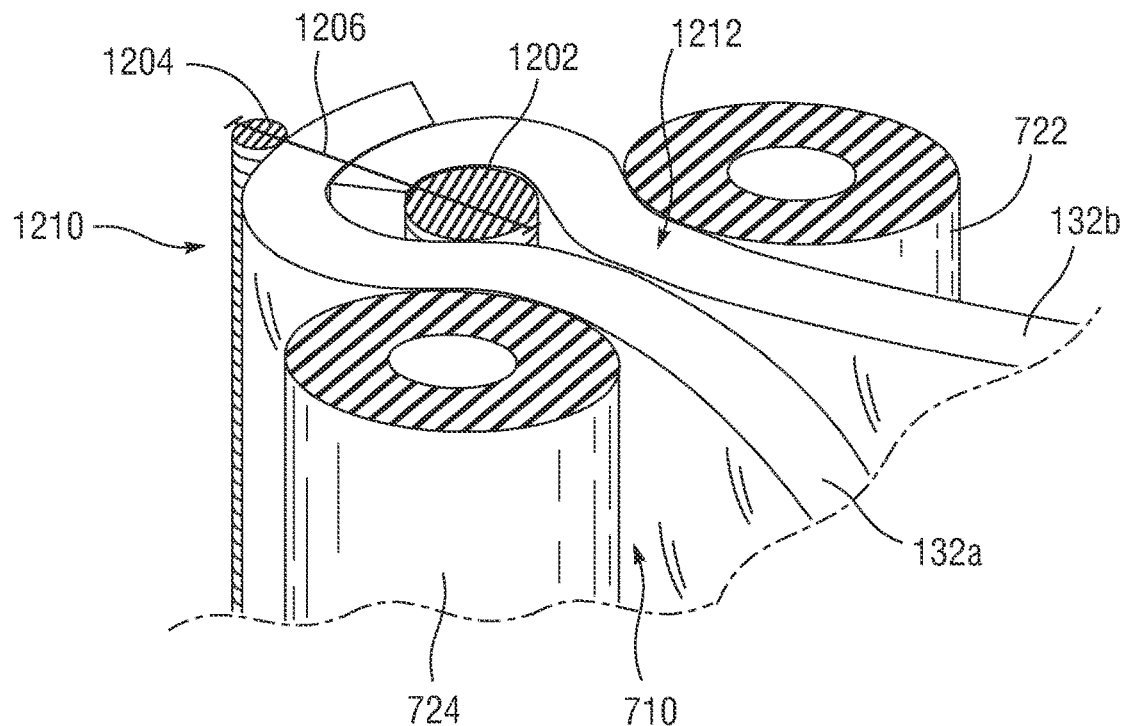

The internal wedge element 1202 is disposed along the radial direction between an outer end of the leaflet tabs and the remainder of the leaflets, thereby forming the commissure tab assembly with a radially outer portion 1210 having an increased width as compared to an adjacent radially inner portion 1212. As shown in FIGS. 17D-17E, the preassembled commissure tab assembly can then be inserted into the open window 710 of the proximal support member 708. For example, the commissure tab assembly can be conveyed along the axial direction of the annular frame from the proximal end toward the distal end.

The increased width portion 1210 of the commissure tab assembly can be disposed on a radially outer side of support member 708, with the radially inner portion 1212 being disposed within window 710. The increased width of the commissure tab assembly portion 1210 may be greater than a width of the radially outer end of window 710. For example, the thickness, $D_w$, of the internal wedge element 1202 combined with the width, $W_L$, of each leaflet tab 132a, 132b can be greater than a width of window 710 along the circumferential direction of the frame (e.g., $D_w + 2 \times W_L$ > width of window 710). Thus, the commissure tab assembly can be prevented, or at least restrained, from passing inward through window 710 (e.g., radially inward toward a centerline of the frame 102) by interaction between the increased width portion 1210 of the commissure tab assembly and window 710.

Installing the commissures tab assembly of the leaflets to the support member 708 in this manner can provide several advantages. For example, the configuration illustrated in FIGS. 17A-17E can allow all or substantially all of the commissure tab assembly to be pre-assembled in a flat configuration prior to installation to the frame 102. The use of secondary wedge element 1204 can also avoid the use of a coupling member, which may simplify fabrication and/or reduce material costs. Attachment of the assembly to the frame 102 may be relatively simple, involving only axially sliding the commissure tab assembly into the open window 710 (e.g., slot open toward an axial end of the valve) of the support member 708. This can, for example, make assembling a prosthetic valve easier, improve manufacturing throughput, and/or improve quality.

In some embodiments, the leaflet tabs can be wrapped around one or more internal wedge elements, with the wrapped tab portions extending back through the support member window. The leaflet tabs can be initially disposed together, and wedge elements disposed outside the tabs (e.g., with the tabs therebetween). The wedge elements and tabs can be connected together by one or more sutures, and the leaflet tabs can be wrapped around the wedge elements to form the commissure tab assembly. The commissure tab assembly can then be inserted into the open window of a support member.

Figure 18A:
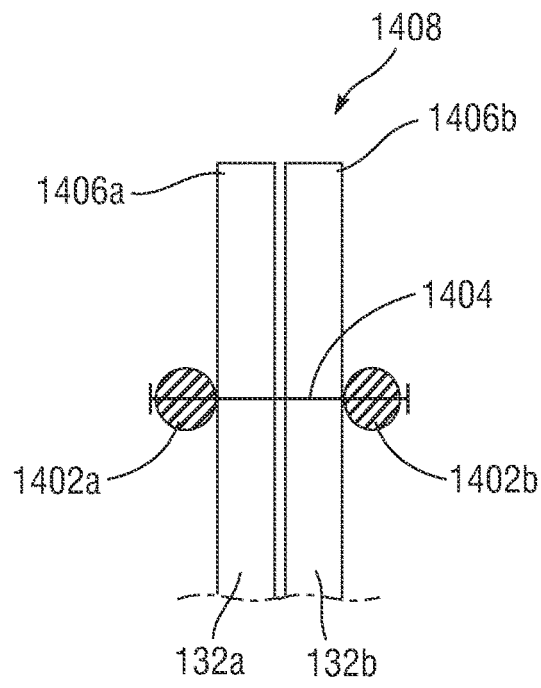
FIGS. 18A-18D are various views illustrating sequential stages in assembling a commissure tab assembly to an open window of a support member, according to a thirteenth example.
Figure 18B:
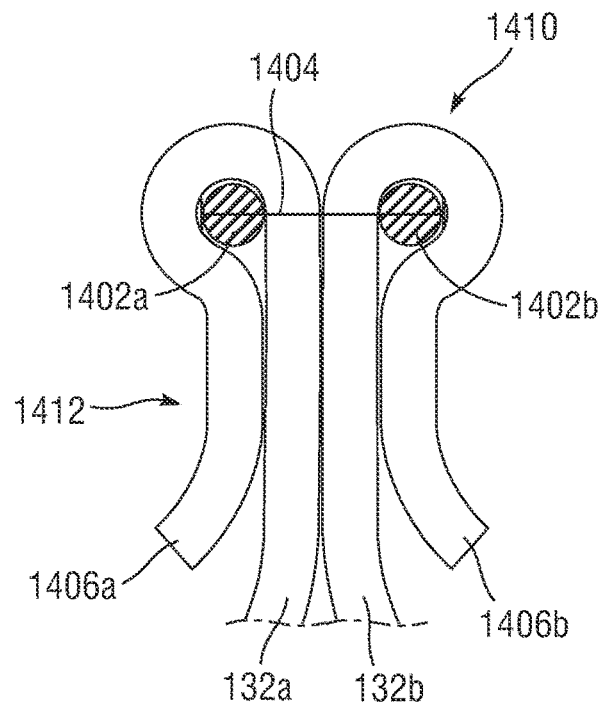

For example, FIGS. 18A-18D illustrate a thirteenth embodiment of installing a commissure tab assembly 1408 to a support member 708. Referring initially to FIGS. 18A-18B, the commissure tab assembly can be formed by disposing tabs 132a, 132b of adjacent leaflets 130a, 130b together. One or more wedge elements 1402a, 1402b can be disposed on opposite sides of the tabs 132a, 132b. For example, the wedge element 1402 can be a substantially U-shaped member with legs portions 1402a, 1402b. For example, the wedge element 1402 can be a flexible member, such as a suture, that is bent from a substantially straight initial configuration to a U-shaped configuration. Alternatively, each leg portion 1402a, 1402b may instead be a separate wedge element. The wedge element 1402a, 1402b can be formed of any biocompatible material or structure, for example, a relatively thick polymer suture or cable (e.g., polyester suture, such as Ethibond), folded piece of cloth, or any other structure.

The wedge elements 1402a, 1402b and tabs 132a, 132b can be joined together by stitching, for example, via one or more first stitches 1404 (e.g., suture loops). After stitching, free ends 1406a, 1406b of the tabs 132a, 132b can be rotated away from each other to wrap around each respective wedge element 1402a, 1402b, thereby forming a pocket that encloses each tab respectively, as shown in FIG. 18B. Alternatively, the wrapping of free ends 1406a, 1406b can occur prior to stitching, such that the first stitch 1404 extends through the wrapped portions of the tabs 132a, 132b as well as the wedge elements 1402a, 1402b and the portions of the tabs 132a, 132b between the wedge elements 1402a, 1402b.

Each wedge element 1402a, 1402b is disposed along the radial direction between an outermost end of the commissure tab assembly and the remainder of the leaflets, thereby forming the commissure tab assembly with a radially outer portion 1410 having an increased width as compared to an adjacent radially inner portion 1412. Moreover, the folded back free end 1406a, 1406b of the tabs can extend back along the corresponding tab to form the radially inner portion 1412 have a width that is four times the thickness of each leaflet tab.

Figure 18C:
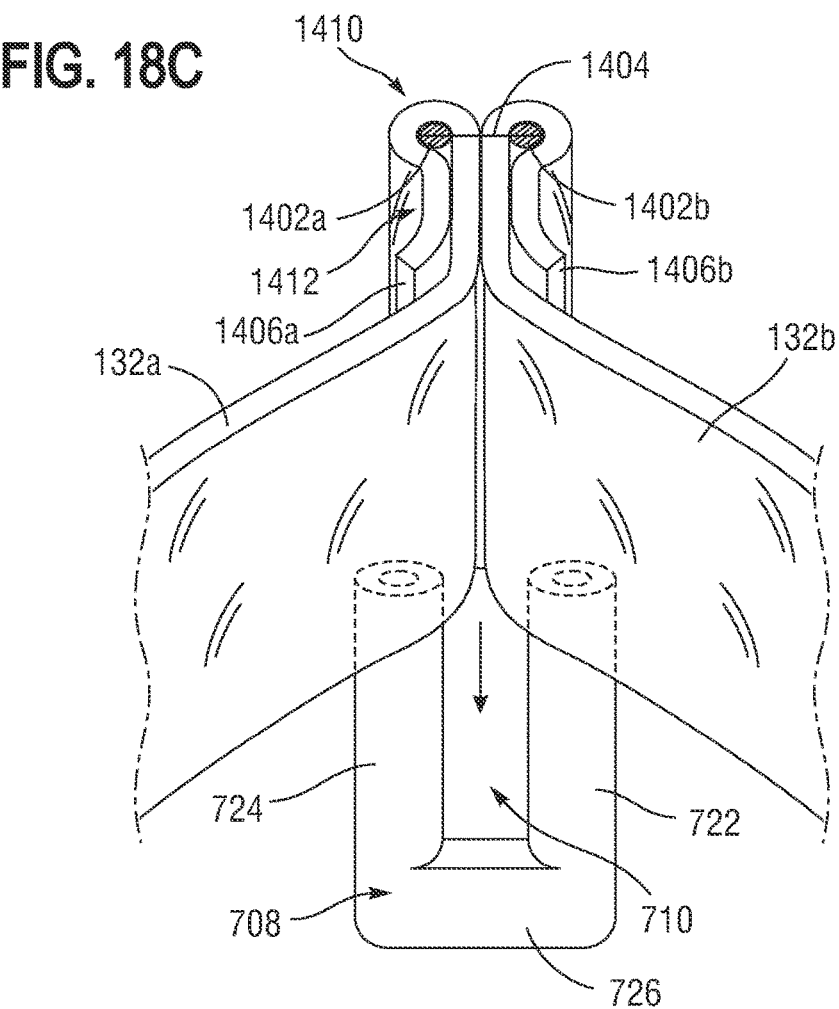
Figure 18D:
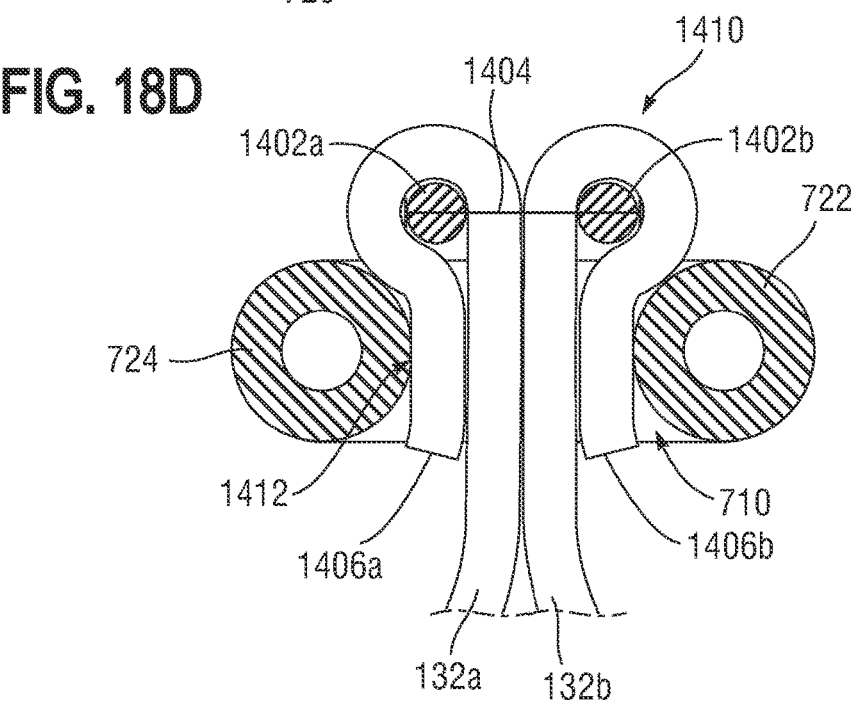

As shown in FIGS. 18C-18D, the preassembled commissure tab assembly can then be inserted into the open window 710 of the proximal support member 708. For example, the commissure tab assembly can be conveyed along the axial direction of the annular frame from the proximal end toward the distal end. The increased width portion 1410 of the commissure tab assembly can be disposed on a radially outer side of support member 708, with the radially inner portion 1412 being disposed within window 710. The increased width of the commissure tab assembly portion 1410 may be greater than a width of the radially outer end of window 710. For example, the thickness, $D_w$, of each wedge element 1402a, 1402b combined with the width, WI, of each leaflet tab 132a, 132b can be greater than a width of window 710 along the circumferential direction of the frame (e.g., $2 \times D_w + 4 \times W_L >$ width of window 710). Thus, the commissure tab assembly can be prevented, or at least restrained, from passing inward through window 710 (e.g., radially inward toward a centerline of the frame 102) by interaction between the increased width portion 1410 of the commissure tab assembly and window 710.

Moreover, the free ends 1406a, 1406b as part of the radially inner portion 1412 can provide a four-layer leaflet tab structure within open window 710, thereby improving the reliability of the assembly. For example, the free ends 1406a, 1406b can act as anti-abrasion portions separating the other portions of the leaflet tabs 132a, 132b from contact with tubes 722, 724 of the support member 708. In some embodiments, the free ends 1406a, 1406b may disposed at a location adjacent to a radially inner side of the window 710. For example, the wrapped ends of the leaflet tabs may be disposed so as not to extend radially inward beyond window 710, e.g., with ends 1406a, 1406b disposed at a location along the radial direction between the radially outer side of window 710 and the radially inner side of window 710.

Installing the commissures tab assembly of the leaflets to the support member 708 in this manner can provide several advantages. For example, the configuration illustrated in FIGS. 18A-18D can allow all or substantially all of the commissure tab assembly to be pre-assembled prior to installation to the frame 102. The use of a four-layer thickness within the support member window can also avoid the use of a coupling member, which may simplify fabrication and/or reduce material costs. Attachment of the assembly to the frame 102 may be relatively simple, involving only axially sliding the commissure tab assembly into the open window 710 (e.g., slot open toward an axial end of the valve) of the support member 708. This can, for example, make assembling a prosthetic valve easier, improve manufacturing throughput, and/or improve quality.

Figure 19A:
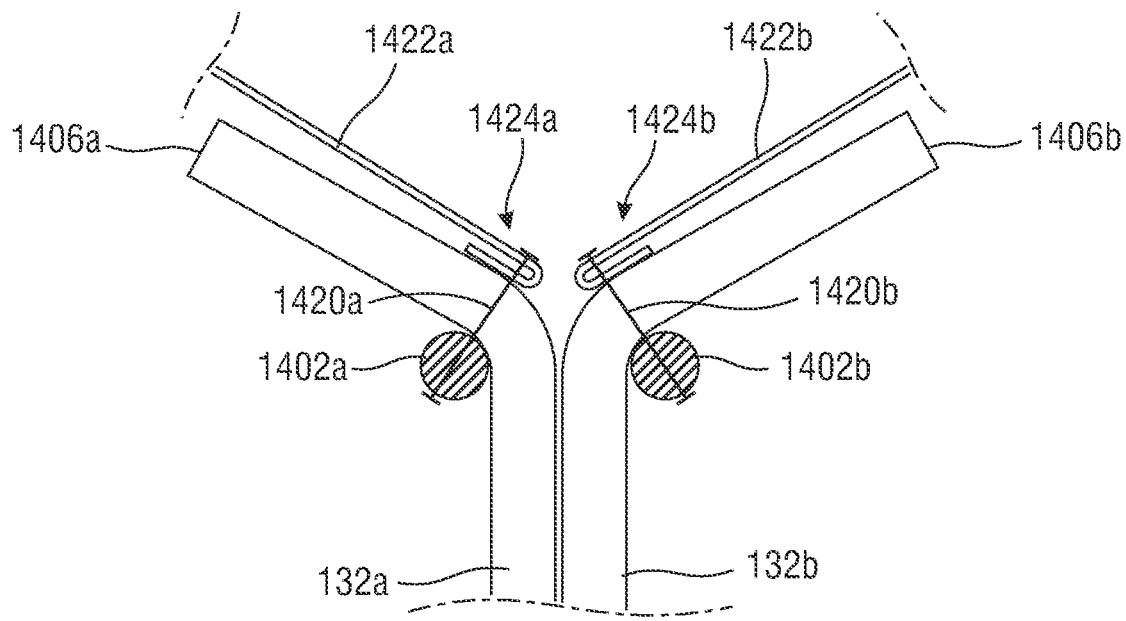
Figure 19B:
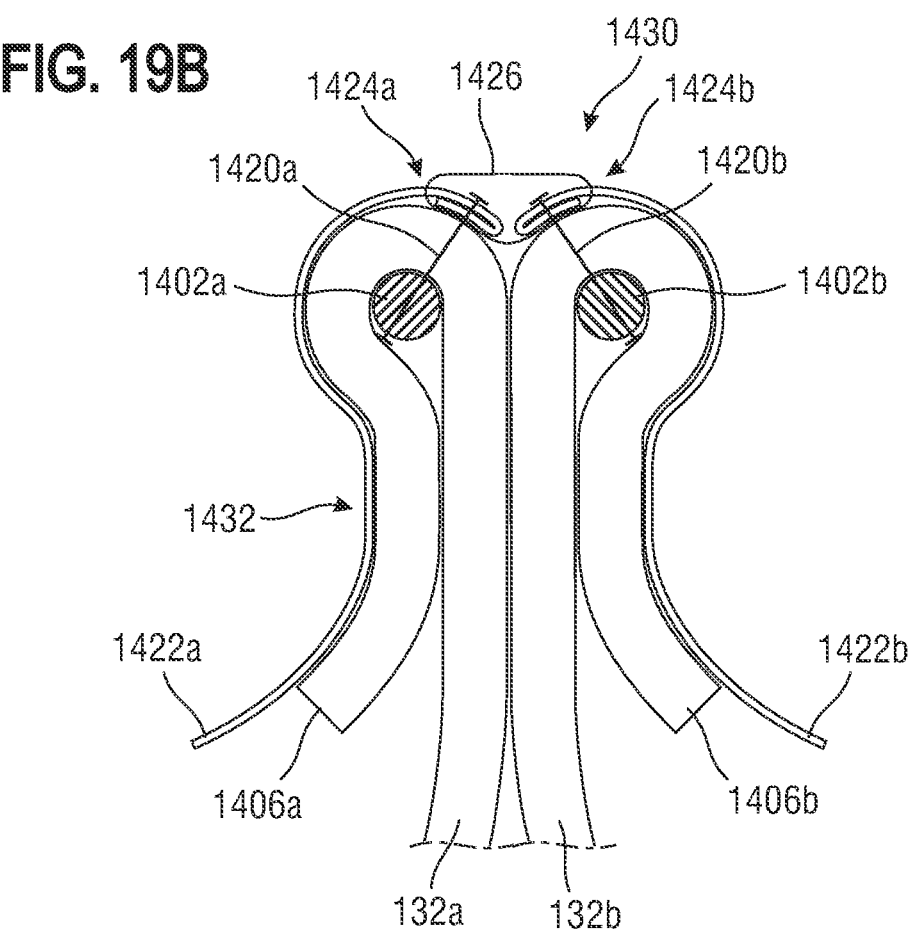

In some embodiments, one or more coupling members can be combined with the wrapping of leaflet tabs around one or more internal wedge elements. For example, FIGS. 19A-19D illustrate a fourteenth embodiment of installing a commissure tab assembly to a support member. Referring initially to FIGS. 19A-19B, the commissure tab assembly can be formed by disposing tabs 132a, 132b of adjacent leaflets 130a, 130b together. The tabs 132a, 132b can be flexed in opposite directions at their ends to form a T-shape. A coupling member 1422a, 1422b can then be disposed over a respective upper surface of T-shape formed by the leaflet tabs 132a, 132b. Alternatively, a single coupling member can be used in place of the pair of coupling members 1422a, 1422b.

One or more wedge elements 1402a, 1402b can be disposed on surfaces of the T-shape formed by tabs 132a, 132b opposite to the coupling members 1422a, 1422b. For example, the wedge element 1402 can be a substantially U-shaped member with legs portions 1402a, 1402b. For example, the wedge element 1402 can be a flexible member, such as a suture, that is bent from a substantially straight initial configuration to a U-shaped configuration. Alternatively, each leg portion 1402a, 1402b may instead be a separate wedge element. The wedge element 1402a, 1402b can be formed of any biocompatible material or structure, for example, a relatively thick polymer suture or cable (e.g., polyester suture, such as Ethibond), folded piece of cloth, or any other structure.

The wedge element 1402a, coupling member 1422a, and tabs 132a can be joined together by stitching, for example, via one or more first stitches or suture loops 1420a. Similarly, the wedge element 1402b, coupling member 1422b, and tab 132b can be joined together by stitching, for example, via one or more second stitches or suture loops 1420b. In some embodiments, the coupling members 1422a, 1422b comprise folded end portions 1424a, 1424b through which the respective sutures 1420a, 1420b are passed.

After stitching, free ends 1406a, 1406b of the tabs 132a, 132b can be rotated further away from each other to wrap around each respective wedge element 1402a, 1402b, thereby forming a pocket that encloses each tab respectively, as shown in FIG. 19B. Optionally, adjacent ends of the coupling members can be further joined together by stitching, for example, via one or more third stitches or suture loops 1426. Alternatively, the wrapping of free ends 1406a, 1406b can occur prior to stitching, such that a single stitch is used to join together the wrapped portions of the tabs 132a, 132b, the wedge elements 1402a, 1402b, the portions of the tabs 132a, 132b between the wedge elements 1402a, 1402b, and the coupling members 1422a, 1422b.

Each wedge element 1402a, 1402b is disposed along the radial direction between an outermost end of the commissure tab assembly and the remainder of the leaflets, thereby forming the commissure tab assembly with a radially outer portion 1430 having an increased width as compared to an adjacent radially inner portion 1432. Moreover, the folded back free end 1406a, 1406b of the tabs can extend back along the corresponding tab to form the radially inner portion 1432 have a width that is four times the thickness of each leaflet tab.

Figure 19D:
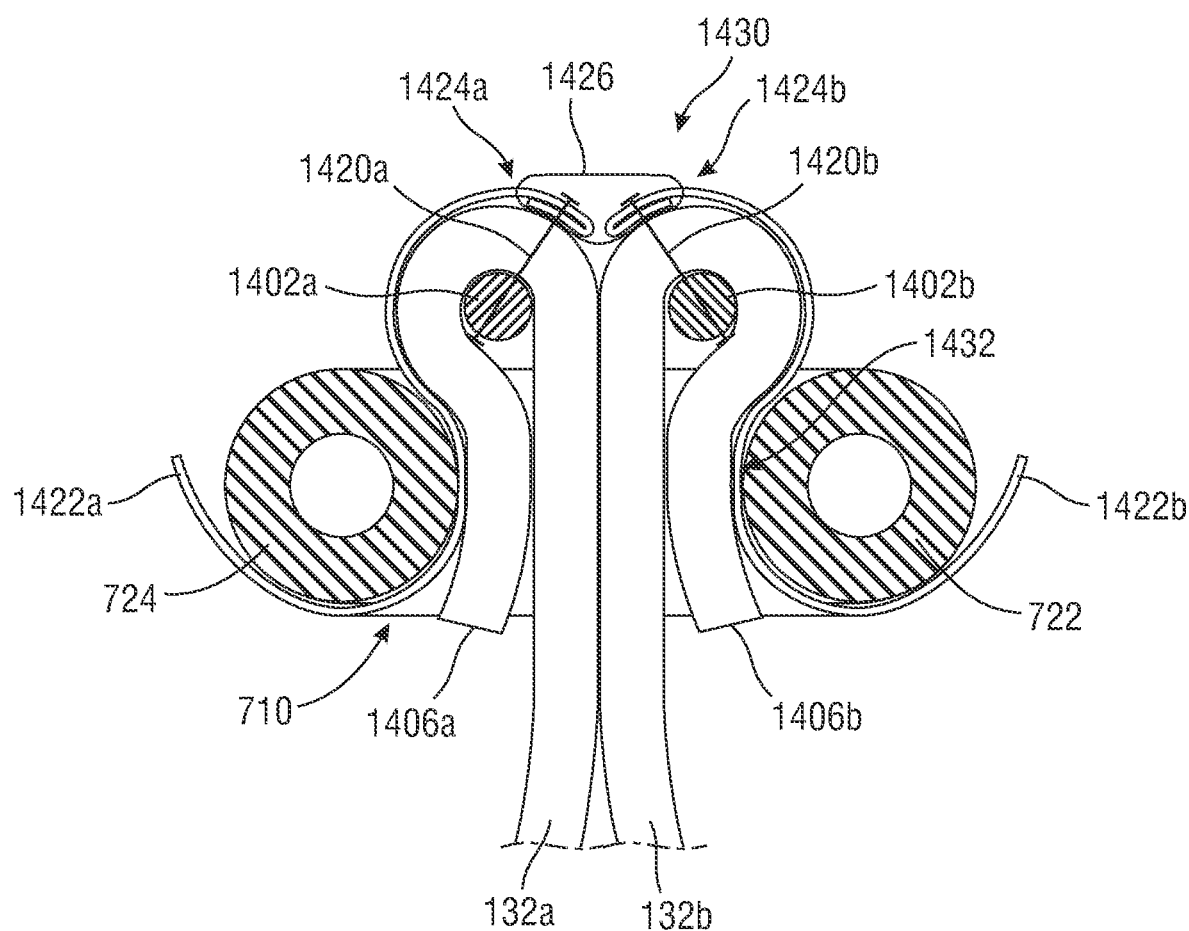

As shown in FIGS. 19C-19D, the preassembled commissure tab assembly can then be inserted into the open window 710 of the proximal support member 708. For example, the commissure tab assembly can be conveyed along the axial direction of the annular frame from the proximal end toward the distal end. The increased width portion 1430 of the commissure tab assembly can be disposed on a radially outer side of support member 708, with the radially inner portion 1432 being disposed within window 710. Once the commissure tab assembly is fully inserted into window 710, free ends of each coupling member 1422a, 1422b can be wrapped around the support member 708 (in a manner similar to that described above for FIG. 14D), passed back through window 710 (in a manner similar to that described above for FIGS. 14E-14F), or in any other manner.

The increased width of the commissure tab assembly portion 1410 may be greater than a width of the radially outer end of window 710. For example, the thickness, $D_w$, of each wedge element 1402a, 1402b combined with the thickness, t, of the coupling member 1422, and the width, $W_L$, of each leaflet tab 132a, 132b can be greater than a width of window 710 along the circumferential direction of the frame (e.g., $2 \times t + 2 \times D_w + 4 \times W_L >$ width of window 710). Thus, the commissure tab assembly can be prevented, or at least restrained, from passing inward through window 710 (e.g., radially inward toward a centerline of the frame 102) by interaction between the increased width portion 1410 of the commissure tab assembly and window 710. Moreover, the free ends 1406a, 1406b as part of the radially inner portion 1432 can provide a four-layer leaflet tab structure within open window 710, thereby improving the reliability of the assembly. For example, the free ends 1406a, 1406b and coupling members 1422a, 1422b can act as anti-abrasion portions separating the other portions of the leaflet tabs 132a, 132b from contact with tubes 722, 724 of the support member 708.

Installing the commissures tab assembly of the leaflets to the support member 708 in this manner can provide several advantages. For example, the configuration illustrated in FIGS. 19A-19D can allow all or substantially all of the commissure tab assembly to be pre-assembled prior to installation to the frame 102. Attachment of the assembly to the frame 102 may be relatively simple, involving only axially sliding the commissure tab assembly into the open window 710 (e.g., slot open toward an axial end of the valve) of the support member 708 and optional securing of free ends of the coupling member. This can, for example, make assembling a prosthetic valve easier, improve manufacturing throughput, and/or improve quality.

As noted above, any of the disclosed wedge elements (whether internal, external, or otherwise) can be formed from a relatively thick, multi-filament or monofilament suture, yarn or cable (e.g., a braided, polyester suture, such as an Ethibond suture), a piece of cloth or fabric folded one or more times to increase its thickness, or any other structure. For example, the disclosed wedge elements, or sutures coupled thereto, can be formed of a material that does not encourage tissue ingrowth, such as ultra-high molecular weight polyethylene (UHMPE), polyethylene terephthalate (PET), polyurethane (PU), or polytetrafluoroethylene (PTFE). Alternatively or additionally, any other material that is minimally porous, configured to prevent or minimize neo-vascularization, or does not allow tissue anchoring can be used for the disclosed wedge elements. Alternatively or additionally, the disclosed wedge elements can be a coated or laminated polymeric material. In some embodiments, the material for the disclosed wedge elements can be a polymer material that is processed in a manner, or otherwise configured, to reduce the likelihood to tissue ingrowth. For example, if exposure of the material to certain levels of heat may induce thrombogenicity, the materials for the disclosed wedge elements may be processed in a manner that avoids or reduces such heating steps.

Although the description above has focused on the installation of commissure tab assemblies to windows formed in the support member itself, embodiments of the disclosed subject matter are not limited thereto. Rather, in some embodiments, the window may be formed by another member coupled to the support member (or the actuator). For example, a wireform (e.g., bent piece of wire) or clamp can be attached to the support member to form an open or closed window, into which any of the commissure tab assemblies disclosed herein can be installed. Further details regarding wireforms, can be found, for example, in International Publication No. WO/2020/102487, which is incorporated herein by reference.

Figure 20C:
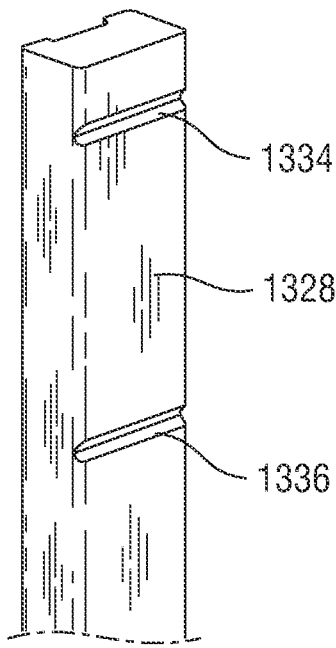
FIG. 20C is a rear perspective view of the support member corresponding to FIG. 20A but without the wireform installed.
Figure 20D:
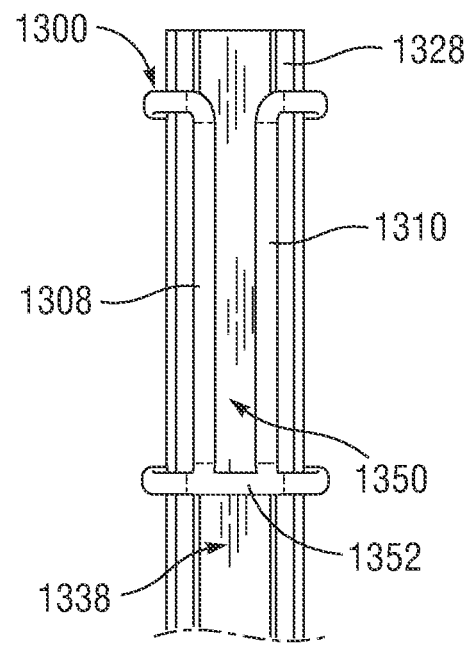

For example, a wireform 1300 can be formed by bending a piece of wire (e.g., a straight piece of wire) into the shape shown in FIG. 20D and securing a connection portion 1352 to the free ends of the wire, such as by welding. In alternative embodiments, other techniques and/or methods can be used to form a wireform 1300. For example, a clamp can be formed by molding (e.g., injection molding), machining (e.g., laser cutting), or 3D printing.

FIGS. 20A-20D are various views illustrating the wireform 1300 situated on an actuator component 1328 (e.g., support member). The actuator component 1328 can be, for example, the outer member of an actuator of a mechanically-expandable prosthetic heart valve, similar to the outer members of the actuator 104 of the prosthetic valve 100 of FIG. 1A. In the illustrated embodiment, the actuator component 1328 can have a rectangular cross-section, although in other embodiments the actuator component may have a round cross-section, or a cross-section having any other selected shape.

Collar portions 1304, 1306 of the wireform 1300 can be shaped to correspond to the cross-sectional shape of the actuator component 1328 taken in a plane perpendicular to the longitudinal axis 1337 of the actuator component. The wireform 1300 can be positioned on the actuator component 1328 such that the clamping members 1308 and 1310 are situated against a radially inward-facing surface of the actuator component 1328, and the rear portions 1316, 1318 are disposed around a radially outward-facing surface 1332 (FIG. 20A) of the actuator component.

Figure 20E:
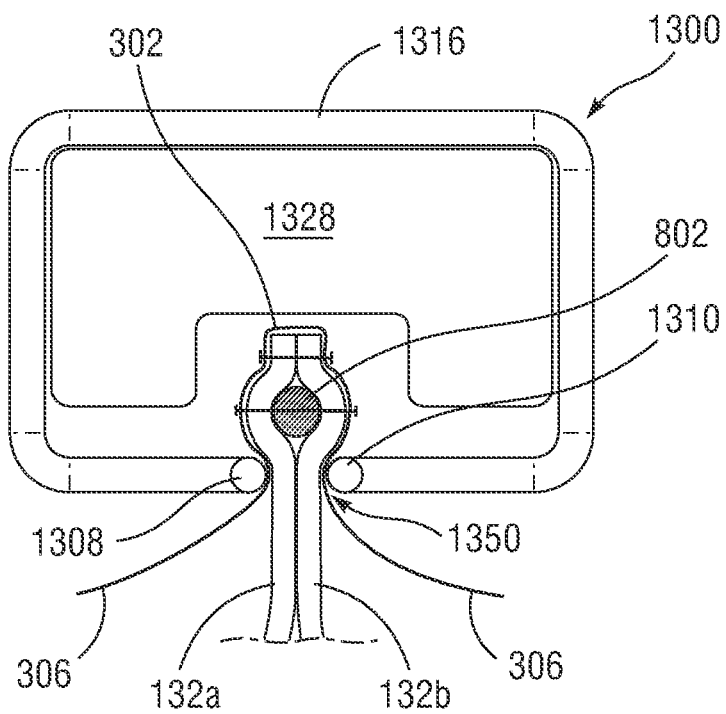
FIG. 20E is a top plan view illustrating a commissure tab assembly installed in the commissure window formed using the wireform of FIG. 20D.

Referring to FIG. 20C, in certain embodiments the actuator components 1328 can comprise grooves or channels 1334, 1336 configured to receive the portions 1316, 1318 of the wireform 1300. In some embodiments, the radially inward surface of the actuator component 1328 can define an axially-extending groove or channel 1338, as shown in FIGS. 20D-20E. Together, the axially extending members 1308, 1310 and the connecting portion 1352 can form an open window 1350 into which a commissure tab assembly can be inserted, as illustrated in FIG. 20E. Further details regarding the construction and use of wireforms, can be found, for example, in International Publication No. WO/2020/102487, which is incorporated herein by reference.

Although particular shapes and configurations for the support members and windows have been illustrated in the figures and described in the examples above, embodiments of the disclosed subject matter are not limited thereto. Indeed, in some embodiments, the tubes forming the window of the support member may have a cross-sectional geometry (e.g., in a plane perpendicular to the longitudinal axis of the annular frame) that is circular, oval, hexagonal, octagonal, or any other shape. In some embodiments, the tubes of the support member forming the open or closed windows may have lumens extending therethrough. In other embodiments, the support member tubes may be substantially solid throughout their thickness. In some embodiments, the support member may be substantially symmetric about its centerline, such that the tubes on opposite sides of the window have a similar geometry, for example, as illustrated in FIG. 11. In other embodiments, the support member may be asymmetrical about its centerline, such that the tubes on opposite sides of the window have a different geometry, for example, as illustrated in FIG. 6C.

Additional Description of Embodiments of Interest

Clause 1. An assembly method for a prosthetic heart valve, the method comprising:
  disposing tabs of adjacent leaflets together, each leaflet having a pair of tabs on opposite sides with respect to a centerline thereof;
  coupling together portions of the tabs of the adjacent leaflets to form a commissure tab assembly, the coupled portions being spaced from ends of the tabs;
  conveying the commissure tab assembly through a closed window of a support member of an expandable frame of the prosthetic heart valve, the conveying being along a radial direction of the expandable frame from a radially-inner side of the closed window to a radially-outer side of the closed window; and
  inserting a wedge between the tabs of the commissure tab assembly at a first location along the radial direction between the coupled portions and the radially-outer side of the closed window, a width along a circumferential direction of the annular frame for a portion of the commissure tab assembly being increased by the wedge,
  wherein the increased width of the commissure tab assembly portion is greater than a width along the circumferential direction for a corresponding portion of the radially-outer side of the closed window, and
  wherein movement of the commissure tab assembly inward along the radial direction is restrained by interaction of the increased width portion of the commissure tab assembly with the corresponding portion of the closed window of the support member.

Clause 2. The method of clause 1, wherein the coupling together portions of the tabs to form the commissure tab assembly comprises stitching together the portions of the tabs using one or more first sutures.

Clause 3. The method of any one of clauses 1-2, wherein the expandable frame of the prosthetic heart valve comprises an annular frame having an inflow end and an outflow end separated from the inflow end along an axial direction of the frame, and/or the support member is coupled to the expandable frame.

Clause 4. The method of any one of clauses 1-3, wherein the expandable frame is radially collapsible and expandable between a radially-compressed configuration and a radially-expanded configuration.

Clause 5. The method of any one of clauses 1-4, wherein:
  the disposing tabs of adjacent leaflets comprises providing a coupling member over exposed surface portions of the pair of tabs of the adjacent leaflets; and
  the stitching comprises stitching together the coupling member and the tabs of the adjacent leaflets via the first suture to form the commissure tab assembly.

Clause 6. The method of any one of clauses 1-5, wherein:
  the providing the coupling member is such that a portion of the coupling member is arranged between facing surfaces of the pair of tabs so as to form a collapsed pocket portion; and
  the inserting the wedge comprises expanding the pocket portion and disposing the wedge therein.

Clause 7. The method of any one of clauses 1-6, wherein, after the conveying, free ends of the coupling member extend from the radially-inner side of the closed window, the method further comprising:
  wrapping each free end around an adjacent portion of the support member toward the radially-outer side of the closed window; and
  stitching together the free ends and the commissure tab assembly via a second suture spaced from the ends of the tabs,
  wherein the first suture is between the wedge and the second suture along the radial direction.

Clause 8. The method of any one of clauses 1-7, wherein:
  after the inserting, one or more ends of the wedge extend axially above or below the commissure tab assembly, and
  the method further comprises inserting the one or more ends of the wedge between the tabs of the commissure tab assembly at a second location along the radial direction between the first location and the ends of the tabs.

Clause 9. The method of any one of clauses 1-8, wherein the second location is between the first suture and the second suture along the radial direction.

Clause 10. The method of any one of clauses 1-9, wherein the coupling member comprises a cloth or fabric.

Clause 11. The method of any one of clauses 1-10, wherein each wedge comprises a braided polymer suture or cable.

Clause 12. The method of any one of clauses 1-11, wherein each window comprises an opening or channel defined by a wireform coupled to the support member.

Clause 13. The method of any one of clauses 1-12, wherein the valvular structure is a bicuspid structure with two leaflets and two commissure tab assemblies, and the commissure support posts are on diametrically opposite sides of the annular frame from each other.

Clause 14. The method of any one of clauses 1-12, wherein the valvular structure is a tricuspid structure with three leaflets and three commissure tab assemblies, and the commissure support posts are equally spaced around a circumference of the annular frame.

Clause 15. The method of any one of clauses 1-14, wherein the frame is formed of a plastically-expandable material or a self-expanding material.

Clause 16. The method of any one of clauses 1-14, wherein the frame comprises an array of angled struts connected together by one or more pivot joints.

Clause 17. An assembly method for a prosthetic heart valve, the method comprising:
- disposing tabs of adjacent leaflets together, each leaflet having a pair of tabs on opposite sides with respect to a centerline thereof;
- providing a coupling member over exposed surface portions of the pair of tabs of the adjacent leaflets, the coupling member extending beyond ends of the tabs to form a collapsible pocket portion;
- stitching together the coupling member and the tabs of the adjacent leaflets via a first suture spaced from the ends of the tabs to form a commissure tab assembly, the first suture being in a loose state;
- inserting one or more external wedges between a surface of the pocket portion of the coupling member and the loose first suture;
- conveying the commissure tab assembly and the one or more external wedges through a closed window of a support member of an expandable frame of the prosthetic heart valve, the conveying being along a radial direction of the expandable frame from a radially-inner side of the closed window to a radially-outer side of the closed window; and
- tightening the first suture such that the one or more external wedges are arranged along the radial direction with the pair of tabs and the coupling member therebetween, an effective width along a circumferential direction of the annular frame for a portion of the commissure tab assembly being increased by the one or more external wedges,
- wherein a width along a circumferential direction of the one or more external wedges and the pocket portion of the coupling member in a collapsed state is less than a width along the circumferential direction for the closed window,
- wherein the effective width for the portion of the commissure tab assembly is greater than a width along the circumferential direction for a corresponding portion of the closed window, and
- wherein movement of the commissure tab assembly inward along the radial direction is restrained by interaction of the portion of the commissure tab assembly with the corresponding portion of the closed window of the support member.

Clause 18. The method of clause 17, wherein the expandable frame of the prosthetic heart valve comprises an annular frame having an inflow end and an outflow end separated from the inflow end along an axial direction of the frame, and/or the support member is coupled to the expandable frame.

Clause 19. The method of any one of clauses 17-18, wherein the expandable frame is radially collapsible and expandable between a radially-compressed configuration and a radially-expanded configuration.

Clause 20. The method of any one of clauses 17-19, wherein the one or more external wedges comprise separate wedge members.

Clause 21. The method of any one of clauses 17-19, wherein the one or more external wedges comprises a single-continuous wedge member.

Clause 22. The method of clause 21, wherein the single-continuous wedge member is substantially U-shaped.

Clause 23. The method of any one of clauses 17-22, wherein the coupling member comprises a cloth or fabric.

Clause 24. The method of any one of clauses 17-23, wherein each wedge comprises a braided polymer suture or cable.

Clause 25. The method of any one of clauses 17-24, wherein each window comprises an opening or channel that extends through a thickness of the support member along the radial direction.

Clause 26. The method of any one of clauses 17-25, wherein each window comprises an opening or channel defined by a wireform coupled to the support member.

Clause 27. An assembly method for a prosthetic heart valve, the method comprising:
- disposing tabs of adjacent leaflets together, each leaflet having a pair of tabs on opposite sides with respect to a centerline thereof;
- providing a coupling member over exposed surface portions of the pair of tabs of the adjacent leaflets;
- stitching together the tabs of the adjacent leaflets and the coupling member via a first suture spaced from ends of the tabs;
- disposing one or more external wedges in contact with first portions of the coupling member;
- further stitching together the tabs, the coupling member, and the one or more external wedges via a second suture to form a commissure tab assembly;
- conveying the commissure tab assembly through a closed window of a support member of an expandable frame of the prosthetic heart valve, the conveying being along a radial direction of the expandable frame from a radially-inner side of the closed window to a radially-outer side of the closed window; and
- inserting an internal wedge between the tabs of the commissure tab assembly at a first location along the radial direction between the first suture and the radially-outer side of the closed window, a width along a circumferential direction of the annular frame for a first portion of the commissure tab assembly being increased by the wedge,
- wherein the first suture is between the ends of the tabs and the second suture along the radial direction,
- wherein the increased width first portion of the commissure tab assembly is greater than a width along the circumferential direction for a corresponding portion of the radially-outer side of the closed window,
- wherein movement of the commissure tab assembly inward along the radial direction is restrained by interaction of the first portion of the commissure tab assembly with the corresponding portion of the closed window of the support member
- wherein a second portion of the commissure tab assembly, where the one or more external wedges is disposed, has a width that is greater than a width along the circumferential direction for a corresponding portion of the radially-inner side of the closed window, and wherein movement of the commissure tab assembly outward along the radial direction is restrained by interaction of the second portion of the commissure tab assembly with the corresponding portion of the closed window of the support member.

Clause 28. The method of clause 27, wherein a length of the one or more external wedges along an axial direction of the annular frame is greater than a length of the internal wedge along the axial direction.

Clause 29. The method of any one of clauses 27-28, wherein the disposing one or more external wedges includes wrapping each free end of the coupling member around a respective one of the external wedges, and the second suture couples together each wrapped free end of the coupling member, each external wedge, each first portion of the coupling member, and each leaflet tab.

Clause 30. The method of any one of clauses 27-29, wherein the ends of the leaflet tabs are disposed along the radial direction between the one or more external wedges and the radially-outer side of the closed window.

Clause 31. The method of any one of clauses 27-30, wherein the expandable frame of the prosthetic heart valve comprises an annular frame having an inflow end and an outflow end separated from the inflow end along an axial direction of the frame, and/or the support member is coupled to the expandable frame.

Clause 32. The method of any one of clauses 27-31, wherein the expandable frame is radially collapsible and expandable between a radially-compressed configuration and a radially-expanded configuration.

Clause 33. The method of any one of clauses 27-32, wherein the one or more external wedges comprise separate wedge members.

Clause 34. The method of any one of clauses 27-32, wherein the one or more external wedges comprises a single-continuous wedge member.

Clause 35. The method of clause 34, wherein the single-continuous wedge member is substantially U-shaped.

Clause 36. The method of any one of clauses 27-35, wherein the coupling member comprises a cloth or fabric.

Clause 37. The method of any one of clauses 27-36, wherein each wedge comprises a braided polymer suture or cable.

Clause 38. The method of any one of clauses 27-37, wherein each window comprises an opening or channel that extends through a thickness of the support member along the radial direction.

Clause 39. The method of any one of clauses 27-38, wherein each window comprises an opening or channel defined by a wireform coupled to the support member.

Clause 40. An assembly method for a prosthetic heart valve, the method comprising:
disposing tabs of adjacent leaflets together, each leaflet having a pair of tabs on opposite sides with respect to a centerline thereof;
providing a coupling member over exposed surface portions of the pair of tabs of the adjacent leaflets, the coupling member extending beyond ends of the tabs to form a collapsible pocket portion;
disposing one or more external wedges in contact with first portions of the coupling member;
stitching together the tabs, the coupling member, and the one or more external wedges via a first suture to form a commissure tab assembly;
conveying at least the collapsible pocket portion of the coupling member through a closed window of a support member of an expandable annular frame of the prosthetic heart valve, the conveying being along a radial direction of the expandable annular frame from a radially-inner side of the closed window to a radially-outer side of the closed window; and
expanding the pocket portion of the coupling member and inserting an internal wedge into the expanded pocket portion at a first location along the radial direction between coupling member and the radially-outer side of the closed window,
wherein a combined width of the coupling member and the internal wedge along a circumferential direction of the annular frame is greater than a width along the circumferential direction for a corresponding portion of the radially-outer side of the closed window,
wherein movement of the commissure tab assembly inward along the radial direction is restrained by interaction of the coupling member and the internal wedge with the corresponding portion of the closed window of the support member,
wherein a portion of the commissure tab assembly, where the one or more external wedges is disposed, has a width that is greater than a width along the circumferential direction for a corresponding portion of the radially-inner side of the closed window, and
wherein movement of the commissure tab assembly outward along the radial direction is restrained by interaction of the portion of the commissure tab assembly with the corresponding portion of the closed window of the support member.

Clause 41. The method of clause 40, wherein a length of the one or more external wedges along an axial direction of the annular frame is greater than a length of the internal wedge along the axial direction.

Clause 42. The method of any one of clauses 40-41, wherein the disposing one or more external wedges includes wrapping each free end of the coupling member around a respective one of the external wedges, and the second suture couples together each wrapped free end of the coupling member, each external wedge, each first portion of the coupling member, and each leaflet tab.

Clause 43. The method of any one of clauses 40-42, wherein the ends of the leaflet tabs are disposed along the radial direction between the one or more external wedges and the radially-outer side of the closed window.

Clause 44. The method of any one of clauses 40-43, wherein the expandable frame of the prosthetic heart valve comprises an annular frame having an inflow end and an outflow end separated from the inflow end along an axial direction of the frame, and/or the support member is coupled to the expandable frame.

Clause 45. The method of any one of clauses 40-44, wherein the expandable frame is radially collapsible and expandable between a radially-compressed configuration and a radially-expanded configuration.

Clause 46. The method of any one of clauses 40-45, wherein the one or more external wedges comprise separate wedge members.

Clause 47. The method of any one of clauses 40-45, wherein the one or more external wedges comprises a single-continuous wedge member.

Clause 48. The method of clause 47, wherein the single-continuous wedge member is substantially U-shaped.

Clause 49. The method of any one of clauses 40-48, wherein the coupling member comprises a cloth or fabric.

Clause 50. The method of any one of clauses 40-49, wherein each wedge comprises a braided polymer suture or cable.

Clause 51. The method of any one of clauses 40-50, wherein each window comprises an opening or channel that extends through a thickness of the support member along the radial direction.

Clause 52. The method of any one of clauses 40-51, wherein each window comprises an opening or channel defined by a wireform coupled to the support member.

Clause 53. An assembly method for a prosthetic heart valve, the method comprising:
- disposing tabs of adjacent leaflets together, each leaflet having a pair of tabs on opposite sides with respect to a centerline thereof;
- disposing an internal wedge between facing surfaces of the tabs of the adjacent leaflets;
- stitching together the tabs and the internal wedge via at least one first suture to form a commissure tab assembly;
- stitching together the tabs via a second suture, the second suture being disposed between the internal wedge and ends of the tabs;
- conveying a first portion of the commissure tab assembly into a window of a support member of an expandable frame of the prosthetic heart valve, the conveying being along an axial direction of the expandable frame from a proximal, open end of the window to a distal end of the window,
- wherein, at a radial location corresponding to the internal wedge, the commissure tab assembly has a second portion with an increased width along a circumferential direction of the expandable frame as compared to the first portion,
- wherein the increased width of the second portion is greater than a width along the circumferential direction for a corresponding portion of a radially-outer side of the window, and
- wherein movement of the commissure tab assembly inward along a radial direction of the frame is restrained by interaction of the second portion of the commissure tab assembly with the corresponding portion of the window of the support member.

Clause 54. The method of clause 53, wherein the expandable frame of the prosthetic heart valve comprises an annular frame having an inflow end and an outflow end separated from the inflow end along the axial direction of the frame, and/or the support member is coupled to the expandable frame.

Clause 55. The method of any one of clauses 53-54, wherein the expandable frame is radially collapsible and expandable between a radially-compressed configuration and a radially-expanded configuration.

Clause 56. The method of any one of clauses 53-55, further comprising:
- prior to the stitching together the tabs and the internal wedge, disposing one or more external wedges on sides of the tabs opposite to the internal wedge,
- wherein the stitching together the tabs and the internal wedge includes stitching together the tabs, the internal wedge and the one or more external wedges together via the at least one first suture.

Clause 57. The method of any one of clauses 53-56, wherein, after the conveying, the one or more external wedges are disposed along a radial direction of the frame adjacent to or in contact with the support member at the radially outer side of the window.

Clause 58. The method of any one of clauses 53-57, wherein:
- the disposing tabs of adjacent leaflets comprises providing a coupling member over surface portions of the pair of tabs of the adjacent leaflets,
- the internal wedge is disposed between facing surfaces of the coupling member and the facing surfaces of the tabs,
- the stitching together the tabs and internal wedge comprises stitching together the coupling member, the tabs, and the internal wedge via the at least one first suture, and
- the stitching together the tabs comprises stitching together the coupling member and the tabs via the second suture.

Clause 59. The method of any one of clauses 53-58, wherein the at least one first suture is two first sutures, one of the tabs, the internal wedge, and one of the external wedges being coupled together by one of the first sutures, and the other of the tabs, the internal wedge, and the other of the external wedges being coupled together by the other of the first sutures.

Clause 60. The method of any one of clauses 53-57, wherein:
- the disposing tabs of adjacent leaflets comprises providing a coupling member over surface portions of the pair of tabs of the adjacent leaflets,
- the internal wedge is disposed between the facing surfaces of the tabs without contacting the coupling member,
- the stitching together the tabs and internal wedge comprises stitching together the coupling member, the tabs, and the internal wedge via the at least one first suture, and
- the stitching together the tabs comprises stitching together the coupling member and the tabs via the second suture.

Clause 61. The method of any one of clauses 53-60, wherein the at least one first suture is a single first suture that couples together the coupling member, the tabs, and the internal wedge.

Clause 62. The method of any one of clauses 58-61, wherein:
- after the conveying, free ends of the coupling member extend from the radially-inner side of the window,
- the method further comprises wrapping each free end around an adjacent portion of the support member toward the radially-outer side of the window, and
- the stitching together the tabs is after the conveying and comprises stitching together the free ends, the tabs, and portions of the coupling member between the free ends via the second suture.

Clause 63. The method of any one of clauses 58-61, wherein:
- after the conveying, free ends of the coupling member are folded over to extend away from the radially-inner side of the window, and
- the stitching together the tabs is after the conveying and comprises stitching together the free ends, the tabs, and portions of the coupling member between the free ends via the second suture.

Clause 64. The method of any one of clauses 58-61, wherein:
- after the conveying, free ends of the coupling member are folded over to form pockets at the radially-inner side of the window and to extend through the window to the radially-outer side,
- the method further comprises inserting one or more external wedges into the pockets formed by the folded free ends, and movement of the commissure tab assembly outward along a radial direction of the frame is further restrained by interaction of the one or more external wedges with a corresponding portion of the window of the support member.

Clause 65. The method of any one of clauses 53-64, wherein the one or more external wedges comprise separate wedge members.

Clause 66. The method of any one of clauses 53-64, wherein the one or more external wedges comprise separate wedge members.

Clause 67. The method of clause 66, wherein the single-continuous wedge member is substantially U-shaped.

Clause 68. The method of any one of clauses 53-67, wherein the coupling member comprises a cloth or fabric.

Clause 69. The method of any one of clauses 53-68, wherein each wedge comprises a braided polymer suture or cable.

Clause 70. The method of any one of clauses 53-69, wherein each window comprises an opening or channel that extends through a thickness of the support member along the radial direction.

Clause 71. The method of any one of clauses 53-70, wherein each window comprises an opening or channel defined by a wireform coupled to the support member.

Clause 72. An assembly method for a prosthetic heart valve, the method comprising:
disposing tabs of adjacent leaflets together, each leaflet having a pair of tabs on opposite sides with respect to a centerline thereof;
stitching together a coupling member and a wedge via a first suture;
disposing the coupling member over surface portions and between the pair of tabs of the adjacent leaflets such that the wedge is between facing surfaces of the coupling member and between facing surfaces of the tabs;
stitching together the tabs and the coupling member via a second suture, the second suture being disposed between the wedge and ends of the tabs to form a commissure tab assembly;
conveying a first portion of the commissure tab assembly into a window of a support member of an expandable frame of the prosthetic heart valve, the conveying being along an axial direction of the expandable frame from a proximal, open end of the window to a distal end of the window,
wherein, at a radial location corresponding to the wedge, the commissure tab assembly has a second portion with an increased width along a circumferential direction of the annular frame as compared to the first portion,
wherein the increased width of the second portion is greater than a width along the circumferential direction for a corresponding portion of a radially-outer side of the window, and
wherein movement of the commissure tab assembly inward along a radial direction of the frame is restrained by interaction of the second portion of the commissure tab assembly with the corresponding portion of the window of the support member.

Clause 73. The method of clause 72, wherein the expandable frame of the prosthetic heart valve comprises an annular frame having an inflow end and an outflow end separated from the inflow end along the axial direction of the frame, and/or the support member is coupled to the expandable frame.

Clause 74. The method of any one of clauses 72-73, wherein the expandable frame is radially collapsible and expandable between a radially-compressed configuration and a radially-expanded configuration.

Clause 75. The method of any one of clauses 72-74, wherein:
after the conveying, free ends of the coupling member extend from a radially-inner side of the window,
the method further comprises wrapping each free end around an adjacent portion of the support member toward the radially-outer side of the window, and
the stitching together the tabs is after the conveying and comprises stitching together the free ends, the tabs, and portions of the coupling member between the free ends via the second suture.

Clause 76. The method of any one of clauses 72-74, wherein:
after the conveying, free ends of the coupling member are folded over to extend away from a radially-inner side of the window, and
the stitching together the tabs is after the conveying and comprises stitching together the free ends, the tabs, and portions of the coupling member between the free ends via the second suture.

Clause 77. The method of any one of clauses 72-74, wherein:
after the conveying, free ends of the coupling member are folded over to form pockets at a radially-inner side of the window and to extend through the window to the radially-outer side,
the method further comprises inserting one or more external wedges into the pockets formed by the folded free ends, and
movement of the commissure tab assembly outward along a radial direction of the frame is further restrained by interaction of the one or more external wedges with a corresponding portion of the window of the support member.

Clause 78. The method of any one of clauses 72-77, wherein the one or more external wedges comprise separate wedge members.

Clause 79. The method of any one of clauses 72-77, wherein the one or more external wedges comprises a single-continuous wedge member.

Clause 80. The method of clause 79, wherein the single-continuous wedge member is substantially U-shaped.

Clause 81. The method of any one of clauses 72-80, wherein the coupling member comprises a cloth or fabric.

Clause 82. The method of any one of clauses 72-81, wherein each wedge comprises a braided polymer suture or cable.

Clause 83. The method of any one of clauses 72-82, wherein each window comprises an opening or channel that extends through a thickness of the support member along the radial direction.

Clause 84. The method of any one of clauses 72-83, wherein each window comprises an opening or channel defined by a wireform coupled to the support member.

Clause 85. An assembly method for a prosthetic heart valve, the method comprising:
disposing tabs of adjacent leaflets together, each leaflet having a pair of tabs on opposite sides with respect to a centerline thereof;
disposing one or more external wedges adjacent to external surfaces of the tabs of the adjacent leaflets;
stitching together the tabs and the one or more external wedges via at least one first suture to form a commissure tab assembly;

conveying a first portion of the commissure tab assembly into a window of a support member of an expandable frame of the prosthetic heart valve, the conveying being along an axial direction of the expandable frame from a proximal, open end of the window to a distal end of the window, wherein, at a radial location corresponding to the one or more external wedges, the commissure tab assembly has a second portion with an increased width along a circumferential direction of the annular frame as compared to the first portion, wherein the increased width of the second portion is greater than a width along the circumferential direction for a corresponding portion of a radially-outer side of the window, and wherein movement of the commissure tab assembly inward along a radial direction of the frame is restrained by interaction of the second portion of the commissure tab assembly with the corresponding portion of the window of the support member.

Clause 86. The method of clause 85, wherein the expandable frame of the prosthetic heart valve comprises an annular frame having an inflow end and an outflow end separated from the inflow end along the axial direction of the frame, and/or the support member is coupled to the expandable frame.

Clause 87. The method of any one of clauses 85-86, wherein the expandable frame is radially collapsible and expandable between a radially-compressed configuration and a radially-expanded configuration.

Clause 88. The method of any one of clauses 85-87, wherein:
the disposing tabs of adjacent leaflets comprises providing a coupling member over the pair of tabs of the adjacent leaflets,
the one or more external wedges are disposed on exposed surface portions of the coupling member, and
the stitching together the tabs and the one or more external wedges comprises stitching together the coupling member, the tabs, and the one or more external wedges via the at least one first suture.

Clause 89. The method of any one of clauses 85-88, wherein after the conveying, free ends of the coupling member extend from the radially-inner side of the window, and the method further comprises:
wrapping each free end around an adjacent portion of the support member toward the radially-outer side of the window; and
stitching together the free ends, the tabs, and portions of the coupling member between the free ends via a second suture.

Clause 90. The method of any one of clauses 85-89, wherein the one or more external wedges comprise separate wedge members.

Clause 91. The method of any one of clauses 85-89, wherein the one or more external wedges comprises a single-continuous wedge member.

Clause 92. The method of clause 91, wherein the single-continuous wedge member is substantially U-shaped.

Clause 93. The method of any one of clauses 85-92, wherein the coupling member comprises a cloth or fabric.

Clause 94. The method of any one of clauses 85-93, wherein each wedge comprises a braided polymer suture or cable.

Clause 95. The method of any one of clauses 85-94, wherein each window comprises an opening or channel that extends through a thickness of the support member along the radial direction.

Clause 96. The method of any one of clauses 85-95, wherein each window comprises an opening or channel defined by a wireform coupled to the support member.

Clause 97. An assembly method for a prosthetic heart valve, the method comprising:
overlapping a first tab of a first leaflet with a second tab of an adjacent second leaflet, each leaflet having a pair of tabs on opposite sides with respect to a centerline thereof;
disposing a first wedge on an exposed surface of the second tab in a region where the second tab overlaps with the first tab;
disposing a second wedge on an exposed surface of the first tab in a region where the second tab overlaps with the first tab;
stitching together the first and second tabs and the first and second wedges via a first suture;
wrapping the first and second tabs around the first wedge to form a commissure tab assembly, the wrapping being such that remaining portions of the first and second leaflets extend in a common direction and such that a pocket is formed by the wrapped first and second tabs enclosing the first wedge; and
conveying a first portion of the commissure tab assembly into a window of a support member of an expandable frame of the prosthetic heart valve, the conveying being along an axial direction of the expandable frame from a proximal, open end of the window to a distal end of the window,
wherein, at a radial location corresponding to the first wedge, the commissure tab assembly has a second portion with an increased width along a circumferential direction of the frame as compared to the first portion,
wherein the increased width of the second portion is greater than a width along the circumferential direction for a corresponding portion of a radially-outer side of the window, and
wherein movement of the commissure tab assembly inward along a radial direction of the frame is restrained by interaction of the second portion of the commissure tab assembly with the corresponding portion of the window of the support member.

Clause 98. The method of clause 97, wherein the expandable frame of the prosthetic heart valve comprises an annular frame having an inflow end and an outflow end separated from the inflow end along the axial direction of the frame, and/or the support member is coupled to the expandable frame.

Clause 99. The method of any one of clauses 97-98, wherein the expandable frame is radially collapsible and expandable between a radially-compressed configuration and a radially-expanded configuration.

Clause 100. The method of any one of clauses 97-99, wherein a diameter of the first wedge is greater than a diameter of the second wedge, a length of the first wedge is less than a length of the second wedge, and a length of the first wedge is less than a height of the first tab or the second tab.

Clause 101. The method of any one of clauses 97-100, wherein the second wedge has free ends that extend beyond top and bottom edges of the first tab.

Clause 102. The method of any one of clauses 97-101, the method comprising inserting the free ends of the second wedge into corresponding end portions of the first wedge.

Clause 103. The method of any one of clauses 97-102, the method comprising disposing the free ends of the second wedge adjacent to the first wedge in the pocket formed by the wrapped tabs.

Clause 104. The method of any one of clauses 97-103, wherein the one or more external wedges comprise separate wedge members.

Clause 105. The method of any one of clauses 97-103, wherein the one or more external wedges comprises a single-continuous wedge member.

Clause 106. The method of clause 105, wherein the single-continuous wedge member is substantially U-shaped.

Clause 107. The method of any one of clauses 97-106, wherein the coupling member comprises a cloth or fabric.

Clause 108. The method of any one of clauses 97-107, wherein each wedge comprises a braided polymer suture or cable.

Clause 109. The method of any one of clauses 97-108, wherein each window comprises an opening or channel that extends through a thickness of the support member along the radial direction.

Clause 110. The method of any one of clauses 97-109, wherein each window comprises an opening or channel defined by a wireform coupled to the support member.

Clause 111. An assembly method for a prosthetic heart valve, the method comprising:
  disposing tabs of adjacent leaflets together, each leaflet having a pair of tabs on opposite sides with respect to a centerline thereof;
  disposing one or more external wedges adjacent to external surfaces of the tabs of the adjacent leaflets;
  stitching together the tabs and the one or more external wedges via at least one first suture;
  wrapping a free end portion of each tab around a respective one of the external wedges to form a commissure tab assembly, the wrapping being such that the free end portions of the tabs and remaining portions of the leaflets extend in a common direction and such that pockets are formed by the wrapped free end portions enclosing the external wedges; and
  conveying a first portion of the commissure tab assembly into a window of a support member of an expandable frame of the prosthetic heart valve, the conveying being along an axial direction of the expandable frame from a proximal, open end of the window to a distal end of the window,
  wherein, at a radial location corresponding to the one or more external wedges, the commissure tab assembly has a second portion with an increased width along a circumferential direction of the annular frame as compared to the first portion,
  wherein the increased width of the second portion is greater than a width along the circumferential direction for a corresponding portion of a radially-outer side of the window, and
  wherein movement of the commissure tab assembly inward along a radial direction of the frame is restrained by interaction of the second portion of the commissure tab assembly with the corresponding portion of the window of the support member.

Clause 112. The method of clause 111, wherein the expandable frame of the prosthetic heart valve comprises an annular frame having an inflow end and an outflow end separated from the inflow end along the axial direction of the frame, and/or the support member is coupled to the expandable frame.

Clause 113. The method of any one of clauses 111-112, wherein the expandable frame is radially collapsible and expandable between a radially-compressed configuration and a radially-expanded configuration.

Clause 114. The method of any one of clauses 111-113, wherein each wrapped free end portion extends from the radially-outer side of the window toward the radially-inner side of the window.

Clause 115. The method of any one of clauses 111-114, wherein a respective end of each free end portion is disposed along the radial direction adjacent to the radially-inner side of the window.

Clause 116. The method of any one of clauses 111-115, wherein a thickness of the first portion of the commissure tab assembly is about four times a thickness of each leaflet tab.

Clause 117. The method of any one of clauses 111-116, wherein:
  the disposing tabs of adjacent leaflets comprises providing one or more coupling members over surface portions of the pair of tabs of the adjacent leaflets, each coupling member being on an opposite side of the respective tab from the one or more external wedges,
  the stitching together the tabs and internal wedge comprises stitching together each coupling member, the tabs, and each external wedge via the at least one first suture, and
  the wrapping includes wrapping free end portions of each tab and coupling member around a respective one of the external wedges to form a commissure tab assembly.

Clause 118. The method of any one of clauses 111-117, wherein:
  the at least one first suture is two first sutures and the one or more coupling members is two coupling members, and
  one of the tabs, one of the coupling members, and one of the external wedges being coupled together by one of the first sutures, and the other of the tabs, the other of the coupling members, and the other of the external wedges being coupled together by the other of the first sutures.

Clause 119. The method of clause 118, wherein the portion of each coupling members stitched by the first sutures comprises a folded-over, double-thickness portion of the respective coupling member.

Clause 120. The method of any one of clauses 111-119, wherein:
  after the conveying, free ends of the one or more coupling members extend from the radially-inner side of the window,
  the method comprises wrapping each free end around an adjacent portion of the support member toward the radially-outer side of the window, and
  the method comprises stitching the free ends of the one or more coupling members to the second portion of the commissure tab assembly.

Clause 121. The method of any one of clauses 111-120, wherein the one or more external wedges comprise separate wedge members.

Clause 122. The method of any one of clauses 111-120, wherein the one or more external wedges comprise separate wedge members.

Clause 123. The method of clause 122, wherein the single-continuous wedge member is substantially U-shaped.

Clause 124. The method of any one of clauses 111-123, wherein the coupling member comprises a cloth or fabric.

Clause 125. The method of any one of clauses 111-124, wherein each wedge comprises a braided polymer suture or cable.

Clause 126. The method of any one of clauses 111-125, wherein each window comprises an opening or channel that extends through a thickness of the support member along the radial direction.

Clause 127. The method of any one of clauses 111-126, wherein each window comprises an opening or channel defined by a wireform coupled to the support member.

Clause 128. The method of any one of clauses 1-127, wherein the valvular structure is a bicuspid structure with two leaflets and two commissure tab assemblies, and the commissure support posts are on diametrically opposite sides of the frame from each other.

Clause 129. The method of any one of clauses 1-127, wherein the valvular structure is a tricuspid structure with three leaflets and three commissure tab assemblies, and the commissure support posts are equally spaced around a circumference of the frame.

Clause 130. The method of any one of clauses 1-129, wherein the frame is formed of a plastically-expandable material or a self-expanding material.

Clause 131. The method of any one of clauses 1-129, wherein the frame comprises an array of angled struts connected together by one or more pivot joints.

Clause 132. A prosthetic heart valve, comprising:
  a frame that is radially collapsible and expandable between a radially-compressed configuration and a radially-expanded configuration, the frame having an inflow end and an outflow end separated from the inflow end along an axial direction of the frame, the frame comprising a plurality of support posts; and
  a valvular structure supported within the annular frame and comprising a plurality of leaflets, each leaflet having a pair of tabs, the tabs of adjacent leaflets being coupled together to form a commissure tab assembly, wherein there is one support post for each commissure tab assembly, and
  each commissure tab assembly is coupled to the respective support post according to the method of any of clauses 1-131.

Clause 133. The prosthetic heart valve of clause 132, wherein the support posts comprise portions of actuator or locking mechanisms of the frame.

Clause 134. The prosthetic heart valve of clause 132, wherein the support posts are coupled to actuator or locking mechanisms of the annular frame.

Clause 135. The prosthetic heart valve of any one of clauses 132-134, wherein the valvular structure is a bicuspid structure with two leaflets and two commissure tab assemblies, and the valvular structure is coupled to the frame via the commissure tab assemblies on diametrically opposite sides of the frame from each other.

Clause 136. The prosthetic heart valve of any one of clauses 132-134, wherein the valvular structure is a tricuspid structure with three leaflets and three commissure tab assemblies, and the valvular structure is coupled to the frame via the three commissure tab assemblies equally spaced along the circumferential direction of the frame.

Clause 137 The prosthetic heart valve of any one of clauses 132-136, wherein the frame comprises an annular frame.

Clause 138. The prosthetic heart valve of any one of clauses 132-137, wherein the frame is formed of a plastically-expandable material or a self-expanding material.

Clause 139. The prosthetic heart valve of any one of clauses 132-137, wherein the annular frame comprises an array of angled struts connected together by one or more pivot joints.

Clause 140. The prosthetic heart valve of any one of clauses 132-139, wherein the prosthetic heart valve is constructed for implantation in an existing heart valve within a patient.

Clause 141. The prosthetic heart valve of any one of clauses 132-140, wherein the prosthetic heart valve is constructed for implantation at an aortic position or a mitral position.

Clause 142. An assembly, comprising:
  a delivery apparatus comprising an elongated shaft; and
  the prosthetic heart valve of any one of clauses 132-140 mounted on the elongated shaft in the radially-compressed configuration for delivery into a patient's body.

Clause 143. A method of implanting a prosthetic heart valve in a patient's body, the method comprising:
  inserting a distal end of a delivery apparatus into vasculature of a patient, the delivery apparatus comprising an elongated shaft, the prosthetic heart valve of any one of clauses 132-140 being releasably mounted in the radially-compressed configuration on the elongated shaft of the delivery apparatus;
  advancing the prosthetic heart valve to a desired implantation site; and
  using the delivery apparatus to expand the prosthetic heart valve to the radially-expanded configuration, thereby implanting the prosthetic heart valve at the desired implantation site.

Clause 144. A method of implanting a prosthetic heart valve in a patient's body, the method comprising:
  inserting a distal end of a delivery apparatus into vasculature of a patient, the delivery apparatus comprising an elongated shaft, the prosthetic heart valve of any one of clauses 132-140 being releasably mounted in the radially-compressed configuration on the elongated shaft of the delivery apparatus;
  advancing the prosthetic heart valve to a desired implantation site; and
  deploying the prosthetic heart valve from the delivery apparatus such that the prosthetic heart valve self-expands to the radially-expanded configuration, thereby implanting the prosthetic heart valve at the desired implantation site.

Clause 145. The method of any one of clauses 143-144, wherein the advancing to the desired implantation site employs transfemoral, transventricular, transapical, or transseptal approaches.

General Considerations

All features described herein are independent of one another and, except where structurally impossible, can be used in combination with any other feature described herein. For example, the wire form configuration illustrated in FIGS. 20A-20E can be used in place of any of the open or closed window configurations described with respect to FIGS. 5A-19D.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present, or problems be solved. The technologies from any example can be combined with the technologies described in any one or more of the other examples.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used herein with reference to the prosthetic heart valve assembly and implantation and structures of the prosthetic heart valve, "proximal" refers to a position, direction, or portion of a component that is closer to the user and a handle of the delivery system or apparatus that is outside the patient, while "distal" refers to a position, direction, or portion of a component that is further away from the user and the handle, and closer to the implantation site. The terms "longitudinal" and "axial" refer to an axis extending in the proximal and distal directions, unless otherwise expressly defined.

The terms "axial direction," "radial direction," and "circumferential direction" have been used herein to describe the arrangement and assembly of components relative to the geometry of the frame of the prosthetic heart valve. Such terms have been used for convenient description, but the disclosed embodiments are not strictly limited to the description. In particular, where a component or action is described relative to a particular direction, directions parallel to the specified direction as well as minor deviations therefrom are included. Thus, a description of a component extending along an axial direction of the frame does not require the component to be aligned with a center of the frame; rather, the component can extend substantially along a direction parallel to a central axis of the frame.

As used herein, the terms "integrally formed" and "unitary construction" refer to a construction that does not include any welds, fasteners, or other means for securing separately formed pieces of material to each other.

As used herein, operations that occur "simultaneously" or "concurrently" occur generally at the same time as one another, although delays in the occurrence of operation relative to the other due to, for example, spacing between components, are expressly within the scope of the above terms, absent specific contrary language.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language. As used herein, "and/or" means "and" or "or," as well as "and" and "or."

Directions and other relative references may be used to facilitate discussion of the drawings and principles herein, but are not intended to be limiting. For example, certain terms may be used such as "inner," "outer," "upper," "lower," "inside," "outside,", "top," "bottom," "interior," "exterior," "left," "right," and the like. Such terms are used, where applicable, to provide some clarity of description when dealing with relative relationships, particularly with respect to the illustrated examples. Such terms are not, however, intended to imply absolute relationships, positions, and/or orientations. For example, with respect to an object, an "upper" part can become a "lower" part simply by turning the object over. Nevertheless, it is still the same part and the object remains the same.

In view of the many possible embodiments to which the principles of the disclosed technology may be applied, it should be recognized that the illustrated examples are only preferred examples and should not be taken as limiting the scope of the disclosed technology. Rather, the scope of the disclosed technology is defined by the following claims. We therefore claim all that comes within the scope of these claims.

The invention claimed is:

1. An assembly method for a prosthetic heart valve, the method comprising:
   disposing tabs of adjacent leaflets together, each leaflet having a pair of tabs on opposite sides with respect to a centerline thereof;
   disposing one or more external wedges adjacent to external surfaces of the tabs of the adjacent leaflets;
   stitching together the tabs and the one or more external wedges via at least one first suture;
   wrapping a free end portion of each tab around a respective one of the external wedges to form a commissure tab assembly, the wrapping being such that the free end portions of the tabs and remaining portions of the leaflets extend in a common direction and such that pockets are formed by the wrapped free end portions enclosing the external wedges; and
   conveying a first portion of the commissure tab assembly into a window of a support member of an expandable annular frame of the prosthetic heart valve, the conveying being along an axial direction of the expandable annular frame from a proximal, open end of the window to a distal end of the window.

2. The method of claim 1, wherein, at a radial location corresponding to the one or more external wedges, the commissure tab assembly has a second portion with an increased width along a circumferential direction of the annular frame as compared to the first portion.

3. The method of claim 2, wherein the increased width of the second portion is greater than a width along the circumferential direction for a corresponding portion of a radially-outer side of the window.

4. The method of claim 3, wherein movement of the commissure tab assembly inward along a radial direction of the frame is restrained by interaction of the second portion of the commissure tab assembly with the corresponding portion of the window of the support member.

5. The method of claim 3, wherein each wrapped free end portion extends from the radially-outer side of the window toward a radially-inner side of the window.

6. The method of claim 5, wherein a respective end of each free end portion is disposed along a radial direction of the frame adjacent to the radially-inner side of the window.

7. The method of claim 6, wherein:
the disposing tabs of adjacent leaflets comprises providing one or more coupling members over surface portions of the pair of tabs of the adjacent leaflets, each coupling member being on an opposite side of the respective tab from the one or more external wedges,
the stitching together the tabs and internal wedge comprises stitching together each coupling member, the tabs, and each external wedge via the at least one first suture, and
the wrapping includes wrapping free end portions of each tab and coupling member around a respective one of the external wedges to form a commissure tab assembly.

8. The method of claim 7, wherein:
the at least one first suture is two first sutures and the one or more coupling members is two coupling members, and
one of the tabs, one of the coupling members, and one of the external wedges being coupled together by one of the first sutures, and the other of the tabs, the other of the coupling members, and the other of the external wedges being coupled together by the other of the first sutures.

9. The method of claim 8, wherein:
after the conveying, free ends of the one or more coupling members extend from the radially-inner side of the window,
the method comprises wrapping each free end around an adjacent portion of the support member toward the radially-outer side of the window, and
the method comprises stitching the free ends of the one or more coupling members to the second portion of the commissure tab assembly.

10. The method of claim 1, wherein the one or more external wedges comprises a single continuous wedge member that is substantially U-shaped.

11. The method of claim 7, wherein the one or more coupling members comprise a cloth or fabric, or each wedge comprises a braided polymer suture or cable.

12. The method of claim 1, wherein each window comprises an opening or channel that extends through a thickness of the support member along a radial direction, or each window comprises an opening or channel defined by a wireform coupled to the support member.

13. An assembly method for a prosthetic heart valve, the method comprising:
disposing tabs of adjacent leaflets together, each leaflet having a pair of tabs on opposite sides with respect to a centerline thereof;
disposing one or more external wedges adjacent to external surfaces of the tabs of the adjacent leaflets;
stitching together the tabs and the one or more external wedges via at least one first suture to form a commissure tab assembly; and
conveying a first portion of the commissure tab assembly into a window of a support member of an expandable annular frame of the prosthetic heart valve, the conveying being along an axial direction of the expandable annular frame from a proximal, open end of the window to a distal end of the window,
wherein, at a radial location corresponding to the one or more external wedges, the commissure tab assembly has a second portion with an increased width along a circumferential direction of the annular frame as compared to the first portion,
wherein the increased width of the second portion is greater than a width along the circumferential direction for a corresponding portion of a radially-outer side of the window, and
wherein movement of the commissure tab assembly inward along a radial direction of the frame is restrained by interaction of the second portion of the commissure tab assembly with the corresponding portion of the window of the support member.

14. The method of claim 13, wherein:
the disposing tabs of adjacent leaflets comprises providing a coupling member over the pair of tabs of the adjacent leaflets,
the one or more external wedges are disposed on exposed surface portions of the coupling member, and
the stitching together the tabs and the one or more external wedges comprises stitching together the coupling member, the tabs, and the one or more external wedges via the at least one first suture.

15. The method of claim 14, wherein after the conveying, free ends of the coupling member extend from a radially-inner side of the window, and the method further comprises:
wrapping each free end around an adjacent portion of the support member toward the radially-outer side of the window; and
stitching together the free ends, the tabs, and portions of the coupling member between the free ends via a second suture.

* * * * *